(12) United States Patent
Ray et al.

(10) Patent No.: US 9,897,592 B2
(45) Date of Patent: Feb. 20, 2018

(54) METHODS FOR IDENTIFYING ARTHROPOD REPELLENTS AND ATTRACTANTS, AND COMPOUNDS AND COMPOSITIONS IDENTIFIED BY SUCH METHODS

(71) Applicant: The Regents of the University of California, Oakland, CA (US)

(72) Inventors: Anandasankar Ray, Riverside, CA (US); Sean Michael Boyle, Lakewood Ranch, FL (US); Dyan MacWilliam, Riverside, CA (US); Genevieve Mitchell Tauxe, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/494,401

(22) Filed: Apr. 21, 2017

(65) Prior Publication Data

US 2017/0292944 A1    Oct. 12, 2017

Related U.S. Application Data

(63) Continuation of application No. 14/855,024, filed on Sep. 15, 2015, now abandoned, which is a continuation of application No. PCT/US2014/029201, filed on Mar. 14, 2014.

(60) Provisional application No. 61/799,734, filed on Mar. 15, 2013.

(51) Int. Cl.

| *A61K 49/00* | (2006.01) |
| *A01N 35/02* | (2006.01) |
| *A01N 31/06* | (2006.01) |
| *A01N 43/36* | (2006.01) |
| *A01N 37/42* | (2006.01) |
| *A01N 43/10* | (2006.01) |
| *A01N 43/08* | (2006.01) |
| *A01N 41/10* | (2006.01) |
| *A01N 33/04* | (2006.01) |
| *A01N 35/06* | (2006.01) |
| *A01N 35/08* | (2006.01) |
| *A01N 31/02* | (2006.01) |
| *G01N 33/50* | (2006.01) |

(52) U.S. Cl.
CPC ......... *G01N 33/5058* (2013.01); *A01N 31/02* (2013.01); *A01N 35/08* (2013.01); *G01N 33/5032* (2013.01); *A01N 31/06* (2013.01); *A01N 33/04* (2013.01); *A01N 35/02* (2013.01); *A01N 35/06* (2013.01)

(58) Field of Classification Search
CPC .... A01N 2300/00; A01N 37/02; A01N 65/00; A01N 53/00; A01N 31/02; A01N 37/36; A01N 65/22; A01N 25/04; A01N 25/06; A01N 27/00; A01N 25/02; A01N 25/16; A01N 47/02; A01N 31/04; A01N 35/04

See application file for complete search history.

(56) References Cited

U.S. PATENT DOCUMENTS

| 5,089,469 A | 2/1992 | Zampino et al. |
| 5,175,175 A | 12/1992 | Wilson et al. |
| 5,354,783 A | 10/1994 | Marin et al. |
| 6,267,953 B1 | 7/2001 | Bernier et al. |
| 6,372,804 B1 | 4/2002 | Ikemoto et al. |
| 6,719,959 B1 | 4/2004 | Gonzalez et al. |
| 6,800,279 B2 | 10/2004 | Bernier et al. |
| 6,958,146 B2 | 10/2005 | Askham et al. |
| 7,867,479 B2 | 1/2011 | Dunham et al. |
| 8,048,683 B2 | 11/2011 | Grau et al. |
| 8,092,790 B2 | 1/2012 | Dunham et al. |
| 8,945,595 B2 | 2/2015 | Ray et al. |
| 9,307,763 B2 | 4/2016 | Ray et al. |
| 9,491,942 B2 | 11/2016 | Ray et al. |
| 2002/0028191 A1 | 3/2002 | Bernier et al. |
| 2004/0223998 A1 | 11/2004 | Iyer et al. |
| 2004/0242699 A1 | 12/2004 | Askham et al. |
| 2005/0008714 A1 | 1/2005 | Enan |
| 2006/0189690 A1 | 8/2006 | Dunham et al. |
| 2006/0193881 A1 | 8/2006 | Bedoukian |
| 2007/0142795 A1 | 6/2007 | Cohen et al. |
| 2007/0157323 A1 | 7/2007 | Carlson et al. |
| 2009/0047379 A1 | 2/2009 | Dewis et al. |
| 2009/0148398 A1 | 6/2009 | Vander et al. |
| 2009/0176229 A1 | 7/2009 | Tracey, Jr. et al. |
| 2009/0196838 A1 | 8/2009 | Gupta et al. |

(Continued)

FOREIGN PATENT DOCUMENTS

| CN | 1809368 A | 7/2006 |
| JP | 2000-290104 A | 10/2000 |

(Continued)

OTHER PUBLICATIONS

Dekker et al., "Identification of Mosquito Repellent Odours from Ocimum Forskolei", Parasites & Vectors, vol. 4, No. 183, 2011, pp. 1-7.

(Continued)

*Primary Examiner* — Audrea Buckley
(74) *Attorney, Agent, or Firm* — Morrison & Foerster LLP

(57) ABSTRACT

Provided herein are screening methods for identifying compounds for use as an arthropod repellent based on the masking or inhibition of the detection of the skin odor by a cpA neuron. Provided herein are also screening methods for identifying compounds for use as an arthropod attractant based on activation of the cpA neuron. Further provided are one or more compounds identified using the screening methods described herein, and compositions containing such compounds.

1 Claim, 52 Drawing Sheets

(56) References Cited

U.S. PATENT DOCUMENTS

| | | | |
|---|---|---|---|
| 2010/0074972 | A1 | 3/2010 | Rouseff et al. |
| 2010/0144888 | A1 | 6/2010 | Bessette |
| 2010/0247684 | A1 | 9/2010 | Reid et al. |
| 2011/0244056 | A1 | 10/2011 | Santra |
| 2011/0263585 | A1 | 10/2011 | Bernasconi et al. |
| 2012/0015841 | A1 | 1/2012 | Shekdar et al. |
| 2013/0236417 | A1 | 9/2013 | Ray et al. |
| 2015/0126437 | A1 | 5/2015 | Ray et al. |
| 2015/0223458 | A1 | 8/2015 | Ray et al. |
| 2015/0377897 | A1 | 12/2015 | Ray et al. |
| 2017/0079274 | A1 | 3/2017 | Ray et al. |

FOREIGN PATENT DOCUMENTS

| | | |
|---|---|---|
| WO | 1998/23150 A1 | 6/1998 |
| WO | 2000/65910 A1 | 11/2000 |
| WO | 2002/00021 A2 | 1/2002 |
| WO | 2007/056043 A2 | 5/2007 |
| WO | 2010/102049 A2 | 9/2010 |
| WO | 2010/143752 A2 | 12/2010 |
| WO | 2011/040252 A1 | 4/2011 |
| WO | 2012/018153 A1 | 2/2012 |
| WO | 2013/059364 A2 | 4/2013 |

OTHER PUBLICATIONS

Jones, Walton, "Olfactory Carbon Dioxide Detection by Insects and Other Animals", Molecules and Cells, vol. 35, Feb. 28, 2013, pp. 87-92.
Non-Final Office Action received for U.S. Appl. No. 14/855,024, dated Nov. 22, 2016, 8 pages.
Abramson et al., "Proboscis Conditioning Experiments with Honeybees, Apis Mellifera Caucasica, with Butyric Acid and DEET Mixture as Conditioned and Unconditioned Stimuli", Journal of Insect Science, vol. 10, No. 122, 2010, pp. 1-17.
Abuin et al., "Functional Architecture of Olfactory Ionotropic Glutamate Receptors", Neuron, vol. 69, No. 1, Jan. 13, 2011, pp. 44-60.
Al et al., "Acid Sensing by the *Drosophila* Olfactory System", Nature, vol. 468, No. 7324, Dec. 2, 2010, pp. 691-695.
Andreev K.P, "New Insect Repellents for Protection of Humans and Animals from Bloodsucking Flies, Mosquitoes, Midges, and Gnats", Chemical Abstracts Service, Columbus, Ohio, US; 1958, XP-002744302, Database Accession No. 1960:64502.
Baccino et al., "Sharing an Olfactory Experience: The Impact of Oral Communication", Food Quality and Preference, vol. 21, 2010, pp. 443-452.
Bar-Zeev et al., "The Response of the Adults of the Khapra Beetle *Trogoderma granarium* Everts (Coleoptera, Dermestidae) to Various Synthetic Compounds", Rivista Di Parassitologia, vol. XL, No. 1/2, 1979, pp. 49-55.
Bell et al., "Behavior Reveals Selective Summation and Max Pooling among Olfactory Processing Channels", Neuron, vol. 91, Jul. 20, 2016, pp. 425-438.
Benton et al., "Variant Ionotropic Glutamate Receptors as Chemosensory Receptors in *Drosophila*", Cell, vol. 136, Jan. 9, 2009, pp. 149-162.
Bernier et al., "Analysis of Human Skin Emanations by Gas Chromatography/Mass Spectrometry. 1. Thermal Desorption of Attractants for the Yellow Fever Mosquito (*Aedes aegypti*) from Handled Glass Beads", Analytical Chemistry, vol. 71, No. 1, Jan. 1, 1999, pp. 1-7.
Bernier et al., "Analysis of Human Skin Emanations by Gas Chromatography/Mass Spectrometry. 2. Identification of Volatile Compounds that are Candidate Attractants for the Yellow Fever Mosquito (*Aedes aegypti*)", Analytical Chemistry, vol. 72, No. 4, Feb. 15, 2000, pp. 747-756.
Boeckh et al., "Acylated 1,3-Aminopropanols as Repellents against Bloodsucking Arthropods", Pesticide Science, vol. 48, 1996, pp. 359-373.

Bohbot et al., "Selectivity of Odorant Receptors in Insects", Frontiers in Cellular Neuroscience, vol. 6, Article 29, Jul. 2012, pp. 1-4.
Braks et al., "Infochemicals in Mosquito Host Selection: Human Skin Microflora and Plasmodium Parasites", Parasitology Today, vol. 15, No. 10, 1999, pp. 409-413.
Bruyne et al., "Odor Coding in a Model Olfactory Organ: The *Drosophila* Maxillary Palp", The Journal of Neuroscience, vol. 19, No. 11, Jun. 1, 1999, pp. 4520-4532.
Burton, D. J., "Intrinsic Mosquito Repellency Values of Some Chemical Compounds", American Perfumer and Cosmetics, vol. 84, Apr. 1969, pp. 41-44.
Butler, Declan, "Mosquitoes Score in Chemical War", Nature, vol. 475, Jul. 7, 2011, 1 page.
Cardé et al., "Host Finding by Female Mosquitoes: Mechanisms of Orientation to Host Odours and Other Cues", Olfaction in Vector-Host Interactions, 2010, pp. 115-141.
Cardé et al., "Navigational Strategies Used by Insects to Find Distant, Wind-Borne Sources of Odor", J. Chem. Ecol., vol. 34, 2008, pp. 854-866.
Carey et al., "Odorant Reception in the Malaria Mosquito Anopheles Gambiae", Nature, 2010, pp. 1-7.
Chang et al., "LIBSVM: A Library for Support Vector Machines", This LIBSVM implementation document was created in 2001 and has been maintained at http://www.csie.ntu.edu.tw/~cjlin/papers/libsvm.pdf, 2001, pp. 1-39.
"Chemical Products Catalog (Shanghai)", Scientific and Technical Information Research Institute of Bureau of Chemical Industry, Shanghai, Feb. 1992, pp. 177, 180, 450. (See Communication under 37 CFR § 1.98(a) (3)).
Chiang et al., "Three-Dimensional Reconstruction of Brain-wide Wiring Networks in *Drosophila* at Single-Cell Resolution", Current Biology, vol. 21, No. 1, Jan. 11, 2011, pp. 1-11.
Cook et al., "The Use of Push-Pull Strategies in Integrated Pest Management", Annu. Rev. Entomol., vol. 52, 2007, pp. 375-400.
Cooperband et al., "Orientation of Culex Mosquitoes to Carbon Dioxidebaited Traps: Flight Manoeuvres and Trapping Efficiency", Medical and Veterinary Entomology, vol. 20, 2006, pp. 11-26.
Corbel et al., "Evidence for Inhibition of Cholinesterases in Insect and Mammalian Nervous Systems by the Insect Repellent DEET", BMC Biology, vol. 7, No. 47, 2009, pp. 1-11.
Cork et al., "Identification of Electrophysiologically-Active Compounds for the Malaria Mosquito, Anopheles Gambiae, in Human Sweat Extracts", Medical and Veterinary Entomology, vol. 10, 1996, pp. 269-276.
Cortes et al., "Support-Vector Networks", Machine Learning, vol. 20, 1995, pp. 273-297.
Croset et al., "Ancient Protostome Origin of Chemosensory Ionotropic Glutamate Receptors and the Evolution of Insect Taste and Olfaction", PLoS Genetics, vol. 6, No. 8, e1001064, Aug. 2010, pp. 1-20.
Curran et al., "Comparison of the Volatile Organic Compounds Present in Human Odor Using Spme-gc/ms", Journal of Chemical Ecology, vol. 31, No. 7, Jul. 2005, pp. 1607-1619.
Dekker et al., "Moment-to-Moment Flight Manoeuvres of the Female Yellow Fever Mosquito (*Aedes aegypti* L.) in response to Plumes of Carbon Dioxide and Human Skin Odour", The Journal of Experimental Biology, vol. 214, 2011, pp. 3480-3494.
Dekker et al., "Structure of Host-Odour Plumes Influences Catch of Anopheles Gambiae S.S. And Aedes Aegypti in a Dualchoice Olfactometer", Physiological Entomology, vol. 26, 2001, pp. 124-134.
Dekker et al., "Carbon Dioxide Instantly Sensitizes Female Yellow Fever Mosquitoes to Human Skin Odours", The Journal of Experimental Biology, vol. 208, 2005, pp. 2963-2972.
Ditzen et al., "Insect Odorant Receptors are Molecular Targets of the Insect Repellent DEET", Science, vol. 319, 2008, pp. 1838-1842.
Douglas et al., "Chemical Odorant of Colonial Seabird Repels Mosquitoes", Journal of Medical Entomology, vol. 42, No. 4, Jul. 2005, pp. 647-651.
Enjin et al., "Humidity Sensing in *Drosophila*", Current Biology, vol. 26, May 23, 2016, pp. 1-7.

(56) References Cited

OTHER PUBLICATIONS

Erdelyan et al., "Functional Validation of the Carbon Dioxide Receptor Genes in Aedes aegypti Mosquitoes using RNA Interference", Insect Molecular Biology, vol. 21, No. 1, 2012, pp. 119-127.

Final Office Action received for U.S. Appl. No. 12/398,164, dated Apr. 16, 2014, 17 pages.

Final Office Action received for U.S. Appl. No. 12/398,164, dated Apr. 20, 2012, 10 pages.

Fischler et al., "The Detection of Carbonation by the *Drosophila* Gustatory System", Nature, vol. 448, Aug. 30, 2007, pp. 1054-1057.

Gallagher et al., "Analyses of Volatile Organic Compounds from Human Skin", Br J Dermatol., vol. 159, No. 4, Sep. 2008, pp. 780-791.

Gaudin et al., "Carboxamides Combining Favorable Olfactory Properties with Insect Repellency", Chemistry & Biodiversity, vol. 5, 2008, pp. 617-635.

Ghaninia et al., "Natural Odor Ligands for Olfactory Receptor Neurons of the Female Mosquito *Aedes aegypti*: Use of Gas Chromatography-linked Single Sensillum Recordings", The Journal of Experimental Biology, vol. 211, 2008, pp. 3020-3027.

Gillies, M. T. "The Role of Carbon Dioxide in Host-Finding by Mosquitoes (*Diptera: culicidae*): A Review", Bull. Ent. Res., vol. 70, 1980, pp. 525-532.

Godavarthy et al., "Improved Structure-Property Relationship Models for Prediction of Critical Properties", Fluid Phase Equilibria, vol. 264, 2008, pp. 122-136.

Grant et al.,"Olfaction in Mosquito-Host Interactions", Ciba Foundation Symposium 200, 1996, 10 pages.

Gupta et al., "Discovery and Design of New Arthropod/Insect Repellents by Computer-Aided Molecular Modeling", Insect Repellents Principles, Methods, and Uses, 2006, pp. 195-228.

Gutierrez-Osuna, Ricardo, "Pattern Analysis for Machine Olfaction: A Review", IEEE Sensors Journal, vol. 2, No. 3, Jun. 2002, pp. 189-202.

Haasen et al., "Pharmacological Profiling of Chemokine Receptor-Directed Compounds Using High-Content Screening", Journal of Biomolecular Screening, vol. 13, No, 1, 2008, pp. 40-53.

Haddad et al., "A Metric for Odorant Comparison", Nature Methods, 2008, pp. 1-5.

Halbert et al., "Plant-Derived Compounds and Extracts with Potential as Aphid Repellents", Annals of Applied Biology, vol. 154, 2009, pp. 303-307.

Hallem et al., "Coding of Odors by a Receptor Repertoire", Cell, vol. 125, Apr. 7, 2006, pp. 143-160.

Hawkins et al., "Conformer Generation with OMEGA: Algorithm and Validation Using High Quality Structures from the Protein Databank and Cambridge Structural Database", J. Chem. Inf. Model, vol. 50, No. 4, 2010, pp. 572-584.

Hayes et al, "Identification of a Host Compound and its Practical Applications: 4-Allylanisole as a Bark Beetle Repellent", Chemical Abstracts Service, 1994, Feb. 1-2, 1994, pp. 69-79.

Healy et al., "Activation of Anopheles Gambiae Mosquitoes by Carbon Dioxide and Human Breath", Medical Veterinary Entomology, vol. 9, 1995, pp. 331-336.

Healy et al., "Human Sweat and 2-Oxopentanoic Acid Elicit a Landing Response from Anopheles Gambiae", Medical Veterinary Entomology, vol. 14, 2000, pp. 195-200.

Hou et al., "The Effect of Repellents on Penetration into Packaging by Stored-Products Insects", Journal of Stored Products Research, vol. 40, 2004, pp. 47-54.

Hwang et al., "Isolation and Identification of Mosquito Repellents in Artemisia Vulgaris", Journal of Chemical Ecology, vol. 11, No. 9, pp. 1297-1306. (English Abstract Submitted).

Ibrahim et al., "Toxicity and Inhibition of Feeding and Tunneling Response of Naphthalene and 10 Derivatives on the Formosan Subterranean Termite (*Isoptera rhinotermitidae*)", Journal of Economic Entomology, vol. 103, No. 6, Dec. 2010,pp. 2132-2139. (English Abstract Submitted).

Ihndris et al., "Effect of Promising Insect Repellents on Plastics and Paints", Database Accession No. 1955:86558, 1955, vol. 33, No. 7, 2 pages (English Abstract Submitted).

Innocent et al., "Constituents of the Essential Oil of Suregada Zanzibariensis Leaves are S.S", Journal of Insect Science, vol. 10, No. 57, 2010, pp. 1-8.

International Preliminary Report on Patentability received for PCT Patent Application No. PCT/US2010/026108, dated Sep. 15, 2011, 8 pages.

International Preliminary Report on Patentability received for PCT Patent Application No. PCT/US2011/032804, dated Oct. 26, 2012, 9 pages.

International Preliminary Report on Patentability received for PCT Patent Application No. PCT/US2012/060130, dated Apr. 24, 2014, 9 pages.

International Preliminary Report on Patentability received for PCT Patent Application No. PCT/US2012/060673, dated May 1, 2014, 7 pages.

International Preliminary Report on Patentability received for PCT Patent Application No. PCT/US2014/029201, dated Sep. 24, 2015, 8 pages.

International Preliminary Report on Patentability received for PCT Patent Application No. PCT/US2014/029524, dated Sep. 24, 2015, 9 pages.

International Search Report and Written Opinion received for PCT Patent Application No. PCT/US2010/026108, dated Oct. 19, 2010, 12 pages.

International Search Report and Written Opinion received for PCT Patent Application No. PCT/US2012/060130, dated Mar. 18, 2013, 13 pages.

International Search Report and Written Opinion received for PCT Patent Application No. PCT/US2012/060673, dated Apr. 1, 2013, 11 pages.

International Search Report and Written Opinion received for PCT Patent Application No. PCT/US2014/029201, dated Oct. 7, 2014, 5 pages.

International Search Report and Written Opinion received for PCT Patent Application No. PCT/US2014/029524, dated Aug. 11, 2014, 5 pages.

International Search Report received for PCT Patent Application No. PCT/US2011/032804, dated Dec. 26, 2011, 5 pages International Written Opinion received for PCT Patent Application No. PCT/US2011/032804, dated Dec. 26, 2011, 7 pages.

Invitation to Pay Additional Fees received for PCT Patent Application No. PCT/US2014/029201, dated Jul. 24, 2014, 2 pages.

Jacquin-Joly et al., "Insect Olfactory Receptors: Contributions of Molecular Biology to Chemical Ecology", Journal of Chemical Ecology, vol. 30. No. 12, Dec. 2004, pp. 2359-2397.

Jawara et al., "Field Testing of Different Chemical Combinations as Odour Baits for Trapping Wild Mosquitoes in the Gambia", PLoS ONE, vol. 6, No. 5, e19676, 2011, pp. 1-7.

Jones et al., "Allosteric Antagonism of Insect Odorant Receptor Ion Channels", PLoS One, vol. 7, No. 1, e30304, Jan. 2012, pp. 1-7.

Jones et al., "Two Chemosensory Receptors Together Mediate Carbon Dioxide Detection in *Drosophila*", Nature, vol. 445, Jan. 4, 2007, pp. 86-90.

Kain et al., "Odour Receptors and Neurons for DEET and New Insect Repellents", Nature, vol. 502, Oct. 24, 2013, pp. 507-512.

Kain et al., "Retraction: Odour Receptors and Neurons for DEET and New Insect Repellents", Nature, vol. 536, 2016, p. No. 488.

Kao et al., "The Biochemical Basis for the Anti-inflammatory and Cytoprotective Actions of Ethyl Pyruvate and Related Compounds", Biochemical Pharmacology, vol. 80, 2010, pp. 151-159.

Karatzoglou et al., "Support Vector Machines in R", Journal of Statistical Software, vol. 15, No. 9, Apr. 2006, pp. 1-28.

Katritzky et al., "Synthesis and Bioassay of Improved Mosquito Repellents Predicted from Chemical Structure", PNAS, vol. 105, No. 21, May 27, 2008, pp. 7359-7364.

Kellogg, F. E., "Water vapour and carbon dioxide receptors in Aedes Aegypti", J. Insect Physiol, vol. 16, No. 1, 1970, pp. 99-108.

Kline et al., "Olfactometric Evaluation of Spatial Repellents for *Aedes aegypti*", Journal of Medical Entomology, vol. 40, No. 4, Jul. 2003, pp. 463-467.

(56) References Cited

OTHER PUBLICATIONS

Klocke et al., "1, 8-Cineole (Eucalyptol), A Mosquito Feeding and Ovipositional Repellent from Volatile Oil of Hemizonia Fitchii (Asteraceae)", Journal of Chemical Ecology, vol. 13, No. 12, 1987, pp. 2131-2141.
Klun et al., "Comparative Resistance of Anopheles Albimanus and Aedes aegypti to N,N-Diethyl-3-Methylbenzamide (Deet) and 2-Methylpiperidinyl-3- Cyclohexen-1-Carboxamide (Al3-37220) in Laboratory Human-Volunteer Repellent Assays", Journal of Medical Entomology, vol. 41, No. 3, May 2004, pp. 418-422.
Knecht et al., "Distinct Combinations of Variant Ionotropic Glutamate Receptors Mediate Thermosensation and Hygrosensation in *Drosophila*", Elife, vol. 5, 2016, pp. 1-15.
Kovalenko et al., "Repellent properties of Mannich Bases Derived from Hydroxy- and Aminobenzoic Acid Esters", Database Accession No. 1983:535492, 1983, 2 pages (English Abstract Submitted).
Krajick, K., "Medical Entomology. Keeping the Bugs at Bay", Science, vol. 313, No. 5783, Jul. 7, 2006, pp. 36-38.
Krzywinski et al., "Analysis of the Complete Mitochondrial DNA from Anopheles Funestus: An Improved Dipteran Mitochondrial Genome Annotation and a Temporal Dimension of Mosquito Evolution", Molecular Phylogenetics and Evolution, vol. 39, No. 2, 2006, pp. 417-423.
Lacey et al., "Activation, Orientation and Landing of female Culex Quinquefasciatus in Response to Carbon Dioxide and Odour from Human Feet: 3-D Flight Analysis in a Wind Tunnel", Medical Veterinary Entomology, vol. 25, 2011, pp. 94-103.
Leal et al., "Medicinal Alkaloid as a Sex Pheromone", Nature, vol. 385, Jan. 16, 1997, p. 213.
Lee et al., "Avoiding DEET through Insect Gustatory Receptors", Neuron, vol. 67, No. 4, Aug. 26, 2010, pp. 555-561.
Lee et al., "Multiple Gustatory Receptors Required for the Caffeine Response in *Drosophila*", Proceedings of the National Academy of Sciences, vol. 106, No. 11, Mar. 17, 2009, pp. 4495-4500.
Linduska et al., "Flea Repellents for Use on Clothing", Journal of Economic Entomology, vol. 39, No. 6, Dec. 1946, pp. 767-769.
Liu et al., "Distinct Olfactory Signaling Mechanisms in the Malaria Vector Mosquito *Anopheles gambiae*", Plos Biology, vol. 8, No. 8, e1000467, Aug. 2010, pp. 1-7.
Lu et al., "Odor Coding in the Maxillary Palp of the Malaria Vector *Anopheles gambiae*", Current Biology, vol. 17, No. 18, Sep. 18, 2007, pp. 1533-1544.
Lyne et al., "Identification of Compounds with Nanomolar Binding Affinity for Checkpoint Kinase-1 using Knowledge-based Virtual Screening", Journal of Medicinal Chemistry, vol. 47. No. 8, 2004, pp. 1962-1968.
MacKay et al., "The *Drosophila melanogaster* Genetic Reference Panel", Nature, vol. 482, Feb. 9, 2012, pp. 173-178.
Maldonado et al., "Molecular Similarity and Diversity in Chemoinformatics: From Theory to Applications", Molecular Diversity, vol. 10, 2006, pp. 39-79.
Mann et al., "Sulfur Volatiles from *Allium* Spp. affect Asian Citrus Psyllid, Diaphorina Citri Kuwayama (Hemiptera: Psyllidae), Response to Citrus Volatiles", Bulletin of Entomological Research, vol. 101, No. 1, Feb. 2011, pp. 89-97.
Masuyama et al., "Mapping Neural Circuits with Activity-Dependent Nuclear Import of a Transcription Factor", J. Neurogenetics, vol. 26, 2012, pp. 89-102.
Mayer et al., "Field Evaluation of Non-Pesticide Chemicals as Honey Bee Repellents", Chemical Abstracts Service, Columbus, Ohio, US; 2001, XP002744301, Database Accession No. 2001:493021, 2 pages. (English Abstract Submitted).
Mboera et al., "The rRsponse of Culex Quinquefasciatus (Diptera: Culicidae) to Traps Bbaited with Carbon Dioxide, 1-Octen-3-ol, Acetone, Butyric Acid and Human Foot Odour in Tanzania", Bulletin Entomological Research, vol. 90, No. 2, 2000, pp. 155-159.
Meijerink et al., "Identification of Olfactory Stimulants for Anopheles Gambiae from Human Sweat Samples", Journal of Chemical Ecology, vol. 26, No. 6, 2000, pp. 1367-1382.
Mumcuoglu et al., "Repellency of Essential Oils and their Components to the Human Body Louse, Pediculus Humanus Humanus", Entomologia Experimentalis et Applicata, vol. 78, 1996, pp. 309-314.
Nikonov et al., "A Photoaffinity-Labeled Green Leaf Volatile Compound 'Tricks' Highly Selective and Sensitive Insect Olfactory Receptor Neurons", Chem. Senses, vol. 26, 2001, pp. 49-54.
Njiru et al., "Trapping of the Malaria Vector Anopheles Gambiae with Odour-Baited MM-X Traps in Semi-field Conditions in Western Kenya", Malaria Journal, vol. 5, No. 39, 2006, pp. 1-8.
Non-Final Office Action received for U.S. Appl. No. 12/398,164, dated Aug. 12, 2013, 12 pages.
Non-Final Office Action received for U.S. Appl. No. 12/398,164, dated Jun. 23, 2011, 10 pages.
Non-Final Office Action received for U.S. Appl. No. 13/641,065, dated Aug. 15, 2014, 9 pages.
Non-Final Office Action received for U.S. Appl. No. 14/853,710, dated Feb. 16, 2017, 9 pages.
Notice of Allowance received for U.S. Appl. No. 12/398,164, dated Sep. 26, 2014, 11 pages.
Notice of Allowance received for U.S. Appl. No. 14/352,483, dated Jul. 1, 2016, 7 pages.
Notice of Allowance received for U.S. Appl. No. 14/540,908, dated Dec. 4, 2015, 8 pages,
"Organic Synthesis, vol. III", E.C.Horning, Science Press, Aug. 31, 1981. (See Communication under 37 CFR § 1.98(a) (3)).
Paluch et al., "Mosquito Repellents: A Review of Chemical Structural Diversity and Olfaction", Pest Manag Sci, vol. 66, 2010, pp. 925-935.
Patt et al., "Responses of the Asian Citrus Psyllid to Volatiles Emitted by the Flushing Shoots of Its Rutaceous Host Plants", Environmental Entomology, vol. 39, No. 2, Apr. 2010, pp. 618-624.
Pellegrino et al., "A Natural Polymorphism Alters Odour and DEET Sensitivity in an Insect Odorant Receptor", Nature, vol. 478, No. 7370, Sep. 21, 2011, pp. 511-514.
Pitts et al., "Transcriptome Profiling of Chemosensory Appendages in the Malaria Vector Anopheles Gambiae Reveals Tissue- and Sex-Specific Signatures of Odor Coding", BMC Genomics, vol. 12, vol. 271, 2011, pp. 1-17.
Praag et al., "Steam Volatile Aroma Constituents of Roasted Cocoa Beans", Journal of Agricultural and Food Chemistry, vol. 16, No. 6, Nov.-Dec. 1968, pp. 1005-1008.
Pub, Chem, "(Pentyl-2 Aminobenzoate, Mar. 26, 2005 CID 100495", Available at : <https://pubchem.ncbi.nlm.nih.gov/compound/100495#section=Top>.
Qiu et al., "Attractiveness of MM-X Traps Baited with Human or Synthetic Odor to Mosquitoes (Diptera: Culicidae) in the Gambia", Journal of Medical Entomology, vol. 44, No. 6, Nov. 2007, pp. 970-983.
Qiu et al., "Olfactory Coding in Antennal Neurons of the Malaria Mosquito, *Anopheles gambiae*", Chem. Senses, vol. 31, 2006, pp. 845-863.
Ràmia et al., "PopDrowser: the Population *Drosophila* Browser", Bioinformatics, vol. 28, No. 4, 2012, pp. 595-596.
Ramirez et al., "Repellents Inhibit P450 Enzymes in Stegomyia (Aedes) Aegypti", Plos One, vol. 7, No. 11, Nov. 2012, pp. 1-8.
Reeder, "Isolation of a Deet-Insensitive Mutant of *Drosophila melanogaster* (Diptera: Drosophilidae)", Journal of Economic Entomology, vol. 94, No. 6, Dec. 2001, pp. 1584-1588.
Rehr et al., "L-Dopa in Legume Seeds: A Chemical Barrier to Insect Attack", Science, vol. 181, Jul. 6, 1973, pp. 81-82.
Restriction Requirement received for U.S. Appl. No. 14/853,710, dated Oct. 31, 2016, 10 pages.
Robertson et al., "Evolution of the Gene Lineage Encoding the Carbon Dioxide Receptor in Insects", Journal of Insect Science, vol. 9, No. 19, 2009, pp. 1-14.
Saito et al., "Odor Coding by a Mammalian Receptor Repertoire", Science Signaling, vol. 2, No. 60, Mar. 3, 2009, 28 pages.
Schmuker et al., "Predicting Olfactory Receptor Neuron Responses from Odorant Structure", Chemistry Central Journal, vol. 1, No. 11, 2007, pp. 1-10.
Scognamiglio, "Fragrance Material Review on Cyclopentanone", Food and Chemical Toxicology, vol. 50, 2012, pp. S608-S612.

(56) References Cited

OTHER PUBLICATIONS

Silbering et al., "Complementary Function and Integrated Wiring of the Evolutionarily Distinct *Drosophila* Olfactory Subsystems", The Journal of Neuroscience, vol. 31, No. 38, Sep. 21, 2011, pp. 13357-13375.
Silbering et al., "Ir40a Neurons are not DEET Detectors", Nature, vol. 534, Jun. 23, 2016, pp. E5-E7.
Singer, Allen N., "Topical Hazard Evaluation Program of Candidate Insect", Database accession No. 1980:141441, 1979, 2 pages (English Abstract Submitted).
Skinner et al., "Topical Mosquito Repellents IX: Quinolines, Isoquinolines, and Quinoxalines", Journal of Pharmaceutical Sciences, vol. 65, No. 9, Sep. 1976, pp. 1404-1407.
Smagghe et al., "Insect Cell Culture and Applications to Research and Pest Management", In Vitro Cellular & Developmental Biology—Animal, vol. 45, 2009, pp. 93-105.
Smallegange et al., "Effectiveness of Synthetic Versus Natural Human Volatiles as Attractants for Anopheles Gambiae (Diptera: Culicidae) Sensu Stricto", Journal of Medical Entomology, vol. 47, No. 3, May 2010, pp. 338-344.
Smallegange et al., "Host-seeking Behaviour of Mosquitoes: Responses to Olfactory Stimuli in the Laboratory", Olfaction in Vector-Host Interactions, Ch. 7, 2010, pp. 143-180.
Smallegange et al., "Synergism Between Ammonia, Lactic Acid and Carboxylic Acids as Kairomones in the Host-seeking Behaviour of the Malaria Mosquito *Anopheles gambiae* Sensu Stricto (Diptera: Culicidae)", Chem. Senses, vol. 30, No. 2, 2005, pp. 145-152.
Smith et al., "Effectiveness of Repellents Applied to Clothing for Protection against Salt-Marsh Mosquitoes", Journal of Economic Entomology, vol. 42, 1949, pp. 439-444. (English Abstract Submitted).
Stanczyk et al., "Behavioral Insensitivity to DEET in Aedes Aegypti is a Genetically Determined Trait Residing in Changes in Sensillum Function", PNAS, vol. 107, No. 19, May 11, 2010, pp. 8575-8580.
Su et al., "Non-Synaptic Inhibition between Grouped Neurons in an Olfactory Circuit", Nature, vol. 492, No. 7427, Dec. 6, 2012, pp. 66-71.
Svirbely et al., "Physical Properties of Some Organic Insect Repellents", Journal of the American Chemical Society, vol. 71, Feb. 1949, pp. 507-509.
Sweeney et al., "Targeted Expression of Tetanus Toxin Light Chain in *Drosophila* Specifically Eliminated Synaptic Transmission and Causes Behavioral Defects", Neuron, vol. 14, Feb. 1995, pp. 341-351.
Syed et al., "Acute Olfactory Response of Culex Mosquitoes to a Human- and Bird-Derived Attractant", PNAS, vol. 106, No. 44, Nov. 3, 2009, pp. 18803-18808.
Syed et al., "Generic Insect Repellent Detector from the Fruit Fly *Drosophila melanogaster*", Plos One, vol. 6, No. 3, 2011, pp. 1-6.
Syed et al., "Maxillary Palps Are Broad Spectrum Odorant Detectors in Culex Quinquefasciatus", Chem. Senses, vol. 32, 2007, pp. 727-738.
Syed et al., "Mosquitoes Smell and Avoid the Insect Repellent DEET", PNAS, vol. 105, No. 36, Sep. 9, 2008, pp. 13598-13603.
Tanaka et al., "Allyl Derivatives as Cockroach Repellents", Chemical Abstracts Service, Columbus, Ohio, US; Aug. 20, 1975 (Aug. 20, 1975),XP0027 44424, retrieved from STN Database Accession No. 1976:70350 ; & JP S50 105821 A (TAISHO Pharmaceutical Co., I to., Japan; Takasag Perfumery Co.,LTO.) Aug. 20, 1975. (English Abstract Submitted).
Tanaka et al., "Highly Selective Tuning of a Silkworm Olfactory Receptor to a Key Mulberry Leaf Volatile", Current Biology, vol. 19, No. 11, Jun. 9, 2009, pp. 881-890.
Tentschert et al., "2,3-Dimethyl-5-(2-Methylpropyl)Pyrazine, A Trail Pheromone Component of Eutetramorium Mocquerysi Emery (1899) (Hymenoptera: Formicidae)", Naturwissenschaften, vol. 87, 2000, pp. 377-380.
Turner et al., "Modification of $CO_2$ Avoidance Behaviour in *Drosophila* by Inhibitory Odorants", Nature, vol. 461, Sep. 2009, pp. 277-281.
Turner et al., "Ultra-Prolonged Activation of $CO_2$-Sensing Neurons Disorients Mosquitoes", Nature, vol. 474, No. 7349, Jun. 2, 2011, pp. 87-91.
Verhulst et al., "Chemical Ecology of Interactions Between Human Skin Microbiota and Mosquitoes", FEMS Microbiol Ecol, vol. 74, 2010, pp. 1-9.
Verhulst et al., "Differential Attraction of Malaria Mosquitoes to Volatile Blends Produced by Human Skin Bacteria", PLoS One, vol. 5, No. 12, e15829, Dec. 2010, pp. 1-9.
Viktorov-Nabokov et al., "Effect of Substituents in a Series of Benzoic Acid Esters and Amides on Repellence with Respect to Blood-Sucking Mosquitoes", Fiziologicheski Aktivnye Veshchestva, vol. 12, 1980, 1 page (Abstract only).
Walker et al., "Quantitative Structure-Activity Relationships for Predicting Percutaneous Absorption Rates", Environmental Toxicology and Chemistry, vol. 22, No. 8, 2003, pp. 1870-1884.
Wang et al., "Molecular Basis of Odor Coding in the Malaria Vector Mosquito *Anopheles gambiae*", PNAS, vol. 107, No. 9, Mar. 2, 2010, pp. 4418-4423.
Wang et al., "QSAR Study of Mosquito Repellents from Terpenoid with a Six-Member-Ring", Bioorganic & Medicinal Chemistry Letters, vol. 18, 2008, pp. 2854-2859.
Weeks et al., "Topical Hazard Evaluation Program of Candidate Insect Repellent Al3-36706 Pentyl 2-Aminobenzoate", Database Accession No. 1978:1227, Study No. 51-0847-77, Dec. 1977, 13 pages. (English Abstract Submitted).
Weiss et al., "The Molecular and Cellular Basis of Bitter Taste in *Drosophila*", Neuron, vol. 69, No. 2, Jan. 27, 2011, pp. 258-272.
Whitney, A. W.., "A Direct Method of Nonparametric Measurement Selection", IEEE Transactions on Computers, vol. 20, No. 9, Sep. 1971, pp. 1100-1103.
Xia et al., "The Molecular and Cellular Basis of Olfactory-Driven Behavior in Anopheles Gambiae Larvae", PNAS, vol. 105, No. 17, Apr. 29, 2008, pp. 6433-6438.
Xu et al., "Mosquito Odorant Receptor for DEET and Methyl Jasmonate", Proceedings of the National Academy of Sciences, vol. 111, No. 46, Nov. 18, 2014, pp. 16592-16597.
Xue et al., "Field Evaluation of CDC and Mosquito Magnet X Traps Baited with Dry Ice, $CO_2$ Sachet, and Octenol against Mosquitoes", Journal of the American Mosquito Control Association, vol. 24, No. 2, Jun. 2008, pp. 249-252.
Zhu, Song-Nian, "Research on a Repellent for Ants and Rats for Plastics", Chemical Abstracts Service, Columbus, Ohio, US; 2004, XP002744300, Database Accession No. 2004:1027260. (English Abstract Submitted).
Zwiebel et al., "Olfactory regulation of mosquito-host interactions", Insect Biochem Mol Biol. vol. 34, No. 7, 2004, pp. 645-652.

butyraldehyde butyric acid butyryl chloride

FIG. 6

METHODS FOR IDENTIFYING ARTHROPOD REPELLENTS AND ATTRACTANTS, AND COMPOUNDS AND COMPOSITIONS IDENTIFIED BY SUCH METHODS

CROSS-REFERENCE TO RELATED APPLICATIONS

This application is a continuation application of U.S. patent application Ser. No. 14/855,024, filed Sep. 15, 2015, which is a continuation application of International Application PCT/US14/029201, with an international filing date of Mar. 14, 2014, which claims priority to and the benefit of U.S. Provisional Patent Application No. 61/799,734, filed Mar. 15, 2013, the disclosures of which are incorporated herein by reference in their entireties.

STATEMENT OF RIGHTS TO INVENTIONS MADE UNDER FEDERALLY SPONSORED RESEARCH

This invention was made with government support under Contract 1R01-Ai087785awarded by the National Institutes of Health (NIH). The government has certain rights in the invention.

FIELD

The present disclosure relates generally to the field of arthropod repellents and attractants, and more specifically to methods of identifying such repellents based on affecting the detection of human skin odors in arthropods.

BACKGROUND

Blood-feeding insects, such as mosquitoes, transmit deadly pathogens like malaria parasites, dengue viruses, and filarial worms to hundreds of millions of people every year. Insect repellents can be very effective in reducing vectorial capacity by blocking the contact between blood-seeking insects and humans; however, they are seldom used in disease-prone areas of Africa and Asia due to high costs and need for continuous application on skin.

N,N-Diethyl-m-toluamide (DEET) is an example of an insect repellent used in the developed world for more than sixty years. The use of DEET as an insect repellent, however, has several drawbacks. For example, DEET is a solvent capable of melting several forms of plastics, synthetic fabrics, painted and varnished surfaces (Krajick et al., *Science*, 313: 36, 2006). Additionally, DEET has been shown to inhibit mammalian cation channels and human acetylcholinesterase, which is also inhibited by carbamate insecticides commonly used in disease endemic areas (Corbel et al., *BMC Biol*, 7, 2009). These concerns are enhanced by the requirement of direct and continuous application of DEET to every part of exposed skin in concentrations that can be as high as 30-100%. Several instances of increased resistance to DEET have also been reported in flies, *Anopheles albimanus*, and *Aedes aegypti* (Reeder et al., *J Econ Entomol*, 94: 1584, 2001; Klun et al., *J Med Entomol*, 41: 418, 2004; Stanczyk et al., *Proc Natl Acad Sci USA*, 107: 8575, 2010). Moreover, mosquito strains with resistance to pyrethroid insecticides, the main line of defense against mosquitoes in developing countries, are spreading (Butler et al., *Nature*, 475: 19, 2011). The other major barrier in developing new repellents is the time and cost of development, which can take more than $30 million and several years to identify new compounds that not only repellent to insects, but are also safe for human use.

Thus, what is needed in the art are alternative compounds to DEET that can be used as insect repellents but are safe for human use, and methods of identifying such alternatives.

BRIEF SUMMARY

In one aspect, provided is a method for identifying a compound that is a repellent for at least one arthropod species, by
 a) providing a candidate compound and a skin odor;
 b) providing a sample that includes a neuron, wherein the neuron expresses at least one of Gr1, Gr2, and Gr3 or any orthologs thereof;
 c) contacting the candidate compound with the sample;
 d) measuring the detection of the skin odor by the neuron;
 e) comparing the detection of the skin odor by the neuron after contact with the candidate compound to the detection of the skin odor by the neuron in the absence of the candidate compound; and
 f) identifying a compound that is a repellent for at least one arthropod species by determining whether or not the candidate compound masks or inhibits the detection of the skin odor by the neuron.

In some embodiments, the neuron expresses at least one of AgGr22, AgGr23, and AgGr24 in *Anopheles gambiae* (also called Gr1, Gr2 and Gr3), or any insect orthologs thereof. In some embodiments, the skin odor is an individual odorant or the skin odor comprises a plurality of odorants. In one embodiment, the neuron is a cpA neuron in maxillary palps of mosquitoes. In certain embodiments, the neuron is from an arthropod. In certain embodiments, the neuron is from an insect.

In some embodiments, the compound that is a repellent for at least one arthropod species is identified by determining whether or not the candidate compound masks or inhibits at least 75% of the detection of the skin odor by the neuron. In certain embodiments, the compound is identified in an in vitro assay or in vivo assay. In some embodiments, the activity of the neuron is measured by one or more electrophysiological parameters, one or more activity imaging parameters, or any combinations thereof.

Provided herein is also a composition that includes one or more compound identified according to any of the methods described above.

Provided is also a system that includes:
 a) a sample comprising a neuron, wherein the neuron expresses at least one of Gr1, Gr2, and Gr3, or any orthologs thereof;
 b) a skin odor; and
 c) one or more compounds that each is a repellent for at least one arthropod species, wherein the one or more compounds each masks or inhibits the detection of the skin odor by the neuron during or after exposure to the one or more compounds.

In some embodiments, the skin odor is an individual odorant or the skin odor comprises a plurality of odors. In some embodiments, the neuron is a cpA neuron. In certain embodiments, the neuron is from an arthropod. In certain embodiments, the neuron is from an insect. In some embodiments, the one or more compounds each masks or inhibits at least 75% of the detection of the skin odor by the neuron.

Provided is also a composition for use as an arthropod repellent, that includes two or more compounds selected from the compounds of formulae (Ia), (Va) and (III):

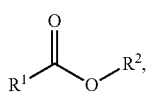

(Ia)

wherein:

$R^1$ and $R^2$ are each independently selected from the group consisting H, OH, SH, an optionally substituted aliphatic or hetero-aliphatic group having 1 to 6 carbon atoms, and a cyclic group having 4 to 8 ring carbon atoms; or $R^1$ and $R^2$ can be linked together to form an optionally substituted aliphatic, heteroaliphatic, aromatic or heteroaromatic ring system having 3 to 6 ring carbon atoms,

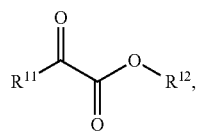

(Va)

wherein:

$R^{11}$ and $R^{12}$ are each independently selected from the group consisting of H, OH, SH, and an optionally substituted aliphatic or hetero-aliphatic group having 1 to 4 carbon atoms; or $R^{11}$ and $R^{12}$ can be linked together to form an optionally substituted aliphatic, heteroaliphatic, aromatic or heteroaromatic ring system having 4 to 6 ring carbon atoms,

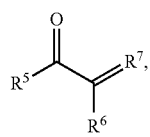

(III)

wherein:

$R^5$ and $R^6$ are each independently selected from the group consisting of H, D, a halide, and optionally substituted aliphatic group; and $R^7$ is selected from the group consisting of an optionally substituted aliphatic group; or $R^5$ and $R^6$ can be linked together to form an optionally substituted cycloalkyl, cycloalkenyl, cycloalkynyl, aryl, or heterocycle; or $R^6$ and $R^7$ can be linked together to form an optionally substituted ring selected from the group consisting of cycloalkenyl, aryl, and heterocycle, or any combinations thereof.

In some embodiments, the composition includes: i) one or more compounds of formula (Ia); and ii) one or more compounds selected from compounds of formulae (Va) and (III), or any combination thereof.

In certain embodiments, the one or more compounds of formula (Ia) are one or more alkyl 2-oxopropanoates. In one embodiment, the one or more alkyl 2-oxopropanoates are selected from the group consisting of ethyl 2-oxopropanoate and methyl 2-oxopropanoate.

Provided is also a composition for use an arthropod repellent, that includes one or more compounds of formula (XII):

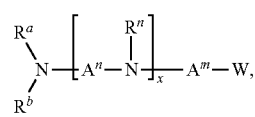

(XII)

wherein:

W is —$NR^cR^d$;

$A^m$ is an aliphatic group;

each $A^n$ is independently an aliphatic group;

each $R^a$, $R^b$, $R^c$ and $R^d$ is independently H or an aliphatic group;

each $R^n$ is independently H or an aliphatic group; and x is an integer greater than or equal to 1;

In some embodiments, x is 0 to 8. In certain embodiments, x is 1 or 2; W is —$NR^cR^d$; each $R^a$, $R^b$, $R^c$, $R^d$, and $R^n$ is H; and each $A^n$ and $A^m$ is independently alkyl.

In one embodiment, the compound is:

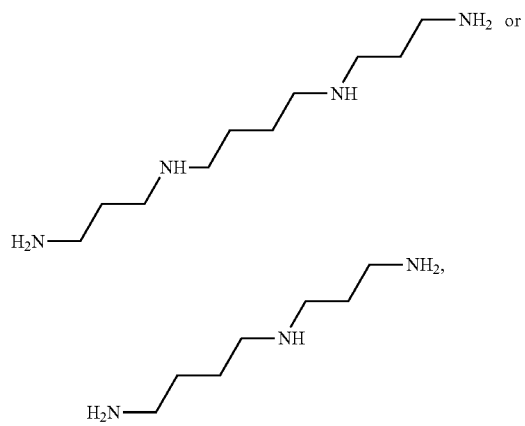

or a combination thereof.

Provided herein is also a composition for use as an arthropod repellent that includes: i) one or more pyruvate inhibitors selected from the compounds of Table A, Group II; and ii) one or more super activators selected from the compound of Table A, Group III.

In some embodiments, the composition is formulated into a lotion, a cream, a spray, a dust, a vaporizer, a treated mat, a treated outerwear, an oil, a candle, or a wicked apparatus.

Provided is also a composition for use as an arthropod attractant, that includes two or more of the compounds of formulae (Ia), (Xb), (Xc), and (XIa):

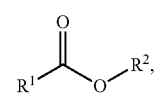

(Ia)

wherein:

$R^1$ and $R^2$ are each independently selected from the group consisting H, OH, SH, an optionally substituted aliphatic or hetero-aliphatic group having 1 to 6 carbon atoms, and a cyclic group having 4 to 8 ring carbon atoms; or $R^1$ and $R^2$ can be linked together to form an optionally substituted aliphatic, heteroaliphatic, aromatic or heteroaromatic ring system having 3 to 6 ring carbon atoms,

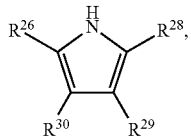

(Xb)

wherein:

$R^{26}$, and $R^{28}$-$R^{30}$ are each independently selected from the group consisting of H, D, a halides, and an optionally substituted aliphatic group; or two or more of $R^{26}$, and $R^{28}$-$R^{30}$ can be linked together to form one or more optionally substituted cycloalkyl, cycloalkenyl, cycloalkynyl, aryl, or heterocycle,

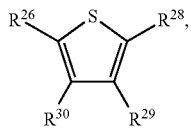

(Xc)

wherein:

$R^{26}$, and $R^{28}$-$R^{30}$ are each independently selected from the group consisting of H, D, a halides, and an optionally substituted aliphatic group; or two or more of $R^{26}$ and $R^{28}$-$R^{30}$ can be linked together to form one or more optionally substituted cycloalkyl, cycloalkenyl, cycloalkynyl, aryl, or heterocycle,

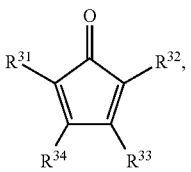

(XIa)

wherein:

$R^{31}$-$R^{34}$ are each independently selected the group consisting of H, D, a halides, and an optionally substituted aliphatic group; and/or two or more of $R^{31}$-$R^{34}$ can be linked together to form one or more optionally substituted cycloalkyl, cycloalkenyl, cycloalkynyl, aryl, or heterocycle, or any combination thereof.

Provided is also a composition for use as an arthropod attractant that includes:

i) one or more compounds selected from thiophene, cyclopentanone, 1H-pyrrole, hex-5-en-2-one, and methyl 2-methylpropanoate; and ii) one or more compounds selected from compounds of formulae (Ia), (Xb), (Xc), and (XIa), or any combination thereof.

In some embodiments, one or more compounds selected from thiophene, 1H-pyrrole, hex-5-en-2-one, and methyl 2-methylpropanoate.

Provided is also a composition for use as an arthropod attractant that includes:

i) a cycloalkanone; and ii) optionally one or more compounds selected from compounds of formulae (Ia), (Xb), (Xc), and (XIa), or any combination thereof In some embodiments, the cycloalkanone is a $C_4$ to $C_6$ cycloalkanone. In one embodiment, the cycloalkanone is cyclopentanone. In another embodiment, the composition includes cyclopentanone and ethyl acetate.

Provided is also a composition for use as an arthropod attractant that includes two or more compounds selected from Table A, Group I. In some embodiments, the composition is used in an arthropod trap. In one embodiment, the arthropod trap is suction-based, light-based, electric current-based, or any combination thereof.

Provided is also a composition comprising a compound identified according to any one of the methods described above.

DESCRIPTION OF THE FIGURES

The present application can be best understood by references to the following description taken in conjunction with the accompanying figures.

Figure 6:
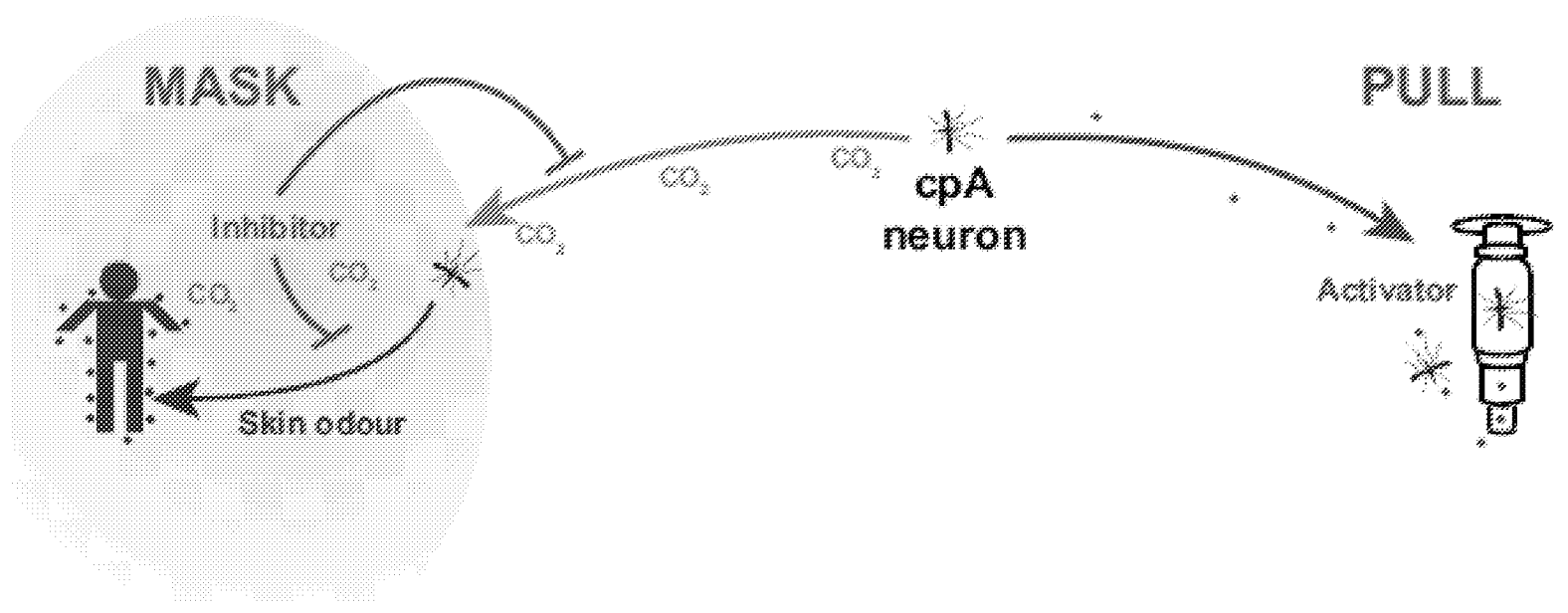

FIG. 6 is an exemplary model for cpA-mediated host-seeking and odorants that disrupt it, in which inhibitors may be used to block attraction to both $CO_2$ and skin odor (MASK) and activators may be used as lures for traps (PULL).

DETAILED DESCRIPTION

Figure 1A:
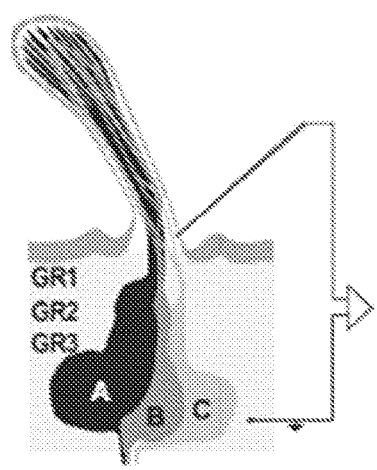
FIG. 1a is schematic of the maxillary palp capitate peg sensillum with three ORNs.
Figure 1B:
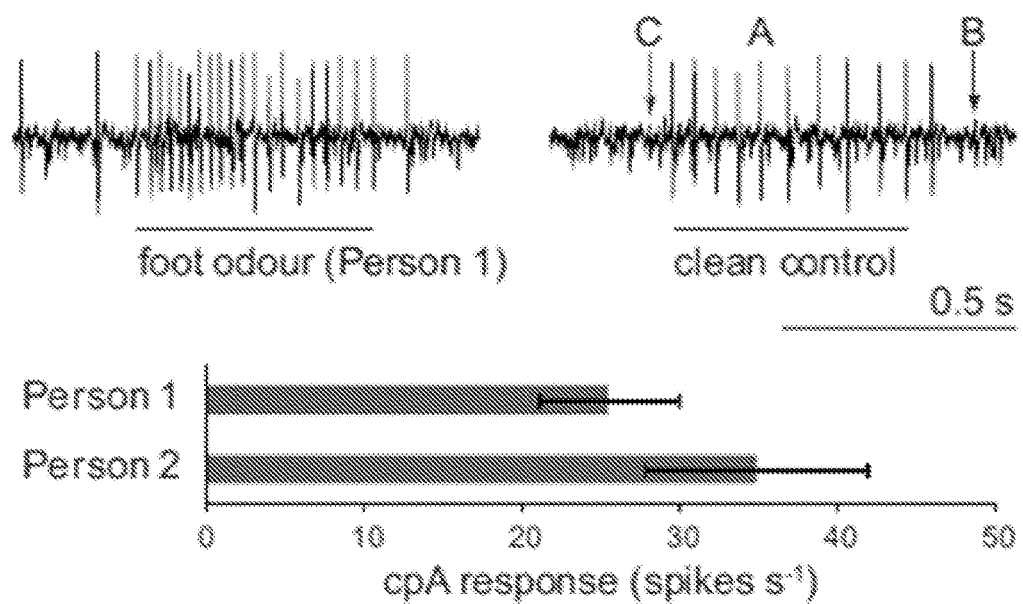
FIG. 1b depicts representative traces and mean change in firing rate of the *Aedes aegypti* cpA (large amplitude that expresses Gr1, Gr2 and Gr3) neuron to a 0.5-s human skin odor stimuli from glass beads laden with foot odor, in which responses to clean-bead controls from the same recording session have been subtracted, and n=6-7.

The following description is presented to enable a person of ordinary skill in the art to make and use the various embodiments. Descriptions of specific materials, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Screening Methods

Provided herein are screening methods for identifying one or more compounds that are repellents for at least one arthropod species. The repellants may mask or inhibit detection of human skin odor by at least one arthropod species. Provided herein are also screening methods for identifying one or more compounds that are attractants for at least one arthropod species.

Arthropods are invertebrate animals characterized as having an exoskeleton, a segmented body, and jointed appendages. Arthropods belong to the Phylum Arthropoda under Kingdom Animalia. The Phylum of Arthropoda, or an "arthropod" includes any invertebrate animal from the Classes of Insecta, Arachnida, Diplopoda, Chilopoda, Crustacea, and Xiphosura. In some embodiments, arthropod may refer to insects and arachnids that are exoparasitic sanguinivorous feeding pests, including any insect from the Order Diptera, such as mosquitoes, and any arachnid from the Order Ixodida, such as ticks. Examples of mosquitoes include *Anopheles, Mimomyia, Culiseta, Orthopodomyia, Mansonia, Culex, Heizmannia, Aedes, Armigeres, Uranotaenia, Tripteroides, Topomyia, Malaya*, and *Toxorhynchite*. As a specific type of such mosquito, an example of the *Anopheles* includes *anopheles sinesis wiedemann*. Examples of the *Culex* include *Culex quinquefasciatus, Culex pipiens pallens, Culex pipiens molestus*, and *Culex tritaeniorhynchus*. Examples of the *Aedes* include *Aedes albopictus* and *Aedes aegypti*. An example of the *Armigeres* includes *Armigeres subalbatus*.

The screening methods can be used to identify one or more arthropod repellents based on masking or inhibiting the detection of the skin odor by a Gr1-, Gr2- and/or Gr3-expressing_neuron (e.g., that may be a cpA neuron). In some embodiments, the method includes: a) providing a candidate compound and a skin odor; b) providing a sample comprising a Gr1-, Gr2- and/or Gr3-expressing_neuron; c) contacting the candidate compound with the sample; d) measuring the detection of the skin odor by the Gr1-, Gr2- and/or Gr3-expressing_neuron; e) comparing the detection of the skin odor by the Gr1-, Gr2- and/or Gr3-expressing_ neuron after contact with the candidate compound to the detection of the skin odor by the Gr1-, Gr2- and/or Gr3-expressing_neuron in the absence of the candidate compound; and f) identifying a compound that is a repellent for at least one arthropod species by determining whether or not the candidate compound masks or inhibits the detection of the skin odor by the Gr1-, Gr2- and/or Gr3-expressing_neuron.

The screening methods can also be used to identify one or more arthropod attractants based on activating a Gr1-, Gr2- and/or Gr3-expressing_neuron.

Candidate Compounds

The screening methods provided herein may be used to screen one candidate compound or a plurality of candidate compounds. The one or more candidate compounds may be natural or synthetic compounds. For example, the one or more candidate compounds may be from bacterial, fungal, plant and animal extracts that are commercially available or readily produced. The one or more candidate compounds can also be chemically-modified compounds, such as by acylation, alkylation, esterification, or acidification of natural compounds. The one or more candidates compounds screened in the methods described herein may be preselected based on one or more criteria. For example, a set of compounds with structural similarities to known insect repellents, like DEET, may be screened and selected for use in the methods described herein. A computation method may be used to select such candidate compounds. Other criteria used for selecting the one or more candidate compounds include the environmental impact of the compounds, regulatory approval of the compounds for human consumption (e.g., FDA-approval), and the smell of the compounds (e.g., natural fragrances, aromas, or odors).

Skin Odor

The skin odor provided with a candidate compound or plurality of candidate compounds, may be an individual odor or a blend of odors. One of skill in the art would recognize that vertebrate odor (e.g., human odor) is a blend of hundreds of volatile chemicals from skin, sweat, and associated microbiota. Odors that can be found in human skin and that activates the Gr1-, Gr2- and/or Gr3-expressing_neuron may include, for example, the compounds in FIG. 1A or any combinations thereof. Vertebrate odor may also include skin odor blend collected from placing an adsorbent or absorbent material in contact with skin, or placed in the headspace above the skin, or a gas passed over the skin, Or skin brought into close vicinity of the cpA.

Gr1-, Gr2- and/or Gr3-Expressing Neuron

The sample provided in the methods described herein may include a Gr1-, Gr2- and/or Gr3-expressing_neuron. The neuron may include three conserved seven-transmembrane domain proteins encoded by members of the gustatory receptor (Gr) gene family (Gr1, Gr2, and/or Gr3 in most mosquitoes, or AgGr22, AgGr23, and AgGr24 in *A. gambiae* (FIG. 1*a*)). Such neuron may be a cpA neuron, which is an olfactory receptor neuron (ORN), housed in specialized capitate peg (cp) sensilla and express the $CO_2$ receptor. In mosquitoes (*Aedes aegypti*), cpA neurons are located in the maxillary palp organs. However, the location of cpA neurons in other arthropod species may vary. The neuron may be activated in response to a vertebrate skin odor. In one embodiment, the sample includes a cell expressing Gr1, Gr2, Gr3, or a combination thereof.

Gr1 Polynucleotides and Polypeptides

In some embodiments, the neurons of the present disclosure may include a Gr1 receptor. Gr1 receptors are known in the art. The Gr1 receptors of the present disclosure may include a Gr1 receptor selected from, for example, *Aedes aegypti, Anopheles gambiae, Culex quinquefasciatus, Bombyx mori, Tribolium castenium, Phlebotomus papatasi, Heliconius melpomene, Manduca sexta,* and *Mayetiola destructor.*

A homolog or an ortholog or any known or putative Gr1 receptor may also be used in the methods and systems described herein. A homolog may be a protein whose nucleic acid sequence that encodes that protein has a similar sequence to the nucleic acid sequence that encodes a known or putative Gr1 receptor, or a protein whose amino acid sequence is similar to the amino acid sequence of a known or putative Gr1 receptor. Gr1 homologs may have functional, structural or genomic similarities to any known or putative Gr1 receptor. One of skill in the art would recognize the techniques that may be employed to clone homologs of a gene, using genetic probes and PCR. Homologs can also be identified by reference to various databases and identity of cloned sequences as homolog can be confirmed using functional assays and/or by genomic mapping of the genes. Additionally, one of skill in the art would understand that an ortholog is an evolutionarily-related polypeptide or polynucleotide sequence in different species that have similar sequences and functions, and that develop through a speciation event.

In some embodiments, a homolog and/or ortholog of a Gr1 receptor is a protein whose nucleic acid sequences have at least 30%, 40%, 50%, 60%, 65%, 70%, 75%, 80%, 85%, 90%, 91%, 92%, 93%, 94%, 95%, 96%, 97%, 98%, or 99% identity to the nucleic acid sequence encoding any known or putative Gr1 receptor. In another embodiment, a homolog of a Gr1 receptor is a protein whose amino acid sequence has at least 30%, 40%, 50% 60%, 65%, 70%, 75%, 80%, 85%, 90%, 91%, 92%, 93%, 94%, 95%, 96%, 97%, 98%, or 99% identity to the amino acid sequence encoding any known or putative Gr1 receptor.

The Gr1 receptor may be from one or more arthropod species. For example, in certain embodiments, the Gr1 receptor is a homolog or ortholog of the Gr1 receptor from *Aedes aegypti*. In some embodiments, the Gr1 receptor has at least 50%, 60%, 65%, 70%, 75%, 80%, 85%, 90%, 91%, 92%, 93%, 94%, 95%, 96%, 97%, 98%, or 99% sequence identity to a polypeptide encoding a Gr1 receptor from *Aedes aegypti*.

One of skill in the art would recognize the methods and techniques that may be employed to determine the percent identity between two amino acid sequences, or between two nucleic acid sequences. One of skill in the art would also recognize that the sequences can be aligned for optimal comparison purposes. For example, gaps can be introduced in one or both of a first and a second amino acid or nucleic acid sequence for optimal alignment and non-homologous sequences can be disregarded for comparison purposes). The amino acid residues or nucleotides at corresponding amino acid positions or nucleotide positions can then be compared. Methods of comparing nucleic acid or amino acid sequences are well-known in the art.

Gr2 Polynucleotides and Polypeptides

In some embodiments, the neurons of the present disclosure may include a Gr2 receptor. Gr2 receptors are known in the art. The Gr2 receptors of the present disclosure may include a Gr2 receptor selected from, for example, *Aedes aegypti, Anopheles gambiae, Culex quinquefasciatus, Bombyx mori, Tribolium castenium, Phlebotomus papatasi, Heliconius melpomene, Manduca sexta,* and *Mayetiola destructor.*

A homolog or an ortholog or any known or putative Gr2 receptor may also be used in the methods and systems described herein. A homolog may be a protein whose nucleic acid sequence that encodes that protein has a similar sequence to the nucleic acid sequence that encodes a known or putative Gr2 receptor, or a protein whose amino acid sequence is similar to the amino acid sequence of a known or putative Gr2 receptor. Gr2 homologs may have functional, structural or genomic similarities to any known or putative Gr2 receptor.

In some embodiments, a homolog and/or ortholog of a Gr2 receptor is a protein whose nucleic acid sequences have at least 30%, 40%, 50% 60%, 65%, 70%, 75%, 80%, 85%, 90%, 91%, 92%, 93%, 94%, 95%, 96%, 97%, 98%, or 99% identity to the nucleic acid sequence encoding any known or putative Gr2 receptor. In another embodiment, a homolog of a Gr2 receptor is a protein whose amino acid sequence has at least 30%, 40%, 50%, 60%, 65%, 70%, 75%, 80%, 85%, 90%, 91%, 92%, 93%, 94%, 95%, 96%, 97%, 98%, or 99% identity to the amino acid sequence encoding any known or putative Gr2 receptor.

The Gr2 receptor may be from one or more arthropod species. For example, in certain embodiments, the Gr2 receptor is a homolog or ortholog of the Gr2 receptor from *Aedes aegypti*. In some embodiments, the Gr2 receptor has at least 50%, 60%, 65%, 70%, 75%, 80%, 85%, 90%, 91%, 92%, 93%, 94%, 95%, 96%, 97%, 98%, or 99% sequence identity to a polypeptide encoding a Gr2 receptor from *Aedes aegypti*.

Gr3 Polynucleotides and Polypeptides

In some embodiments, the neurons of the present disclosure may include a Gr3 receptor. Gr3 receptors are known in the art. The Gr3 receptors of the present disclosure may include a Gr3 receptor selected from, for example, *Aedes aegypti, Anopheles gambiae, Culex quinquefasciatus, Bombyx mori, Tribolium castenium, Phlebotomus papatasi, Heliconius melpomene, Manduca sexta,* and *Mayetiola destructor.*

A homolog or an ortholog or any known or putative Gr3 receptor may also be used in the methods and systems described herein. A homolog may be a protein whose nucleic acid sequence that encodes that protein has a similar sequence to the nucleic acid sequence that encodes a known or putative Gr3 receptor, or a protein whose amino acid sequence is similar to the amino acid sequence of a known or putative Gr3 receptor. Gr3 homologs may have functional, structural or genomic similarities to any known or putative Gr3 receptor.

In some embodiments, a homolog and/or ortholog of a Gr3 receptor is a protein whose nucleic acid sequences have at least 30%, 40%, 50% 60%, 65%, 70%, 75%, 80%, 85%, 90%, 91%, 92%, 93%, 94%, 95%, 96%, 97%, 98%, or 99% identity to the nucleic acid sequence encoding any known or putative Gr3 receptor. In another embodiment, a homolog of a Gr3 receptor is a protein whose amino acid sequence has at least 30%, 40%, 50%, 60%, 65%, 70%, 75%, 80%, 85%, 90%, 91%, 92%, 93%, 94%, 95%, 96%, 97%, 98%, or 99% identity to the amino acid sequence encoding any known or putative Gr3 receptor.

The Gr3 receptor may be from one or more arthropod species. For example, in certain embodiments, the Gr3 receptor is a homolog or ortholog of the Gr3 receptor from *Aedes aegypti*. In some embodiments, the Gr3 receptor has at least 50%, 60%, 65%, 70%, 75%, 80%, 85%, 90%, 91%, 92%, 93%, 94%, 95%, 96%, 97%, 98%, or 99% sequence identity to a polypeptide encoding a Gr3 receptor from *Aedes aegypti*.

Measuring the Detection of Skin Odor

The detection of the skin odor by a Gr1-, Gr2- and/or Gr3-expressing neuron may be measured by any suitable methods and techniques known in the art. Suitable methods and techniques include, for example, measuring electrophysiological parameters. One of skill in the art would recognize that whole organ recordings known as electroantennograms (EAGs) and electropalpograms (EPGs) can be used to detect the aggregate electrical activities from a large number of neurons in response to odors. Another method of detecting skin odor activation is using imaging of neural activity using fluorescent or luminescent reporters of calcium, pH, voltage, and synaptic release.

Identifying Arthropod Repellents

The detection of the skin odor by a Gr1-, Gr2- and/or Gr3-expressing neuron after contact with the candidate compound or plurality of candidate compounds is compared with the detection of the skin odor by a Gr1-, Gr2- and/or Gr3-expressing_neuron in the absence of the candidate compound or plurality of candidate compounds to determine whether a candidate compound is an arthropod repellent.

In some embodiments, a candidate compound is selected as an arthropod repellent based on the ability of the candidate compound to mask the detection of the skin odor by a Gr1-, Gr2- and/or Gr3-expressing_neuron. In certain embodiments, a candidate compound is selected as an arthropod repellent based on at least 75%, 80%, 85%, 90%, 91%, 92%, 93%, 94%, 95%, 96%, 97%, 98% or 99% masking of the detection of the skin odor by a Gr1-, Gr2- and/or Gr3-expressing_neuron.

In other embodiments, a candidate compound is selected as an arthropod repellent based on the ability of the candidate compound to inhibit the detection of the skin odor by the Gr1-, Gr2- and/or Gr3-expressing_neuron. In certain embodiments, a candidate compound is selected as an arthropod repellent based on at least 75%, 80%, 85%, 90%, 91%, 92%, 93%, 94%, 95%, 96%, 97%, 98% or 99% inhibition of the detection of the skin odor by the Gr1-, Gr2- and/or Gr3-expressing_neuron.

Identifying Arthropod Attractants

One or more candidate compounds may be identified as an arthropod attractant based on the activation of the Gr1-, Gr2- and/or Gr3-expressing_neuron. In certain embodiments, a candidate compound is selected as an arthropod attractant based on at least 75%, 80%, 85%, 90%, 91%, 92%, 93%, 94%, 95%, 96%, 97%, 98% or 99% increase in activation of the Gr1-, Gr2- and/or Gr3-expressing_neuron over baseline activity in standard room air.

Screening Systems

Provided herein are also systems used for identifying one or more compounds that are repellents for at least one arthropod species, based on masking or inhibiting the detection of human skin odor by at least one arthropod species.

In some embodiments, the system includes: a) a sample that includes a Gr1-, Gr2- and/or Gr3-expressing_neuron; b) a skin odor; and c) one or more compounds that each is a repellent for at least one arthropod species, wherein the one or more compounds each masks or inhibits the detection of the skin odor by the Gr1-, Gr2- and/or Gr3-expressing_neuron. In certain embodiments, the one or more compounds each masks or inhibits at least 75%, 80%, 85%, 90%, 91%, 92%, 93%, 94%, 95%, 96%, 97%, 98% or 99% of the detection of the skin odor by the Gr1-, Gr2- and/or Gr3-expressing_neuron.

As described above, the skin odor may be an individual odor or the skin odor may be made up of a plurality of odors. In some embodiments, the Gr1-, Gr2- and/or Gr3-expressing_neuron may be from an arthropod or, in certain embodiments, an insect.

Provided herein are also systems used for identifying one or more compounds that are attractants for at least one arthropod species, based activation of the Gr1-, Gr2- and/or Gr3-expressing_neuron. In certain embodiments, a candidate compound is selected as an arthropod attractant based on at least 75%, 80%, 85%, 90%, 91%, 92%, 93%, 94%, 95%, 96%, 97%, 98% or 99% activation of the Gr1-, Gr2- and/or Gr3-expressing_neuron.

Compounds Identified and Compositions Thereof

The following compounds have been identified using the methods and systems described herein to modulate an arthropod olfactory neuron, such as a Gr1-, Gr2- and/or Gr3-expressing neuron. One or more of such compounds may be used in a composition that is an arthropod repellent.

In some embodiments, the compound has a structure of formula (I):

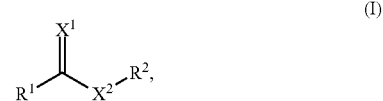

(I)

wherein:

$X^1$ and $X^2$ are each independently selected from the group consisting of O, S and NH;

$R^1$ and $R^2$ are each independently selected from the group consisting of H, D, halide, optionally substituted aliphatic group, and optionally substituted hetero-aliphatic group; or $R^1$ and $R^2$ can be linked together to form an optionally substituted cycloalkyl, cycloalkenyl, cycloalkynyl, aryl, or heterocycle.

In some embodiments of formula (I), when $X^1$ and $X^2$ are each O, and $R^1$ or $R^2$ is methyl, then the other $R^2$ or $R^1$ is H, D, halide, optionally substituted $C_{2+}$ aliphatic group, and optionally substituted hetero-aliphatic group. In certain embodiments of formula (I), when $X^1$ and $X^2$ are each O, $R^1$ and $R^2$ are each other than methyl (i.e., the compound of formula (I) is other than methyl acetate).

In certain embodiments, aliphatic compounds include any non-aromatic compounds, and may be saturated or unsaturated with one or more double or triple bonds. Examples of aliphatic compounds include ($C_1$ to $C_{15}$)alkyls, ($C_1$ to $C_{15}$) alkenyls, ($C_1$ to $C_{15}$)alkynyls, cycloalkyls, cycloalkenyls, and cycloalkynyls. In certain embodiments, hetero-aliphatic groups include any aliphatic compounds in which at least one carbon atom is replaced by a heteroatom, such as nitrogen, oxygen or sulfur. Examples of hetero-aliphatic groups may include ($C_1$ to $C_{14}$)hetero-alkyls, ($C_1$ to $C_{14}$) hetero-alkenyls, and ($C_1$ to $C_{14}$)hetero-alkynyls.

Optionally substituted groups which contain halogens may include, for example, haloalkanes, and haloalkenes. Optionally substituted groups which contain oxygen may include, for example, hydroxyls, carbonyls, aldehydes, haloformyls, carbonate esters, carboxylates, carboxyls, esters, ethers, peroxides, hydroperoxides, hemiacetals, hemiketals, acetals, ketals, orthoesters, and orthocarbonate esters. Optionally substituted groups which contain nitrogen may include, for example, amides, amines, imines, enamines, imides, azides, azo compounds, cyanates, nitrates, nitros, nitriles, nitrosos, and pyridyls. Optionally substituted groups which contain sulfur may include, for example, thiols, sulfides, disulfides, sulfoxides, sulfones, sulfinos, sulfos, thiocyanates, thiones, and thials. Optionally substituted groups which contain phosphorus may include, for example, phosphinos, phosphonos, and phosphates; optionally substituted groups which contain boron, such as boronos, boronates, borinos, and borinates. Optionally substituted groups which contain silicon may include, for example, silyl ethers, silicates, siloxanes, and silanes.

In one embodiment, the compound has a structure of formula (Ia):

(Ia)

wherein:

$R^1$ and $R^2$ are each independently selected from the group consisting H, OH, SH, an optionally substituted aliphatic or hetero-aliphatic group having 1 to 6 carbon atoms, and a cyclic group having 4 to 8 ring carbon atoms; or $R^1$ and $R^2$ can be linked together to form an optionally substituted aliphatic, heteroaliphatic, aromatic or heteroaromatic ring system having 3 to 6 ring carbon atoms.

The aliphatic or hetero-aliphatic groups may be straight or branched, and saturated or unsaturated.

In some embodiments of formula (Ia), when $R^1$ or $R^2$ is methyl, then the other $R^2$ or $R^1$ is H, D, halide, optionally substituted $C_{2+}$ aliphatic group, and optionally substituted hetero-aliphatic group. In certain embodiments of formula (Ia), when $R^1$ and $R^2$ are each other than methyl (i.e., the compound of formula (Ia) is other than methyl acetate).

In some embodiments of formula (Ia), $R^1$ and $R^2$ are each independently selected from the group consisting of H, OH, SH, an optionally substituted aliphatic or hetero-aliphatic group having 1 to 4 carbon atoms; or $R^1$ and $R^2$ can be linked together to form an optionally substituted aliphatic, heteroaliphatic, aromatic or heteroaromatic ring system having 4 to 6 ring carbon atoms.

In other embodiments of formula (Ia), when $X^1$ and $X^2$ are each O, and $R^2$ is an optionally substituted aliphatic group, then $R^1$ is H, OH, SH, an optionally substituted aliphatic or hetero-aliphatic group having 1 to 6 carbon atoms. In certain embodiments of formula (Ia), when $X^1$ and $X^2$ are each O, $R^2$ is an optionally substituted aliphatic group, and $R^1$ is a cyclic group having 4 to 8 ring carbon atoms, then the cyclic group is other than optionally substituted aryl. In certain embodiments of formula (Ia), when $X^1$ and $X^2$ are each O, $R^2$ is an optionally substituted aliphatic group, and $R^2$ is a cyclic group having 4 to 8 ring carbon atoms, then the cyclic group is other than aryl substituted with an optionally substituted amino group.

In another embodiment, the compound has a structure of formula (Ib):

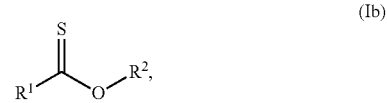

(Ib)

wherein:

$R^1$ and $R^2$ are each independently selected from the group comprising H, OH, SH, an optionally substituted aliphatic or hetero-aliphatic group having 1 to 6 carbon atoms, and a cyclic group having 4 to 8 ring carbon atoms; or $R^1$ and $R^2$ can be linked together to form an optionally substituted aliphatic, heteroaliphatic, aromatic or heteroaromatic ring system having 3 to 6 ring carbon atoms.

In some embodiments of formula (Ib), $R^1$ and $R^2$ are each independently selected from the group consisting of H, OH, SH, and an optionally substituted aliphatic or hetero-aliphatic group having 1 to 4 carbon atoms; or $R^1$ and $R^2$ can be linked together to form an optionally substituted aliphatic, heteroaliphatic, aromatic or heteroaromatic ring system having 4 to 6 ring carbon atoms.

In one embodiment, the compound of formula (I) is selected from methyl propanoate, methyl 2-methylpropanoate, propyl acetate, ethyl acetate, propyl formate, prop-2-enyl-propanoate, 2-methylpropyl formate, methyl butanoate, methyl acetate, methyl propionate, propyl formate, isobutyl formate, methyl isobutyrate, methyl butyrate, ethyl formate, methyl methacrylate, alpha-angelica lactone, allyl propionate, allyl butyrate, dimethyl carbonate, methyl 2-methylprop-2-enoate, ethyl formate, ethyl (E)-but-2-enoate, prop-2-enyl-butanoate, oxolan-2-ylmethyl acetate, benzyl formate, propan-2-yl benzoate, 2-phenylethyl 3-methylbutanoate, [(E)-3-phenylprop-2-enyl]formate, 2-phenylethyl (E)-2-methylbut-2-enoate, 2-(trimethylazaniumyl)acetate, oct-1-en-3-yl butanoate, 2-phenylethyl propanoate, benzyl 3-oxobutanoate, [(2E)-3,7-dimethylocta-2,6-dienyl] formate, 2-methylpropyl-(Z)-but-2-enoate, 2-phenylethyl butanoate, ethyl pyruvate, and methyl pyruvate.

In another embodiment, the compound of formula (I) is selected from 2,2-dimethyl-3-(2-methyl-propenyl)-cyclopropanecarboxylic acid ethyl ester, acetic acid 2,2,6-trimethyl-6-vinyl-tetrahydro-pyran-4-yl ester, isobutyric acid 1-methyl-1-(4-methyl-cyclohex-3-enyl)ethyl ester, acetic acid 2-isopropylidene-4,8-dimethyl-1,2,3,3a,4,5,6,8a-octahydro-azulen-6-yl ester, (4-tert-butyl-phenyl)-acetic acid methyl ester, acetic acid 1-[2-(3,3-dimethyl-oxiranyl)- ethyl]-1-methyl-allyl ester, pentanoic acid 5,5,6-trimethyl-bicyclo[2.2.1]hept-2-yl ester, (1H-indol-2-yl)acetic acid, 6-methyl-2-(3-methyl-cyclohex-3-enyl)-hept-5-en-2-ol, propionic acid 5-isopropenyl-2-methyl-cyclohex-2-enyl ester, 2-hydroxymethyl-but-2-enoic acid 7-(2-methyl-but-2-enoyloxy)-5-,6,7,7a-tetrahydro-3H-pyrrolizin-1-ylmethyl ester, (2-isopropenyl-1-methyl-cyclobutyl)-acetic acid, 7,8-dimethyl-8-aza-bicyclo[3.2.1]octane-2-carboxylic acid methyl ester, acetic acid 2,6,10,10-tetramethyl-1-oxa-spiro [4.5]dec-6-yl ester, isobutyric acid 6,6-dimethyl-bicyclo [3.1.1]hept-2-en-2ylmethyl ester, 4-hydroxy-3,7-dimethyl-octahydro-chromen-2-one, 4,8-dimethyl-octahydro-chromen-2-one, 2-methyl-butyric acid 6,6-dimethyl-bicyclo [3.1.1]hept-2-en-2-ylmethyl ester, 1-(3,8-dimethyl-1,2,3,4, 5,6,7,8-octahydro-azulen-5-yl)-1-methyl-ethyl ester acetic acid, 2-hydroxy-2-(1-methoxy-ethyl)-3-methyl-butyric acid 7-hydroxy-5,6,7,7a-tetrahydro-3H-pyrrolizin-1-ylmethyl ester, carbamic acid ethyl ester, 2-amino-5-guanidino-pentanoic acid, 2-amino-succinamic acid, 2-hydroxy-2-(1-hydroxy-ethyl)-3-methyl-butyric acid 7-hydroxy-5,6,7,7a-tetrahydro-3H-pyrrolizin-1-ylmethyl ester, 4-ethylidene-7-hydroxy-6,7,14-trimethyl-2,9-dioxa-14-aza-bicyclo[9.5.1] heptadec-11-ene-3,8,17-trione, 6-methoxy-3H-benzooxazol-2-one, 2-amino-3-phenyl-propionic acid, phenylalanine, glutamine, mandelonitrile benzoate, 3-Hydroxymethyl-6-methyl-3a,3b,7a,8-tetrahydro-1H-4-oxa-8a-aza-cyclopenta[a]inden-5-one, methyl N-acetylisoleucinate, tryptophan, 2-amino-3-(3,4-dihydroxy-phenyl)-propionic acid, and N-(tert-butyl)-4-methylbenzamide.

In other embodiments, the compound has a structure of formula (II):

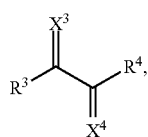

(II)

wherein:

$X^3$ and $X^4$ are each independently selected from the group consisting of O, S and NH;

$R^3$ and $R^4$ are each independently selected from the group consisting of H, D, a halide, and optionally substituted aliphatic groups, or $R^3$ and $R^4$ can be linked together to form an optionally substituted cycloalkyl, cycloalkenyl, cycloalkynyl, aryl, or heterocycle.

In one embodiment, the compound has a structure of formula (IIa):

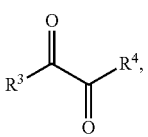

(IIa)

wherein:

$R^3$ and $R^4$ are each independently selected from the group consisting of H, OH, SH, and an optionally substituted aliphatic or hetero-aliphatic group having 1 to 4 carbon atoms; or $R^3$ and $R^4$ can be linked together to form an optionally substituted cycloalkyl, cycloalkenyl, cycloalkynyl, aryl, or heterocycle.

In one embodiment, the compound of formula (II) is selected from 3-methylcyclopentane-1,2-dione, 3,4-dimethylcyclopentane-1,2-dione, 2-oxopentanoic acid, and 2-oxopropanal.

In other embodiments, the compound has a structure of formula (III):

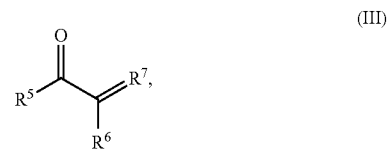

(III)

wherein:

$R^5$ and $R^6$ are each independently selected from the group consisting of H, D, a halide, and optionally substituted aliphatic group; and $R^7$ is selected from the group consisting of an optionally substituted aliphatic group; or $R^5$ and $R^6$ can be linked together to form an optionally substituted cycloalkyl, cycloalkenyl, cycloalkynyl, aryl, or heterocycle; or $R^6$ and $R^7$ can be linked together to form an optionally substituted ring selected from the group consisting of cycloalkenyl, aryl, and heterocycle.

In some embodiments of formula (III), $R^5$-$R^7$ are each independently selected from the group consisting of H, OH, SH, and an optionally substituted aliphatic or hetero-aliphatic group having 1 to 4 carbon atoms. In other embodiment of formula (III), $R^5$ and $R^6$ can be linked together to form an optionally substituted aliphatic, heteroaliphatic, aromatic or heteroaromatic ring system having 4 to 6 ring carbon atoms. In yet other embodiments of formula (III), $R^6$ and $R^7$ can be linked together to form an optionally substituted aliphatic, heteroaliphatic, aromatic or heteroaromatic ring system having 4 to 6 ring carbon atoms.

In one embodiment, the compound of formula (III) is selected from propan-2-yl benzoate, 2-phenylethyl (E)-2-methylbut-2-enoate, 4-ethylbenzaldehyde, (E)-2-methylbut-2-enoic acid, 1-phenylbutan-1-one, (E)-2-methylbut-2-enoic acid, 1-phenylbutan-1-one, 3-methylbut-2-enoic acid, (E)-but-2-enoic acid, 2-methylpropyl-(Z)-but-2-enoate, (E)-pent-2-enal, 3-methylcyclopent-2-en-1-one, methyl 2-methylprop-2-enoate, (2E)-3,7-dimethylocta-2,6-dienoic acid, 1-(1H-pyrrol-2-yl)ethanone, and ethyl (E)-but-2-enoate.

In another embodiment, the compound of formula (III) is selected from N,N-diethyl-4-methyl-benzamide, N-butyl-3-fluoro-benzamide, N-(3-methyl-butyl)-benzamide, N-(tert-butyl)-4-methylbenzamide, 2-carbamoyl-benzoic acid anion, 3-hydroxymethyl-6-methyl-3a,3b,7a,8-tetrahydro-1H-4-oxa-8a-aza-cyclopenta[a]inden-5-one, mandelonitrile benzoate, 7,8-dihydro-1-biopterin, N-(2-formyl-phenyl)-formamide, indolo[2,1-b]quinazoline-6,12-dione, 4-ethylidene-7-hydroxy-6,7,14-trimethyl-2,9-dioxa-14-aza-bicyclo [9.5.1]heptadec-11-ene-3,8,17-trione, [hydroxy-(4-hydroxy-quinolin-2-yl)-methylene]-methyl-oxonium, 1-(2, 6,6-trimethyl-cyclohex-2-enyl)-hepta-1,6-dien-3-one, 4-(1-hydroxy-4,7-dimethyl-1,4a,5,6,7,7a-hexahydro-cyclopenta [c]pyran-3-yl)-but-3-en-2-one, 2-hydroxymethyl-but-2-enoic acid 7-(2-methyl-but-2-enoyloxy)-5,6,7,7a-tetrahydro-3H-pyrrolizin-1-ylmethyl ester, 4-(2,5,6,6-tetramethyl-cyclohex-2-enyl)-but-3-en-2-one, 3-methyl-4-(2,6,6-trimethyl-cyclohex-2-enyl)-but-3-en-2-one, 2-hydroxy-4,4,6-trimethyl-cyclohexa-2,5-dienone, 1-(3,5,5, 6,8,8-hexamethyl-5,6,7,8-tetrahydro-naphthalen-2-yl)-ethanone, 10-isopropylidene-3,7-dimethyl-cyclodeca-3,7-dienone, 3,3,6-trimethyl-hepta-1,5-dien-4-one, and 3,5,5-trimethyl-4-(3-oxo-but-1-enyl)-cyclohex-3-enone.

In other embodiments, the compound has a structure of formula (IV):

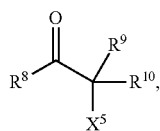

(IV)

Wherein:
X$^5$ is selected from the group consisting of OH, SH, and NH$_2$;
R$^8$, R$^9$ and R$^{10}$ are each independently selected from the group consisting of H, D, a halides, an optionally substituted aliphatic group; or R$^8$ and R$^9$ can be linked together to form an optionally substituted cycloalkyl, cycloalkenyl, cycloalkynyl, aryl, or heterocycle.

In one embodiment, the compound has a structure of formula (IVa):

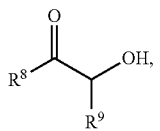

(IVa)

wherein:
R$^8$ and R$^9$ are each independently selected from the group consisting of H, OH, SH, or an optionally substituted aliphatic or hetero-aliphatic group having 1 to 4 carbon atoms; or R$^8$ and R$^9$ can be linked together to form an optionally substituted aliphatic, heteroaliphatic, aromatic or heteroaromatic ring system having 4 to 6 ring carbon atoms.

In one embodiment, the compound of formula (IV) is selected from 4-hydroxy-2,3-dimethyl-2H-furan-5-one, 2-hydroxypropanoic acid, and 3-hydroxybutan-2-one.

In another embodiment, the compound of formula (IV) is selected from 4-ethylidene-7-hydroxy-6,7,14-trimethyl-2,9-dioxa-14-aza-bicyclo[9.5.1]heptadec-11-ene-3,8,17-trione, 2-hydroxy-2-(1-hydroxy-ethyl)-3-methyl-butyric acid 7-hydroxy-5,6,7,7a-tetrahydro-3H-pyrrolizin-1-ylmethyl ester, and 2-hydroxy-2-(1-methoxy-ethyl)-3-methyl-butyric acid 7-hydroxy-5,6,7,7a-tetrahydro-3H-pyrrolizin-1-ylmethyl ester.

In yet other embodiments, the compound has a structure of formula (V):

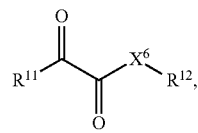

(V)

wherein:
X$^6$ is selected from the group consisting of O, S, and NH;
R$^{11}$ and R$^{12}$ are each independently selected from the group consisting of H, D, a halides, and an optionally substituted aliphatic group; or R$^{11}$ and R$^{12}$ can be linked together to form an optionally substituted cycloalkyl, cycloalkenyl, cycloalkynyl, aryl, or heterocycle.

In certain embodiments, the compound has a structure of formula (Va):

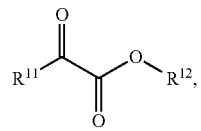

(Va)

wherein:
R$^{11}$ and R$^{12}$ are each independently selected from the group consisting of H, OH, SH, and an optionally substituted aliphatic or hetero-aliphatic group having 1 to 4 carbon atoms; or R$^{11}$ and R$^{12}$ can be linked together to form an optionally substituted aliphatic, heteroaliphatic, aromatic or heteroaromatic ring system having 4 to 6 ring carbon atoms.

In one embodiment, the compound of formula (V) is selected from ethyl 2-oxopropanoate, methyl 2-oxopropanoate, 4-hydroxy-2,3-dimethyl-2H-furan-5-one, and 3-hydroxybutan-2-one, 2-oxobutanoic acid, 2-oxopentanoic acid, ethyl pyruvate, and methyl pyruvate.

In yet other embodiments, the compound has a structure of formula (VI):

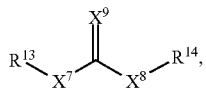

(VI)

wherein:
X$^7$, X$^8$, and X$^9$ are each independently selected from the group consisting of O, S, and NH;
R$^{13}$ and R$^{14}$ are each independently selected from the group consisting of H, D, a halide, and an optionally substituted aliphatic group; or R$^{13}$ and R$^{14}$ can be linked together to form an optionally substituted cycloalkyl, cycloalkenyl, cycloalkynyl, aryl, or heterocycle.

In certain embodiments, the compound has a structure of formula (VIa):

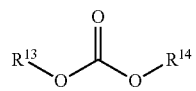

(VIa)

wherein:
R$^{13}$ and R$^{14}$ are each independently selected from the group consisting of H, OH, SH, and an optionally substituted aliphatic or hetero-aliphatic residues having 1 to 4 carbon atoms; or R$^{13}$ and R$^{14}$ can be linked together to form an optionally substituted aliphatic, heteroaliphatic, aromatic or heteroaromatic ring system having 4 to 6 ring carbon atoms.

In one embodiment, the compound of formula (VI) is selected from dimethyl carbonate, 1,3-dimethyl-1H-quinazoline-2,4-dione, 1,3,7-trimethyl-3,7-dihydro-purine-2,6-dione, 5,5-diethyl-pyrimidine-2,4,6-trione, 1,3-dinitro-imidazolidin-2-one, (2,5-dioxo-4-imidazolidinyl) urea, 7,9-dihydro-3H-purine-2,6,8-trione, purine-2,6-dione, 1,3-dimethyl-1H-pyrimidine-2,4-dione, 6-methoxy-3H-benzooxazol-2-one, carbamic acid ethyl ester, 3H-benzothiazol-2-one, 14-nitrooxy-tetradec-5-ene, and 1,2-dihydro-[1,2,4]triazol-3-one.

In yet other embodiments, the compound has a structure of formula (VII):

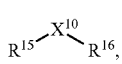
(VII)

wherein:

$X^{10}$ is selected from the group consisting of O, S, and NH;

$R^{15}$ and $R^{16}$ are each independently selected from the group consisting of H, D, a halides, and an optionally substituted aliphatic group; or $R^{15}$ and $R^{16}$ can be linked together to form an optionally substituted cycloalkyl, cycloalkenyl, cycloalkynyl, aryl, or heterocycle.

In certain embodiments, the compound has a structure of formula (VIIa):

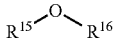
(VIIa)

wherein:

$R^{15}$ and $R^{16}$ are each independently selected from the group consisting of H, OH, SH, or an optionally substituted aliphatic or hetero-aliphatic group having 1 to 4 carbon atoms; or $R^{15}$ and $R^{16}$ can be linked together form an optionally substituted aliphatic, heteroaliphatic, aromatic or heteroaromatic ring system having 4 to 6 ring carbon atoms.

In yet other embodiments, the compound has a structure of formula (VIII):

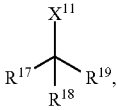
(VIII)

wherein;

$X^{11}$ is selected from the group consisting of OH, SH, and $NH_2$; and $R^{17}$, $R^{18}$, and $R^{19}$ are each independently selected from the group consisting of H, D, a halides, and an optionally substituted aliphatic group; or $R^{18}$ and $R^{19}$ and/or $R^{20}$ can be linked together to form an optionally substituted cycloalkyl, cycloalkenyl, cycloalkynyl, aryl, or heterocycle.

In certain embodiments, the compound has a structure of formula (VIIIa):

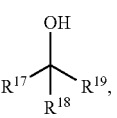
(VIIIa)

wherein:

$R^{17}$, $R^{18}$, and $R^{19}$ are each independently selected from the group consisting of H, OH, SH, or an optionally substituted straight or branched, saturated or unsaturated, aliphatic or hetero-aliphatic residues having 1 to 4 carbon atoms; or two of $R^{17}$, $R^{18}$, and $R^{19}$ can be linked together to form an optionally substituted aliphatic, heteroaliphatic, aromatic or heteroaromatic ring system having 4 to 6 ring carbon atoms.

In yet other embodiments, the compound has a structure of formula (IX):

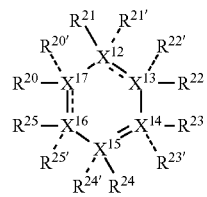
Formula (IX)

wherein, $X^{12}$-$X^{17}$ are each independently selected from the group consisting of C, N, O, and S;

$R^{20}$-$R^{25}$ are each independently selected from the group consisting of H, D, a halide, and an optionally substituted aliphatic group; or two or more of $R^{20}$-$R^{25}$ can be linked together to form one or more optionally substituted cycloalkyl, cycloalkenyl, cycloalkynyl, aryl, or heterocycle; and $R^{20'}$-$R^{25'}$ are each independently selected from the group consisting of H, D, a halides, and an optionally substituted aliphatic group; or two or more of $R^{20'}$-$R^{25'}$ can be linked together to form one or more optionally substituted cycloalkyl, cycloalkenyl, cycloalkynyl, aryl, or heterocycle; and wherein any one of $R^{20}$-$R^{25}$ and/or $R^{20'}$-$R^{25'}$ are absent if by forming a covalent bond to the corresponding X group would result in the X group exceeding the maximum valence for that atom.

In certain embodiments, the compound has a structure of formula (IXa):

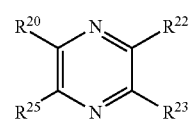
(IXa)

wherein:

$R^{20}$, $R^{22}$, $R^{23}$, and $R^{25}$ are each independently selected from the group consisting of H, D, a halides, and an optionally substituted aliphatic group; or $R^{20}$ and $R^{25}$ can be linked together to form one or more optionally substituted cycloalkyl, cycloalkenyl, cycloalkynyl, aryl, or heterocycle; and/or $R^{22}$ and $R^{23}$ can be linked together to form one or more optionally substituted cycloalkyl, cycloalkenyl, cycloalkynyl, aryl, or heterocycle.

In certain embodiments of formula (IXa), $R^{20}$, $R^{22}$, $R^{23}$, and $R^{25}$ are each independently selected from the group consisting of H, OH, SH, and an optionally substituted aliphatic or hetero-aliphatic group having 1 to 4 carbon atoms. In other embodiments of formula (IXa), $R^{20}$ and $R^{25}$ can be taken together form an optionally substituted aliphatic, heteroaliphatic, aromatic or heteroaromatic ring system having 4 to 6 ring carbon atoms. In yet other embodiments of formula (IXa), $R^{22}$ and $R^{23}$ can be taken together form an optionally substituted aliphatic, heteroaliphatic, aromatic or heteroaromatic ring system having 4 to 6 ring carbon atoms.

In certain embodiments, the compound has a structure of formula (IXb):

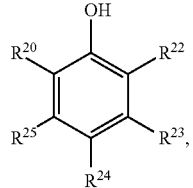

(IXb)

wherein:

$R^{20}$ and $R^{22}$-$R^{25}$ are each independently selected from the group consisting of H, D, a halides, and an optionally substituted aliphatic group; or two or more of $R^{20}$ and $R^{22}$-$R^{25}$ can be linked together to form one or more optionally substituted cycloalkyl, cycloalkenyl, cycloalkynyl, aryl, or heterocycle.

In certain embodiments of formula (IXb), $R^{20}$ and $R^{22}$-$R^{25}$ are each independently selected from the group consisting of H, OH, SH, and an optionally substituted aliphatic or heteroaliphatic groups having 1 to 4 carbon atoms. In other embodiments of formula (IXb), two or more of $R^{20}$ and $R^{22}$-$R^{25}$ can be linked together to form an optionally substituted aliphatic or heteroaliphatic, aromatic or heteroaromatic ring system having 4 to 6 ring carbon atoms.

In certain embodiments, the compound has a structure of formula (IXc):

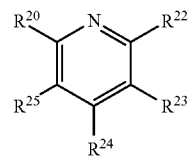

(IXc)

wherein:

$R^{20}$ and $R^{22}$-$R^{25}$ are each independently selected from the group consisting of H, D, a halide, and an optionally substituted aliphatic group; or two or more of $R^{20}$ and $R^{22}$-$R^{25}$ can be linked together to form one or more optionally substituted cycloalkyl, cycloalkenyl, cycloalkynyl, aryl, or heterocycle.

In certain embodiments of formula (IXc), $R^{20}$ and $R^{22}$-$R^{25}$ are each independently selected from the group consisting of H, OH, SH, and an optionally substituted aliphatic or heteroaliphatic group having 1 to 4 carbon atoms. In other embodiments of formula (IXc), two or more of $R^{20}$ and $R^{22}$-$R^{25}$ can be linked together to form an optionally substituted aliphatic, heteroaliphatic, aromatic or heteroaromatic ring system having 4 to 6 ring carbon atoms.

In certain embodiments, the compound has a structure of formula (IXd):

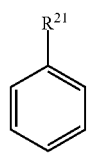

(IXd)

wherein:

$R^{21}$ is selected from the group consisting of H, D, a halides, an optionally substituted aliphatic group.

In yet other embodiments, the compound has a structure of formula (X):

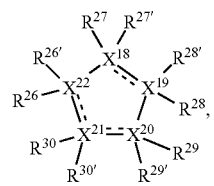

(X)

wherein:

$X^{18}$-$X^{22}$ are each independently selected from the group consisting of C, O, N, and S;

$R^{26}$-$R^{30}$ are each independently selected from the group consisting of H, D, a halides, and an optionally substituted aliphatic group; or two or more of $R^{26}$-$R^{30}$ can be linked together to form one or more optionally substituted cycloalkyl, cycloalkenyl, cycloalkynyl, aryl, or heterocycle; and $R^{26'}$-$R^{30'}$ are each independently selected from the group consisting of H, D, a halides, and an optionally substituted aliphatic group; or two or more R groups from $R^{26'}$-$R^{30'}$ can be linked together to form one or more optionally substituted cycloalkyl, cycloalkenyl, cycloalkynyl, aryl, or heterocycle; and wherein any one of $R^{26}$-$R^{30}$ and/or $R^{26'}$-$R^{30'}$ are absent if by forming a covalent bond to the corresponding X group would result in the X group exceeding the maximum valence for that atom.

In certain embodiments, the compound has a structure of formula (Xa):

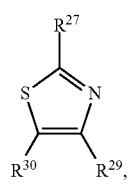

(Xa)

wherein;

$R^{27}$ and $R^{29}$-$R^{30}$ are each independently selected from the group consisting of H, D, a halides, or an optionally substituted aliphatic group; or $R^{29}$-$R^{30}$ can be linked together to form one or more optionally substituted cycloalkyl, cycloalkenyl, cycloalkynyl, aryl, or heterocycle.

In one embodiment of formula (Xa), $R^{27}$ and $R^{29}$-$R^{30}$ are each independently selected from the group consisting of H, OH, SH, and an optionally substituted aliphatic or heteroaliphatic residues having 1 to 4 carbon atoms. In another embodiment of formula (Xa), two of $R^{29}$-$R^{30}$ can be linked together to form an optionally substituted aliphatic, heteroaliphatic, aromatic or heteroaromatic ring system having 4 to 6 ring carbon atoms.

In certain embodiments, the compound has a structure of formula (Xb):

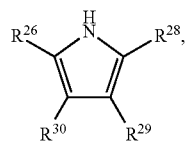

(Xb)

wherein:

$R^{26}$, and $R^{28}$-$R^{30}$ are each independently selected from the group consisting of H, D, a halides, and an optionally substituted aliphatic group; or two or more of $R^{26}$, and $R^{28}$-$R^{30}$ can be linked together to form one or more optionally substituted cycloalkyl, cycloalkenyl, cycloalkynyl, aryl, or heterocycle.

In one embodiment of formula (Xb), $R^{26}$ and $R^{28}$-$R^{30}$ are each independently selected from the group consisting of H, OH, SH, and an optionally substituted aliphatic or heteroaliphatic groups having 1 to 4 carbon atoms. In another embodiment of formula (Xb), two or more of $R^{26}$ and $R^{28}$-$R^{30}$ can be linked together to form an optionally substituted aliphatic, heteroaliphatic, aromatic or heteroaromatic ring system having 4 to 6 carbon atoms.

In certain embodiments, the compound has a structure of formula (Xc):

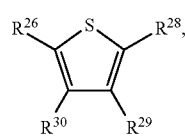

(Xc)

wherein:

$R^{26}$, and $R^{28}$-$R^{30}$ are each independently selected from the group consisting of H, D, a halide, and an optionally substituted aliphatic group; or two or more of $R^{26}$ and $R^{28}$-$R^{30}$ can be linked together to form one or more optionally substituted cycloalkyl, cycloalkenyl, cycloalkynyl, aryl, or heterocycle.

In some embodiments of formula (Xc), $R^{26}$, and $R^{28}$-$R^{30}$ are each independently selected from the group consisting of a halide, or an optionally substituted aliphatic group. In other embodiments of formula (Xc), $R^{26}$, and $R^{28}$-$R^{30}$ are each other than H.

In one embodiment of formula (Xc), $R^{26}$ and $R^{28}$-$R^{30}$ are each independently selected from the group consisting of H, OH, SH, and an optionally substituted aliphatic or heteroaliphatic group having 1 to 4 carbon atoms. In another embodiment of formula (Xc), two or more of $R^{26}$ and $R^{28}$-$R^{30}$ can be linked together to form an optionally substituted aliphatic, heteroaliphatic, aromatic or heteroaromatic ring system having 4 to 6 ring carbon atoms.

In yet other embodiments, the compound has a structure of formula (XI):

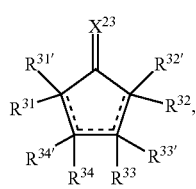

(XI)

wherein:

$X^{23}$ is selected from the group consisting of O, S, NH, and $CH_2$;

$R^{31}$-$R^{34}$ are each independently selected from the group consisting of H, D, a halides, and an optionally substituted aliphatic group; or two or more of $R^{31}$-$R^{34}$ can be linked together to form one or more optionally substituted cycloalkyl, cycloalkenyl, cycloalkynyl, aryl, or heterocycle; and $R^{31'}$-$R^{34'}$ are each independently selected from the group consisting of H, D, a halides, and an optionally substituted aliphatic group; or two or more of $R^{31'}$-$R^{34'}$ can be linked together to form one or more optionally substituted cycloalkyl, cycloalkenyl, cycloalkynyl, aryl, or heterocycle; and wherein any one of $R^{31}$-$R^{34}$ and/or $R^{31'}$-$R^{34'}$ are absent if by forming a covalent bond to the corresponding X group would result in the X group exceeding the maximum valence for that atom.

In certain embodiments, the compound has a structure of formula (XIa):

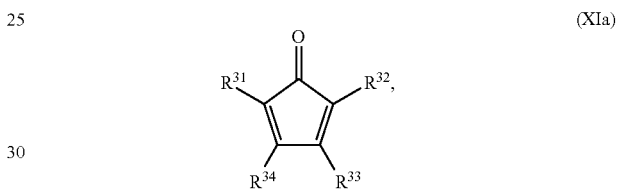

(XIa)

wherein:

$R^{31}$-$R^{34}$ are each independently selected the group consisting of H, D, a halides, and an optionally substituted aliphatic group; and/or two or more of $R^{31}$-$R^{34}$ can be linked together to form one or more optionally substituted cycloalkyl, cycloalkenyl, cycloalkynyl, aryl, or heterocycle.

In one embodiment of formula (XIa), $R^{31}$-$R^{34}$ are each independently selected from the group consisting of H, OH, SH, and an optionally substituted aliphatic or heteroaliphatic group having 1 to 4 carbon atoms. In another embodiment of formula (XIa), two or more of $R^{33}$-$R^{36}$ can be linked together to form an optionally substituted aliphatic or heteroaliphatic, aromatic, heteroaromatic ring system having 4 to 6 ring carbon atoms.

In yet other embodiments, the compound has a structure of formula (XII):

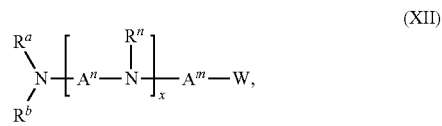

(XII)

wherein:

W is —$NR^cR^d$ or —$CR^cR^dR^e$;

$A^m$ is an aliphatic group;

each $A^n$ is independently an aliphatic group;

each $R^a$, $R^b$, $R^c$, $R^d$ and $R^e$ is independently H or an aliphatic group;

each $R^n$ is independently H or an aliphatic group; and x is an integer greater than or equal to 1;

In some embodiments, W is —$NR^cR^d$.

In some embodiments, x is 0 to 8.

In certain embodiments, the compound of formula (XII) is other than hexan-1-amine.

In some embodiments, $A^m$ is an alkyl. In some embodiments, each $A^n$ is an alkyl. In certain embodiments, $A^m$ is a (C1-C5) alkyl. In certain embodiments, each $A^n$ is a (C1-C5) alkyl.

In one embodiment:

x is 1 or 2;

W is —$NR^cR^d$;

each $R^a$, $R^b$, $R^c$, $R^d$, and $R^n$ is H; and each $A^n$ and $A^m$ is independently alkyl.

In certain embodiments, the compound has a structure of formula (XIIA) or (XIIB):

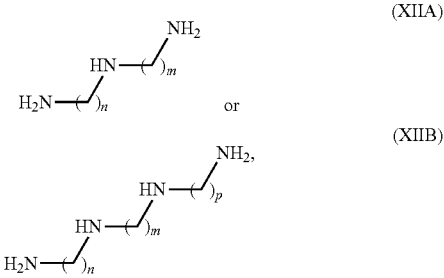

wherein each n, m and p (if present) in independent an integer greater than or equal to 1.

In certain embodiments of formula (XIIA) or (XIIB), n is 1 to 10, or 1 to 8, or 1 to 5. In one embodiment, n is 1, 2, 3, or 4.

In certain embodiments of formula (XIIA) or (XIIB), m is 1 to 10, or 1 to 8, or 1 to 5. In one embodiment, m is 1, 2, 3, or 4.

In certain embodiments of formula (XIIB), p is 1 to 10, or 1 to 8, or 1 to 5. In one embodiment, p is 1, 2, 3, or 4.

In one embodiment, the compound is:

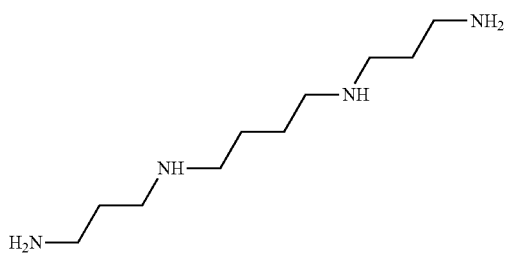 [SMILES: NCCCNCCCCNCCCN]

(spermine) or

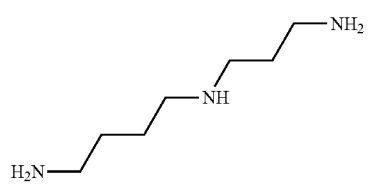

(spermidine).

In yet other embodiments, the compound is:

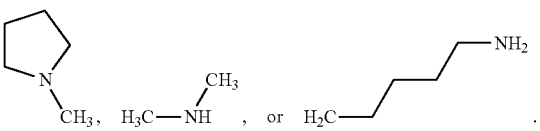

Provided herein are also compositions comprising one or more compounds of formula (I)-(XII). In some embodiments, the composition includes two or more compounds of formula (Ia), (III) and (Va), or any combination thereof. In yet other embodiments, the composition includes two or more compounds of formula (Xb) and (XIa), or any combination thereof.

In yet other embodiments, the compound identified according to the methods and systems described herein are selected from Table A below. Provided are also compositions including one or more, two or more, or three or more compounds selected from Table A below.

TABLE A

| IUPAC | CAS |
|---|---|
| GROUP I | |
| thiophene | 110-02-1 |
| cyclopentanone | 120-92-3 |
| 1H-pyrrole | 109-97-7 |
| furan 3-carbaldehyde | 498-60-2 |
| hex-5-en-2-one | 109-49-9 |
| methyl propanoate | 554-12-1 |
| propane-1-thiol | 107-03-9 |
| methyl 2-methylpropanoate | 547-63-7 |
| propyl acetate | 109-60-4 |
| 3-methylbutan-1-ol | 123-51-3 |
| ethyl acetate | 141-78-6 |
| cyclohexanol | 108-93-0 |
| propyl formate | 110-74-7 |
| 5-methyl-3H-furan-2-one | 591-12-8 |
| 1-methylpyrrole | 96-54-8 |
| pentan-1-ol | 71-41-0 |
| 5-ethenyl-4-methyl-1,3-thiazole | 1759-28-0 |
| prop-2-enyl propanoate | 2408-20-0 |
| 2-methylpropyl formate | 542-55-2 |
| methyl butanoate | 623-42-7 |
| GROUP II | |
| methyl acetate | 79-20-9 |
| methyl 2-oxopropanoate | 600-22-6 |
| ethyl 2-oxopropanoate | 617-35-6 |
| GROUP III | |
| (E)-2-methylbut-2-enal | 497-03-0 |
| (12) 3-methylbut-2-enal | 107-86-8 |
| (127) 3-methylbutanal | 590-86-3 |
| 3-methylbutanal | 590-86-3 |
| (E)-2-methylbut-2-enal | 497-03-0 |
| 3-methylbut-2-enal | 107-86-8 |

Formulations and Modes of Application

The compositions may further include thickeners, buffering agents, chelating agents, preservatives, fragrances, moisturizers, antioxidants, gelling agents, stabilizers, surfactants, emollients, carriers, coloring agents, aloe vera, waxes, lanolins, other penetration enhancers and mixtures thereof, therapeutically or cosmetically active agents, insecticidals, or any combination thereof. In certain embodiments, the composition may be formulated for the topical administration of the composition to the skin of a subject (e.g., a human).

The compositions described herein may be solid-based, liquid-based, gas-based, or a mixture thereof. Liquid-based formulations may be aqueous-based or non-aqueous-based (e.g., organic solvents), or combinations thereof, and may be employed as lotions, ointments, foams, gels, suspensions, emulsions, microemulsions or emulsifiable concentrates or the like. The compositions may also be formulated to be slowly released from a patch or canister.

The compositions described herein may further include one or more carrier formulation agents, including commercially-available organic and inorganic liquid carriers, solid carriers, or semi-solid carriers or carrier formulations. Examples of organic liquid carriers include liquid aliphatic hydrocarbons (e.g., pentane, hexane, heptane, nonane, decane and their analogs) and liquid aromatic hydrocarbons. Examples of other liquid hydrocarbons include oils produced by the distillation of coal and the distillation of various types and grades of petrochemical stocks, including kerosene oils that are obtained by fractional distillation of petroleum. Other petroleum oils include those generally referred to as agricultural spray oils (e.g., light and medium spray oils that include middle fractions in the distillation of petroleum and which are only slightly volatile). Such oils are usually highly refined and may contain only minute amounts of unsaturated compounds. Such oils, moreover, are generally paraffin oils and accordingly can be emulsified with water and an emulsifier, diluted to lower concentrations, and used as sprays. Tall oils, obtained from sulfate digestion of wood pulp, like the paraffin oils, can similarly be used. Other organic liquid carriers may include, for example, liquid terpene hydrocarbons and terpene alcohols such as alpha-pinene, dipentene, and terpineol.

Other suitable carriers may include, for example, aliphatic and aromatic alcohols, esters, aldehydes, ketones, mineral oil, higher alcohols, finely divided organic and inorganic solid materials. In addition to the above-mentioned liquid hydrocarbons, the carrier may include, for example, conventional emulsifying agents, which can be used for facilitating the dispersal of the formulation or composition to the environment, and/or to the surface of a subject or an object. Aliphatic monohydric alcohols may include, for example, methyl, ethyl, normal-propyl, isopropyl, normal-butyl, sec-butyl, and tert-butyl alcohols. Suitable alcohols may include, for example, glycols (e.g., ethylene and propylene glycol) and pinacols. Suitable polyhydroxy alcohols may include, for example, glycerol, arabitol, erythritol, and sorbitol. Suitable cyclic alcohols may include, for example, cyclopentyl and cyclohexyl alcohols.

Solid carriers that can be used in the compositions described herein may include, for example, finely divided organic and inorganic solid materials. Suitable finely divided solid inorganic carriers may include, for example, siliceous minerals such as synthetic and natural clay, bentonite, attapulgite, fuller's earth, diatomaceous earth, kaolin, mica, talc, finely divided quartz, as well as synthetically prepared siliceous materials, such as silica aerogels and precipitated and fume silicas. Examples of finely divided solid organic materials may include cellulose, sawdust, and synthetic organic polymers. Examples of semi-solid or colloidal carriers may include waxy solids, gels (e.g., petroleum jelly), and lanolin, and mixtures of liquid and solid substances.

Additionally, the compositions or formulations described herein may include any conventional "stabilizer" formulation agents known in the art, including, for example, tert-butyl sulfinyl dimethyl dithiocarbonate.

The compositions described herein may include adjuvant formulation agents used in personal care product formulations, such as thickeners, buffering agents, chelating agents, preservatives, fragrances, antioxidants, gelling agents, stabilizers, surfactants, emollients, coloring agents, aloe vera, waxes, lanolins, other penetration enhancers and mixtures thereof, and therapeutically or cosmetically active agents. Therapeutically or cosmetically active formulation agents useful for the compositions or formulations disclosed herein may include, for example, fungicides, sunscreening agents, sunblocking agents, vitamins, tanning agents, plant extracts, anti-inflammatory agents, anti-oxidants, radical scavenging agents, retinoids, alpha-hydroxy acids, emollients, antiseptics, antibiotics, antibacterial agents, and antihistamines.

In some embodiments, the compositions described herein may further include one or more insect repellent formulation agents known in the art including, for example benzil, benzyl benzoate, 2,3,4,5-bis(butyl-2-ene) tetrahydrofurfural, butoxypolypropylene glycol, N-butylacetanilide, normal-butyl-6,6-dimethyl-5,6-dihydro-1,4-pyrone-2-carboxylate, dibutyl adipate, dibutyl phthalate, di-normal-butyl succinate, N,N-diethyl-meta-toluamide, dimethyl carbate, dimethyl phthalate, 2-ethyl-2-butyl-1,3-propanediol, 2-ethyl-1,3-hexanediol, di-normal-propyl isocinchomeronate, 2-phenylcyclohexanol, p-methane-3,8-diol, and normal-propyl N,N-diethylsuccinamate.

The compositions described herein may include other known compatible active formulation agents including, for example, insecticides, acaricides, rodenticides, fungicides, bactericides, nematocides, herbicides, fertilizers, and growth-regulating agents. In some embodiments, the agents may be in the form of particular dosage preparations for specific application made therefrom, such as solutions, emulsions, suspensions, powders, pastes, and granules as described herein or as otherwise known in the art which are thus ready for use.

The compounds or compositions described herein may be administered in combination with other insect control agents. For example, the compositions may employ various chemicals that affect insect behavior, such as insecticides, attractants and/or repellents, or as otherwise known in the art. The compounds identified by the methods and systems herein may also be administered with chemosterilants.

The amount of the compounds in the compositions described herein may vary depending on the application. For example, in some embodiments, the compositions described herein has at least about 0.0001% by weight of one or more of the compounds identified by the methods or systems described herein, or about 0.0001% to about 99% by weight of one or more of the compounds identified by the methods or systems described herein, or about 0.001% to about 90% by weight of one or more of the compounds identified by the methods or systems described herein, or about 0.01% to about 80% by weight of one or more of the compounds identified by the methods or systems described herein, or about 0.1% to about 70% by weight by weight of one or more of the compounds identified by the methods or systems described herein, or about 1% to about 50% by weight of one or more of the compounds identified by the methods or systems described herein.

It should be understood that the compositions described herein contain sufficient amounts of the one or more of the compounds identified by the methods or systems described herein so as to modulate arthropod olfactory receptors and influence or control an arthropod's (e.g., insect's) behavior.

In one embodiment, the one or more of the compounds identified by the methods or systems described herein are incorporated in effective amounts into a composition suitable for applying to the surface of an object or subject, such as to a subject's (e.g., a human's) skin. Suitable compositions for topical applications include a vehicle, such as an alcohol based solvent, a lotion such as numerous skin creams known in the art, a siliceous clay, or a combination thereof. One of skill in the art would recognize that, for such topical applications to be effective, the evaporation rate of the compounds from the surface of the object or subject must be sufficiently high enough to provide a vapor density which has the desired effect on the target arthropods. However, a balance must be struck between the evaporation rate and the duration of the desired effect—too high of an evaporation rate will lower the effectiveness of the arthropod olfactory receptor modulating compounds for longer time points. Numerous extrinsic factors affect the evaporation rate, such as the ambient temperature, the temperature of the treated surface, and the presence or absence of air movement. Thus, it should be understood that the compositions described herein have a surface evaporation rate of at least a minimum effective evaporation rate. In certain embodiments, the composition has a surface evaporation rate of at least a minimum effective evaporation rate for at least 1, 2, 3, 4, 5, 6, 7, 8, 10, or 12 hours.

It should further be understood that, when formulating the compounds described herein for specific topical applications to a subject's (e.g., a human's) skin, the compounds described herein are generally mixed in a dermatologically acceptable carrier, such pharmaceutically acceptable creams, polymers, lotions, gels, and/or liquids. The pharmaceutically acceptable carriers may further provide water repellency, prevent skin irritation, and/or soothe and condition skin. Factors to consider when selecting a carrier(s) for any formulation with one or more compounds of the disclosure include solubility, commercial availability, cost, evaporation rate, olfactory, stability, and whether the carrier itself exerts a biological effect on arthropod olfactory receptors. One of skill would also recognize that the application of the compositions and compounds of the disclosure do not only include human subjects, but include canines, equines, bovines and other animals subject to exoparasitic sanguinivorous feeding arthropods.

Further, it should be understood that, while the compounds identified by the methods and systems described herein and compositions thereof are effective at affecting arthropod olfactory receptor activity and thus arthropod behavior, under typical conditions of use, it may under some circumstances be desirable to reduce the rate of evaporation thereof. A variety of strategies may be employed to reduce the evaporation rate of the compounds disclosed herein, if so desired. For example, one method is to combine the compounds disclosed herein with a polymer or other inert ingredient, forcing the compounds disclosed herein to migrate through the mixture to the surface before it can evaporate. Alternatively, the compounds described herein may be micro-encapsulated to control rates of evaporation from the surface of a subject or object. In still another alternative, a precursor molecule may be prepared, which slowly disintegrates on the surface of the subject or object thereby slowing the evaporation rate of one or more arthropod olfactory receptor modulating compounds disclosed herein to the environment. For example, release of one or more arthropod olfactory receptor modulating compounds of the disclosure may be, for example, by sub-micron encapsulation, in which one or more compounds disclosed herein is encapsulated (surrounded) within a skin nourishing protein or a liposome. The protein or liposome may be used at, for example, a defined concentration. Examples of one or more encapsulated compounds disclosed herein may include water-based lotions, oil-based lotions, gels, or water for spray application. After coming in contact with a subject's (e.g., human's) skin the protein or liposomes would begin to breakdown, thereby releasing the encapsulated arthropod olfactory receptor modulating compounds. The process would continue as each microscopic capsule is depleted then replaced in succession by a new capsule that contacts the skin and releases its encapsulated arthropod olfactory receptor modulating compound. Generally, the process may take up to 24 hours for one application. Because a protein's and liposome's adherence to the skin is so effective, these formulas are very resistant to perspiration (sweat-off), and water. Alternatively, one or more arthropod olfactory receptor modulating compounds disclosed herein may be encapsulated in polymers. Use of such polymers, would allow for applications to slowly release one or more arthropod olfactory receptor modulating compounds to the environment from the surface of a subject and also from the surface of an object. Suitable polymers include, for example, high density polyethylene, low density polyethylene, biodegradable thermoplastic polyurethanes, biodegradable ethylene polymers, and poly(epsilon caprolactone) homopolymers and compositions containing the same, as disclosed for example in U.S. Pat. No. 4,496,467, U.S. Pat. No. 4,469,613 and U.S. Pat. No. 4,548,764. Specific examples of biodegradable polymers include DuPont Biomax® biodegradable polyester and poly-L-lactide.

The compounds identified by the methods and systems described herein and compositions thereof may also be applied to or impregnated onto the surfaces of an object. Examples of such applications include applying or impregnating the compounds to clothing, netting, fabrics, bedding, screens, camping gear, leather, felt, and a sheet-like objects such as paper. Further, when applied to subjects such as pets, the compounds of the may be applied or impregnated onto resin collars.

The compounds identified by the methods and systems described herein may also be formulated to generate solutions, suspensions, creams, ointments, gels, films or sprays, depending on the desired method of use. The formulation agents may be aerosol-based carriers adapted to disperse the arthropod olfactory receptor modulating compounds of the disclosure into the atmosphere by means of propellants. Examples propellants include, for example, liquefied petroleum gas (hereinafter referred to as "LPG") and dimethyl ether (hereinafter referred to as "DME"). One of skill in the art would recognize the desirable properties for a topical applications, including for example low toxicity, resistance to loss by water immersion or sweating, low or no olfactory or at least a pleasant odor, ease of application, and rapid formation of a dry tack-free surface film on the subject's (e.g. humans') skin.

In some embodiments, the compounds identified by the methods and systems described herein may be used in products suitable for human use, including, for example, colognes, lotions, sprays, creams, gels, ointments, bath and shower gels, foam products (e.g., shaving foams), makeup, deodorants, shampoo, hair lacquers/hair rinses, and personal soap compositions (e.g., hand soaps and bath/shower soaps).

In other embodiments, the compounds identified by the methods and systems described herein may be emitted from vaporizers, treated mats, cylinders, oils, candles, wicked apparatus, and fans. For example, the compounds may be used to form vapors in barns, houses, or patios to repel insect pest and/or mask a subject from an arthropod pest.

Certain compounds identified herein may antagonize, agonize, and/or superagonize arthropod olfactory and/or taste receptors so as to control or influence arthropod behavior, and/or to mask the olfactory cues of a subject or an object. Other compounds identified herein as an arthropod repellent may be used as arthropod repellents or attractants, as masking agents for a subject or an object olfactory cues; and/or to control and influence insect behavior, such as triggering avoidance behavior, feeding behavior, mate seeking behavior, and/or indifference to olfactory cues from a subject or an object.

The compounds and compositions described herein may be used for inhibiting, preventing or reducing the incidence of arthropod-borne disease in a subject, by superagonizing and/or antagonizing one or more olfactory receptors of an arthropod. In some embodiments, the receptor activity is modulated so that the arthropod has limited to no attraction to the olfactory cues emanating from a subject, thereby inhibiting, preventing or reducing the incidence of arthropod-borne disease in a subject. In other embodiments, the arthropod-borne disease is selected from malaria, dengue, yellow fever, river blindness, lymphatic filariasis, sleeping sickness, leishmaniasis, epidemic polyarthritis, West Nile virus disease Lyme disease, Rocky Mountain Fever, and Australian encephalitis, or any combination thereof.

Repellent Compounds and Compositions Thereof

Provided herein are also the one or more compounds identified according to any of the methods and systems described herein that may be used as a repellent against at least one arthropod species.

In some embodiments, one or more of the compounds of formulae (Ia), (Va), (III), and (XII), as described above, or any combinations thereof can be used as arthropod repellents. In certain embodiments, two or more of the compounds of formulae (Ia), (Va), and (III), or any combination thereof, are arthropod repellents.

Provided herein are also compositions including two or more compounds selected from compounds of formulae (IA), (VA), and (III), or any combination thereof, for use as an arthropod repellent.

In some embodiments, the repellent composition includes:
  i) one or more compounds of formula (Ia); and
  ii) one or more compounds of formulae (Va) and (III), or any combination thereof.

In certain embodiments, the repellent composition includes:
  i) one or more alkyl 2-oxopropanoates; and
  ii) one or more compounds selected from compounds of formulae (Ia), (Va) and (III), or any combination thereof.

In one embodiment, the repellent composition includes:
  i) one or more compounds selected from ethyl 2-oxopropanoate and methyl 2-oxopropanoate; and
  ii) one or more compounds selected from compounds of formulae (Ia), (Va) and (III), or any combination thereof.

In other embodiments, one or more of the compounds of formula (XII) are arthropod repellents. Provided herein are also compositions including one or more compounds of formula (XII) for use as an arthropod repellent.

Any combinations of the repellents disclosed herein may be used together in a blend. For example, a blend of compounds selected from compounds of formulae (Ia), (Va), (III), and (XII), or any combination thereof, may be used. It should be understood that the blend may include a compound from each formula, or multiple compounds for a formula, or any combination thereof (e.g., a compound from one formula and multiple compounds from another formula). For example, the blend may include two compounds of formula (Ia) and a compound of formula (XII). In other examples, the blend may include one compound of formula (Ia), one compound of formula (Va), and one compound of formula (XII). In certain embodiments, the repellent blend may include two or more compounds, three or more compounds, or four or more compounds. In one embodiment, the repellent blend may include, two, three or four compounds of formulae (Ia), (Va), (III), and (XII), or any combination thereof.

In other embodiments, the repellent compositions includes a combination of pyruvate inhibitors and superactivators. In one embodiment, the repellent composition includes: i) one or more pyruvate inhibitors selected from the compounds of Table A, Group II; and ii) one or more superactivators selected from the compound of Table A, Group III.

In yet other embodiments, the repellent composition includes propanal, thiophene-2-thiol, or a combination thereof.

The arthropod repellents identified according to the methods or systems described herein may be formulated into a repellent for topical application, such as in the form of a lotion, cream, spray or dust. In some embodiments, the repellent may be included in, for example, a vaporizer, a treated mat, treated outerwear, an oil, a candle, or a wicked apparatus.

Attractant Compounds and Compositions Thereof

Provided herein are also the one or more compounds identified according to any of the methods or systems described herein that may be used as an attractant against at least one arthropod species.

In some embodiments, one or more of the compounds of formulae (Ia), (Xb), (Xc), and (XIa), as described above, or any combination thereof, can be used as arthropod attractants. Provided herein are also compositions including one or more of the compounds of formulae (Ia), (Xb), (Xc), and (XIa), or any combination thereof, for use as a arthropod attractant. In certain embodiments, the attractant composition includes two or more compounds of formula (Ia), (Xb) and (XIa), or any combination thereof. In another embodiment, the attractant composition includes two or more compounds of formula (Xb) and (XIa), or any combination thereof.

In certain embodiments, the attractant composition includes:
  i) one or more compounds selected from thiophene, cyclopentanone, 1H-pyrrole, hex-5-en-2-one, methyl 2-methylpropanoate; and
  ii) one or more compounds selected from compounds of formulae (Ia), (Xb), (Xc), and (XIa), or any combination thereof.

In certain embodiments, the attractant composition includes a cycloalkanone, and optionally one or more compounds selected from compounds of formulae (Ia), (Xb), (Xc), and (XIa), or any combination thereof. In some embodiments, the cycloalkanone is a $C_4$ to $C_6$ cycloalkanone. In one embodiment, the cycloalkanone is cyclopentanone. In one embodiment, the attractant composition includes cyclopentanone and ethyl acetate.

In other embodiments, the attractant compositions includes two or more, three or more, or four or more compounds selected from Table A, Group I. In certain embodiments, the composition includes two, three, or four compounds selected from Table A, Group I.

In yet other embodiments, the attractant composition includes one or more, two or more, three or more, or four or more compounds selected from 2-methylpropan-1-ol, 2-methyloxolane, 3-methylbut-3-en-1-ol, butan-2-ol, propan-2-yl formate, propan-1-ol, methyl formate, cyclopentanol, and cyclopentane. In certain embodiments, the attractant composition includes one or more, two or more, three or more, or four or more compounds selected from 2-methyloxolane, propan-2-yl formate, methyl formate, cyclopentanol, and cyclopentane.

The arthropod attractants identified according to the methods or systems described herein may be used to lure an arthropod into a trap. For example, the trap may be suction-based, light-based, electric current-based.

EXAMPLES

The following examples are merely illustrative and are not meant to limit any embodiments of the present disclosure in any way.

Example 1

Ability of cpA Receptor Neuron to Detect Human Skin Odorants

This Example demonstrates that volatiles from human skin may directly activate cpA. In particular, human foot odor collected directly onto glass beads is sufficient to activate the cpA neuron in *A. aegypti*.

Materials and Methods

Figure 7A:
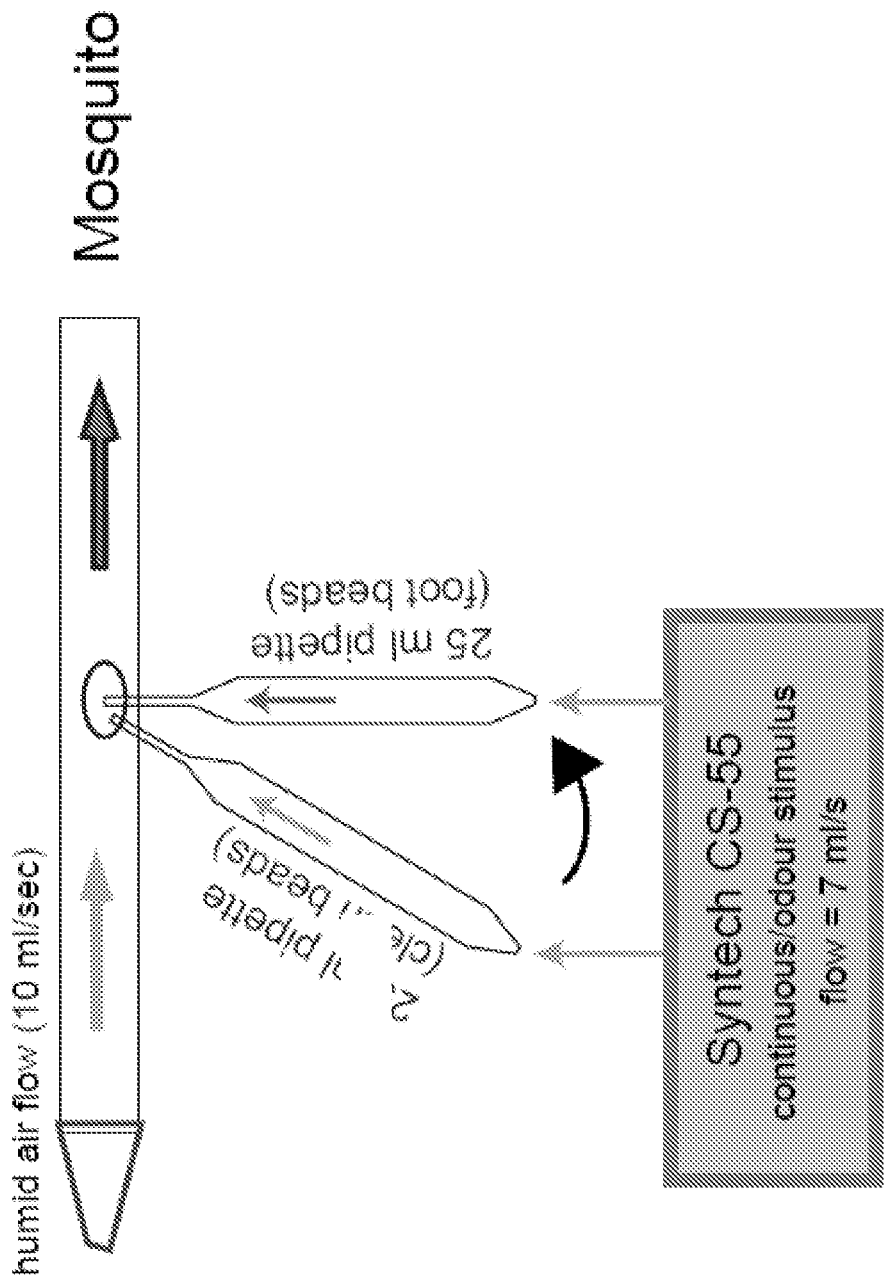
FIG. 7a is a schematic of a human odor delivery system.

Electrophysiology:

Adult female *A. aegypti* (Linnaeus 1762) (Rockefeller strain) *A. gambiae* sensu stricto Giles 1902 (G3 strain), or *C. quinquefasciatus* Say 1823 were tested 3-12 days post-emergence with single-sensillum extracellular recordings. Chemicals were obtained from Sigma-Aldrich at the highest purity (typically >99%) and were dissolved in paraffin oil or water. Human odor was collected on glass beads worn in socks for ~6 hrs and 20 ml beads were placed inside a 25 ml disposable pipette through which a puff of air was delivered, switching from a comparable cartridge containing clean beads (FIG. 7a). Response to clean beads was subtracted from the results reported. Only sensilla with cpA activity of <20 spikes $s^{-1}$ to negative control were considered for analysis.

Figure 7B:
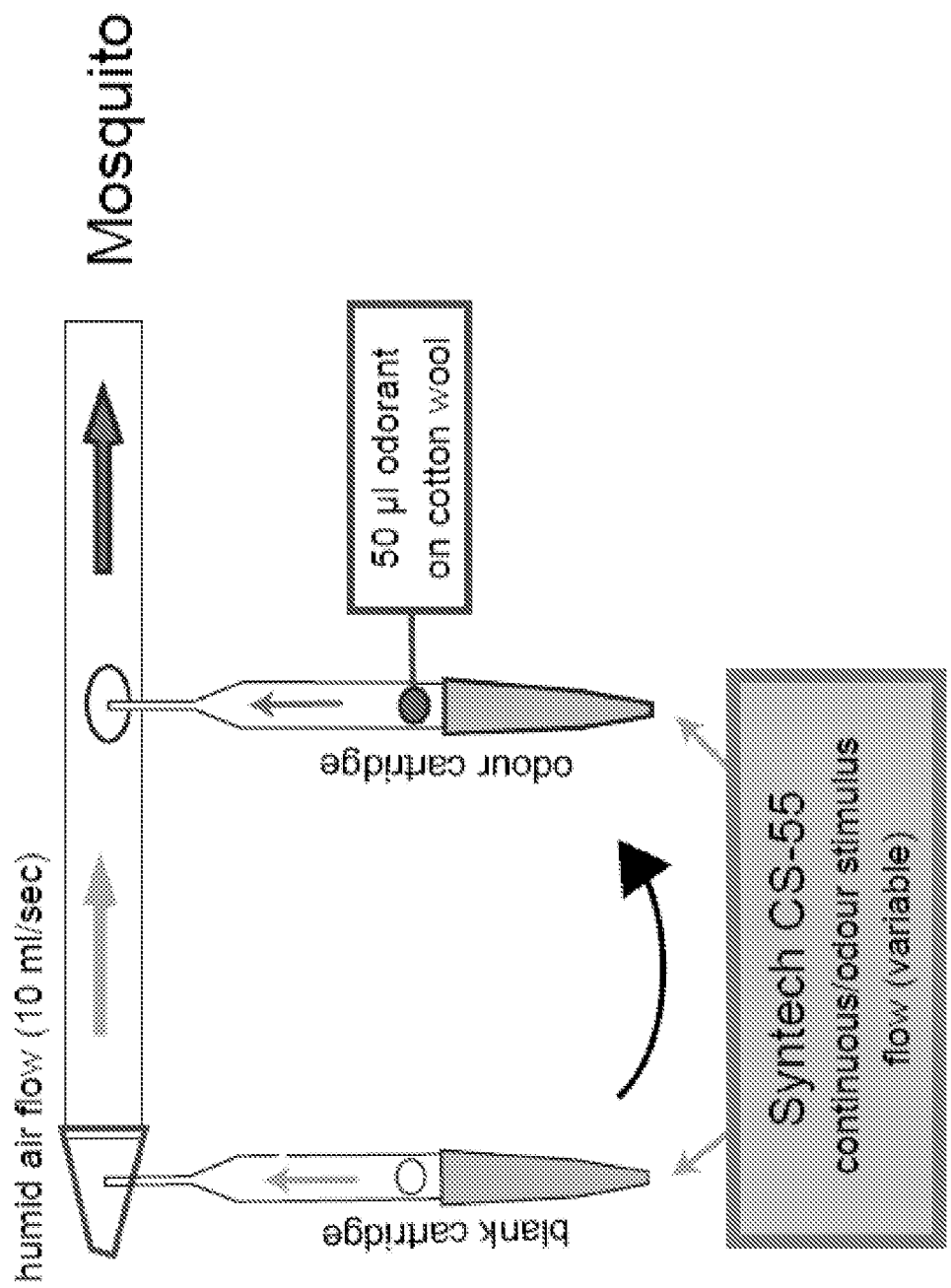
FIG. 7b is a schematic of an activation screen. For the activation screen, insertion sites for "blank" and "odor cartridges" were spaced 12 cm apart, and flow rates through the stimulus controller were adjusted for each individual preparation. Black arrows indicate switch in airflow during stimulus delivery.
Figure 8A:
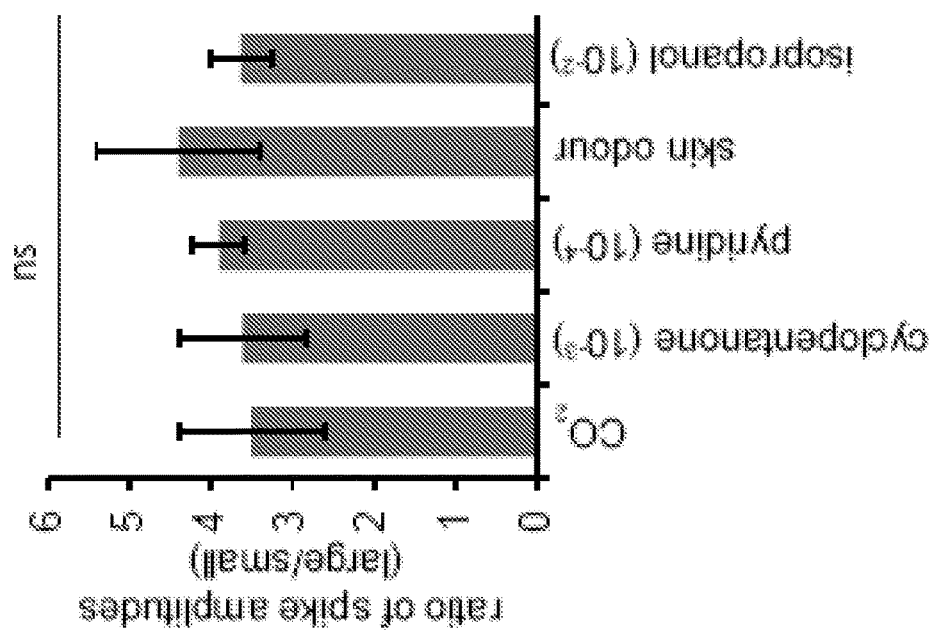
FIGS. 8a-8f illustrate an electrophysiological analysis of cpA action potential and spiking activity in response to various stimuli (such as odors).
Figure 8B:
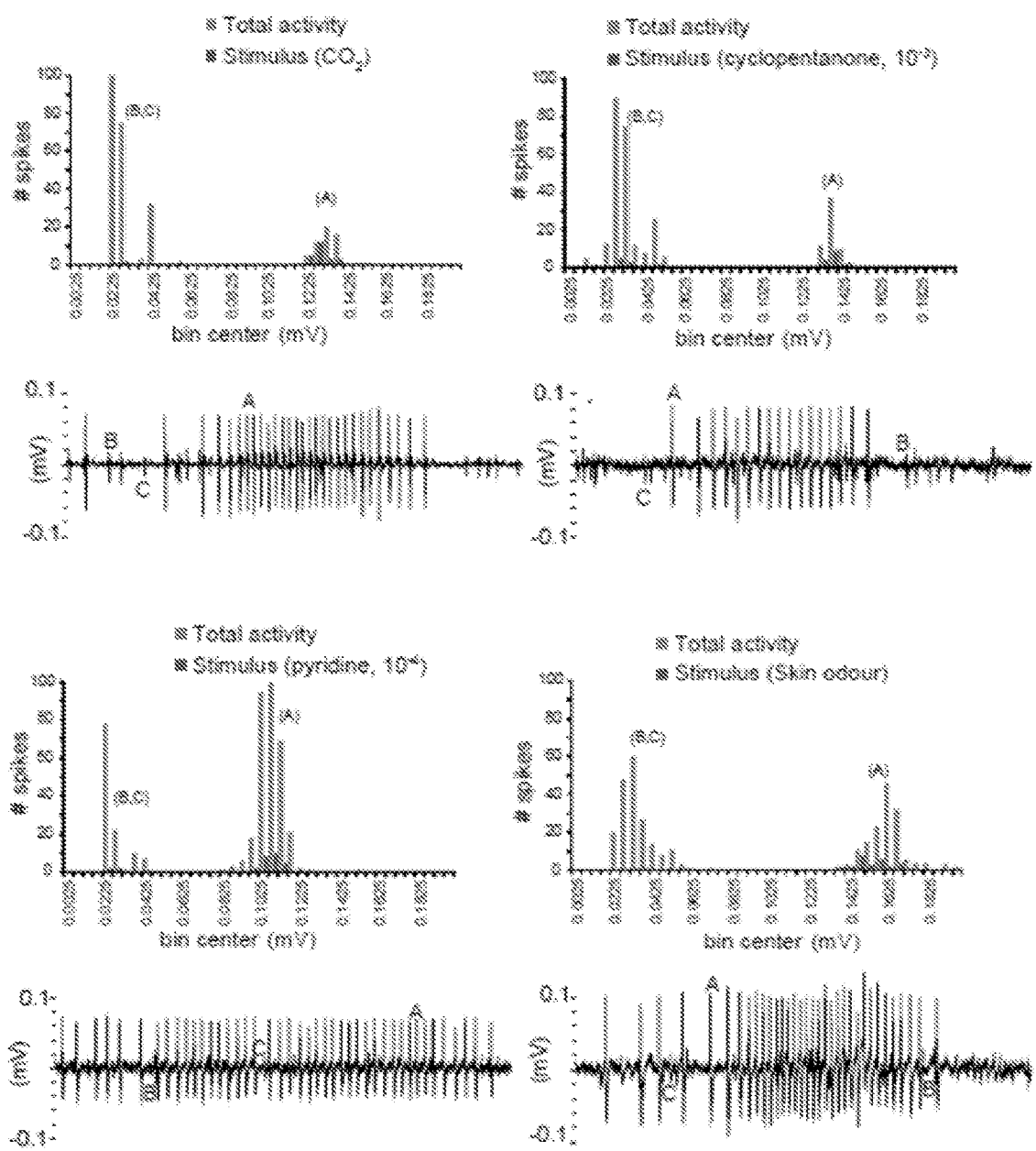
Figures 8C, 8D:
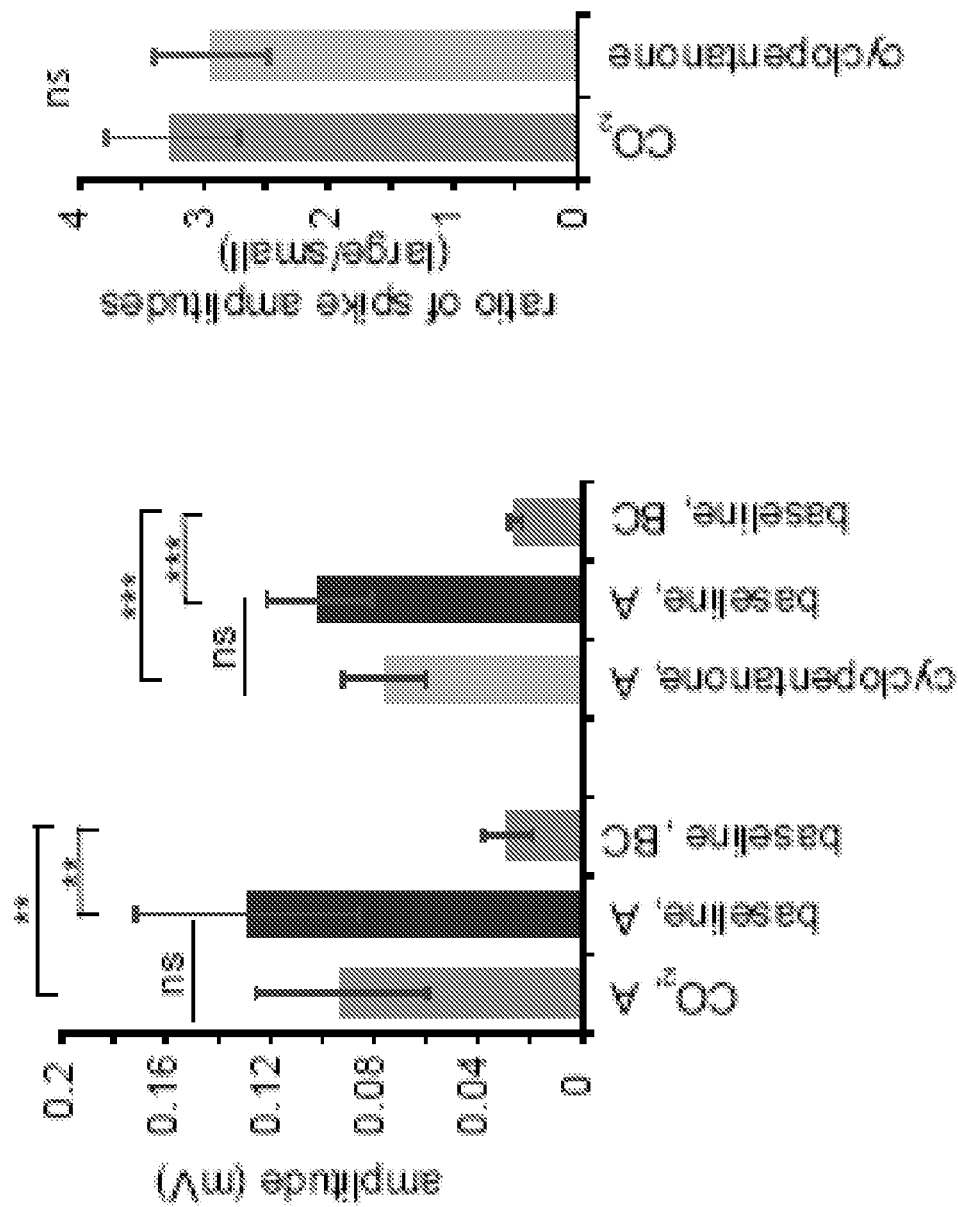
Figure 8E:
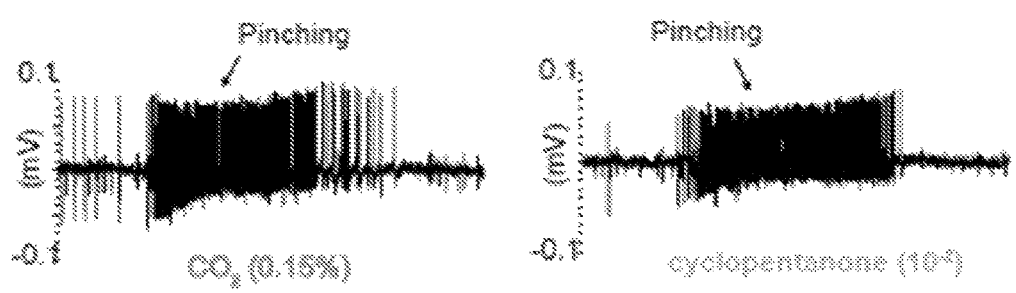
Figure 8F:
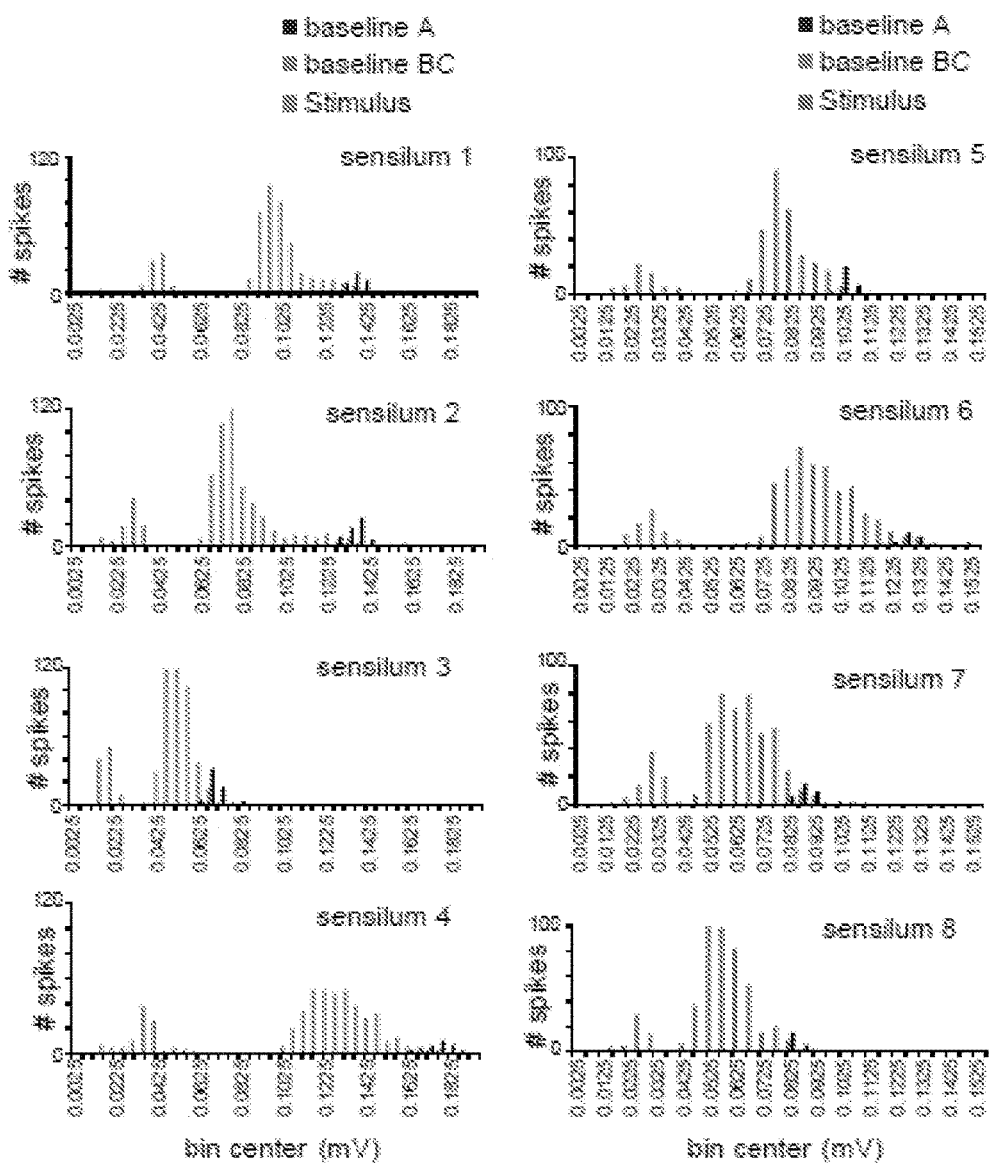

CpA-off and sham treated mosquitoes were pre-treated for 3 min in an upended 1 L glass dish in which 100 µl of fresh butyryl chloride (1%) or paraffin oil was allowed to vaporize for 10-20 min. The odor delivery system for different screens is shown in FIG. 7b; solvent responses during the same recording session were subtracted. Inhibition screen was tested. For the ultra-prolonged activator the 3-s stimulus was delivered from a 10 ml disposable pipette using a CS-55 stimulus controller (Syntech), $CO_2$ was delivered, and responses to subsequent odor stimuli were calculated by subtracting baseline activity 1 s prior to each stimulus. When responses to repeated pulses of cyclopentanone and $CO_2$ were compared, baseline activity between seconds 5 and 6 following each stimulus was subtracted. Spike counting was done manually or with Igor Pro6.2 (Wavemetrics) with the Neuromatic v2.00 macro (by Jason Rothman), and peak-to-peak spike amplitudes for FIG. 8 were analysed in Clampfit 10.3 (Molecular Devices).

Results

A panel of odorants selected from the hundreds of compounds that were detected in human skin, sweat, or associated microbial odors for structural similarity to known ligands of cpA (Table 1 below).

TABLE 1

Panel of odorants

| Odor name | Where previously detected |
| --- | --- |
| 1-butanol | Upper back/forearm skin, forehead sweat (fresh and incubated), foot microbe headspace, total effluent |
| 1-decanol | Incubated forehead sweat |
| 1-nonanol | Incubated forehead sweat |
| 1-octanol | Incubated forehead sweat, expired air |
| 1-pentanol | Forehead sweat (fresh and incubated), total effluent |
| 2,3-dimethyl-2-cyclopenten-1-one | Foot microbe headspace |
| 2,5-dimethylpyrazine | Foot microbe headspace |
| 2-ethyl-3,(5 or 6)-dimethylpyrazine | Foot microbe headspace |
| 2-furoic acid | Incubated axillary sweat |
| 2-hexenoic acid | Female apocrine sweat |
| 2-methyl-1-butanol (racemic) | Incubated forehead sweat, foot microbe headspace |
| 2-methylbutyraldehyde | Handprints, foot microbe headspace |
| 2-methylbutyric acid (racemic) | Foot and skin microbe headspace |
| 2-methylcyclopentanone | Upper back/forearm skin |
| 2-methylheptanoic acid | Male and female axillary sweat |
| 2-methylhexanoic acid | Male and female axillary sweat, female apocrine sweat |
| 2-methylnonanoic acid | Male and female axillary sweat, female apocrine sweat |
| 2-nonanone | Incubated forehead sweat, foot microbe headspace |
| 3,5,5-trimethyl-1-hexanol | Incubated forehead sweat |
| 3-acetoxy-2-butanone | Foot microbe headspace |
| 3-hexanol | Upper back/forearm skin |
| 3-methyl-1-butanol | Incubated forehead sweat, foot and skin microbe headspace |
| 3-methyl-2-buten-1-ol | Incubated forehead sweat |
| 3-methylcyclopentanone | Upper back/forearm skin |
| 4-methyl-3-penten-2-one | Fresh forehead sweat |
| 5-nonanone | Foot microbe headspace |
| acetoin | Fresh and incubated forehead sweat, foot microbe headspace |
| adipic acid | Handprints |
| benzaldehyde | Incubated axillary sweat, microbial headspace, upper back/forearm skin, handprints, total effluent |
| butanone | Handprints, total effluent |
| cyclohexanone | Fresh forehead sweat, foot microbe headspace, total effluent |
| heptanoic acid | Male and female axillary sweat, female apocrine sweat, handprints, leg sweat |
| hexanoic acid | Forehead/trunk sweat, upper back/forearm skin, fresh forehead sweat, male and female axillary sweat, female apocrine sweat, handprints, leg sweat, whole body sweat |
| indole | Incubated forehead sweat, foot microbe headspace, handprints, total effluent |
| isovaleric acid | Forehead/trunk sweat, upper back/forearm skin, incubated forehead sweat, foot microbe headspace, whole body sweat |
| octanal | Incubated axillary sweat, upper back/forearm skin, fresh forehead sweat, handprints, total effluent |
| octanoic acid | Forehead/trunk sweat, upper back/forearm skin, male and female axillary sweat, female apocrine sweat, handprints, leg sweat, total effluent |
| pyrazine | Foot microbe headspace, handprints |
| pyridine | Incubated axillary sweat, upper back/forearm skin, fresh and incubated forehead sweat, handprints |
| trimethylpyrazine | Foot microbe headspace, handprints |

Figure 1C:
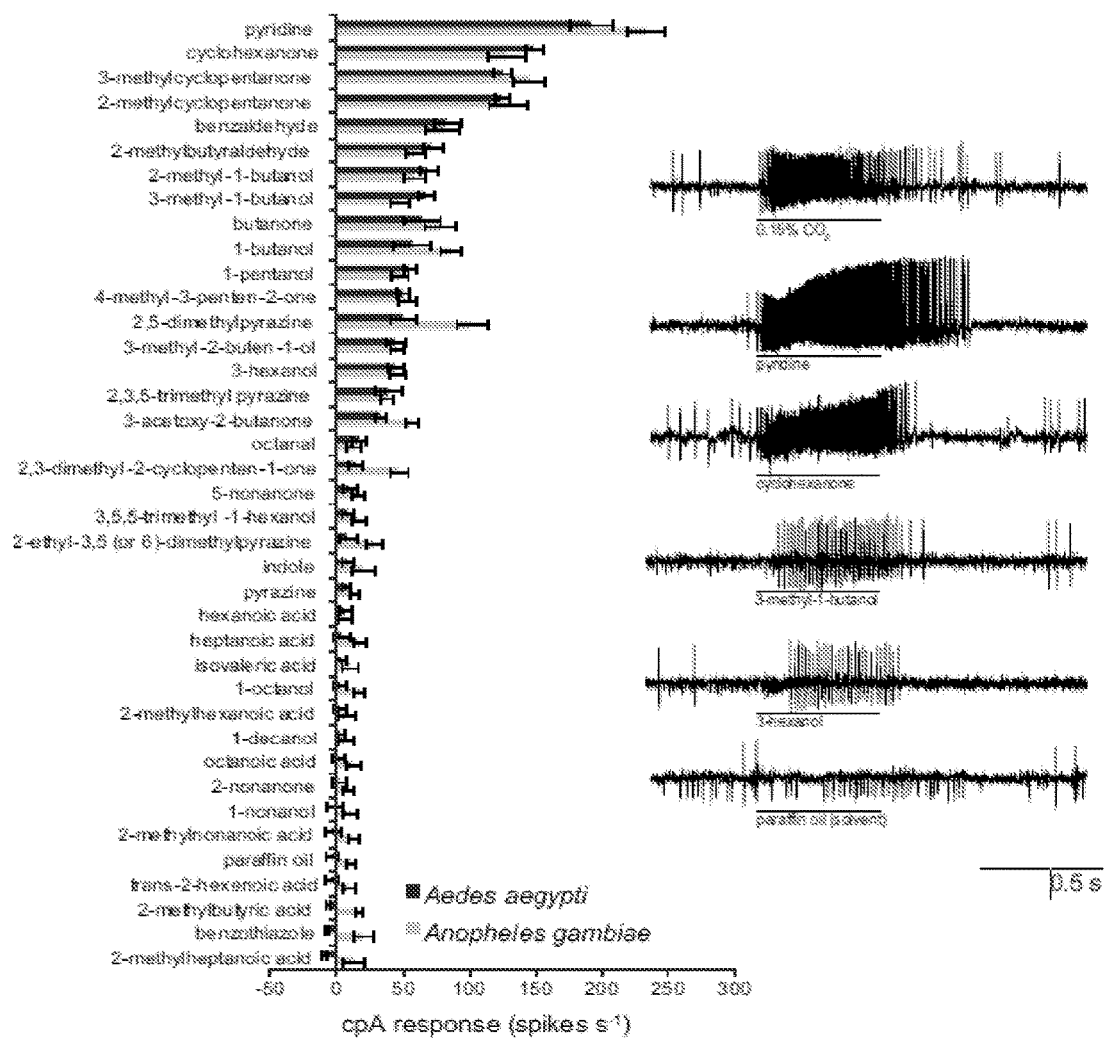
FIG. 1c includes a bar graph (left) summarizing the cpA response for individual components of skin odor in *A. aegypti* and *A. gambiae*, and representative traces and mean increase in firing rate of the cpA neuron to 0.5-s pulses of individual components of skin odor in *A. aegypti* and *A. gambiae*, where n=4-7 (right).
Figure 1D:
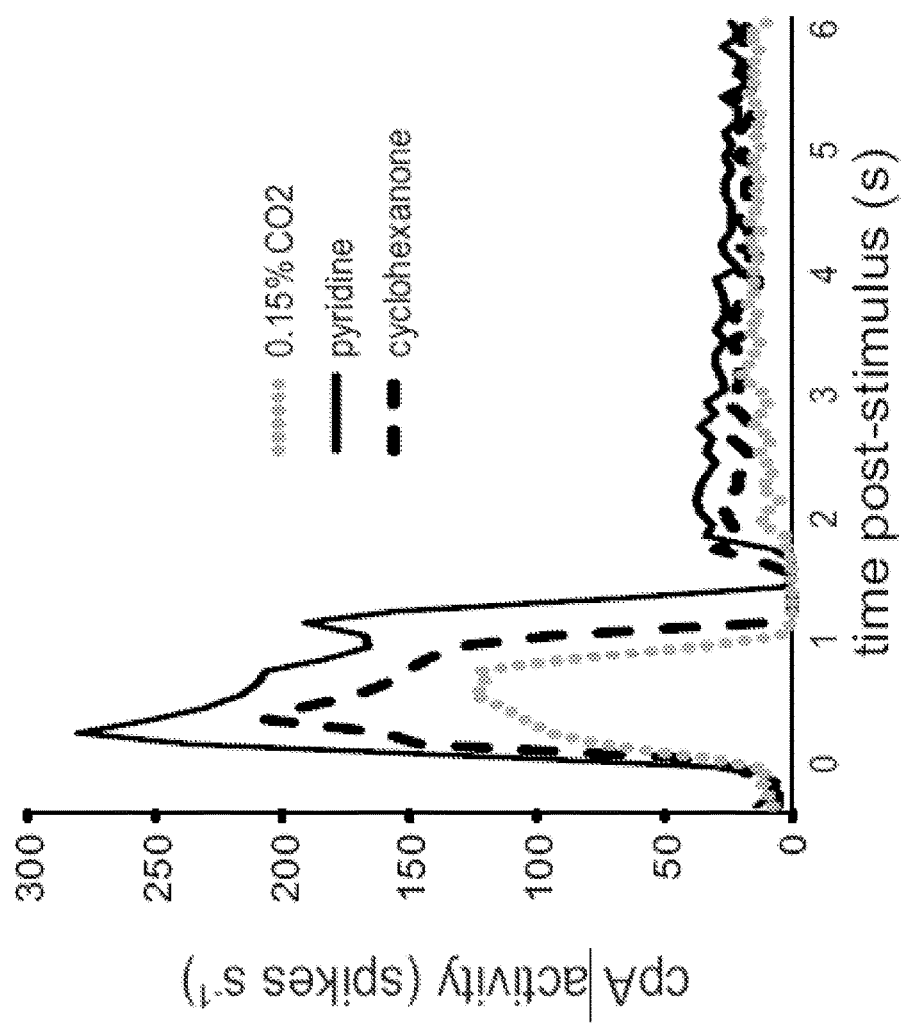
FIG. 1d is a graph illustrating the temporal response of the *A. aegypti* cpA mean firing frequency to a 1-s stimulus counted in 100-ms bins, where average response to n=4-5 stimuli is repeated in 15 s cycles.
Figure 1E:
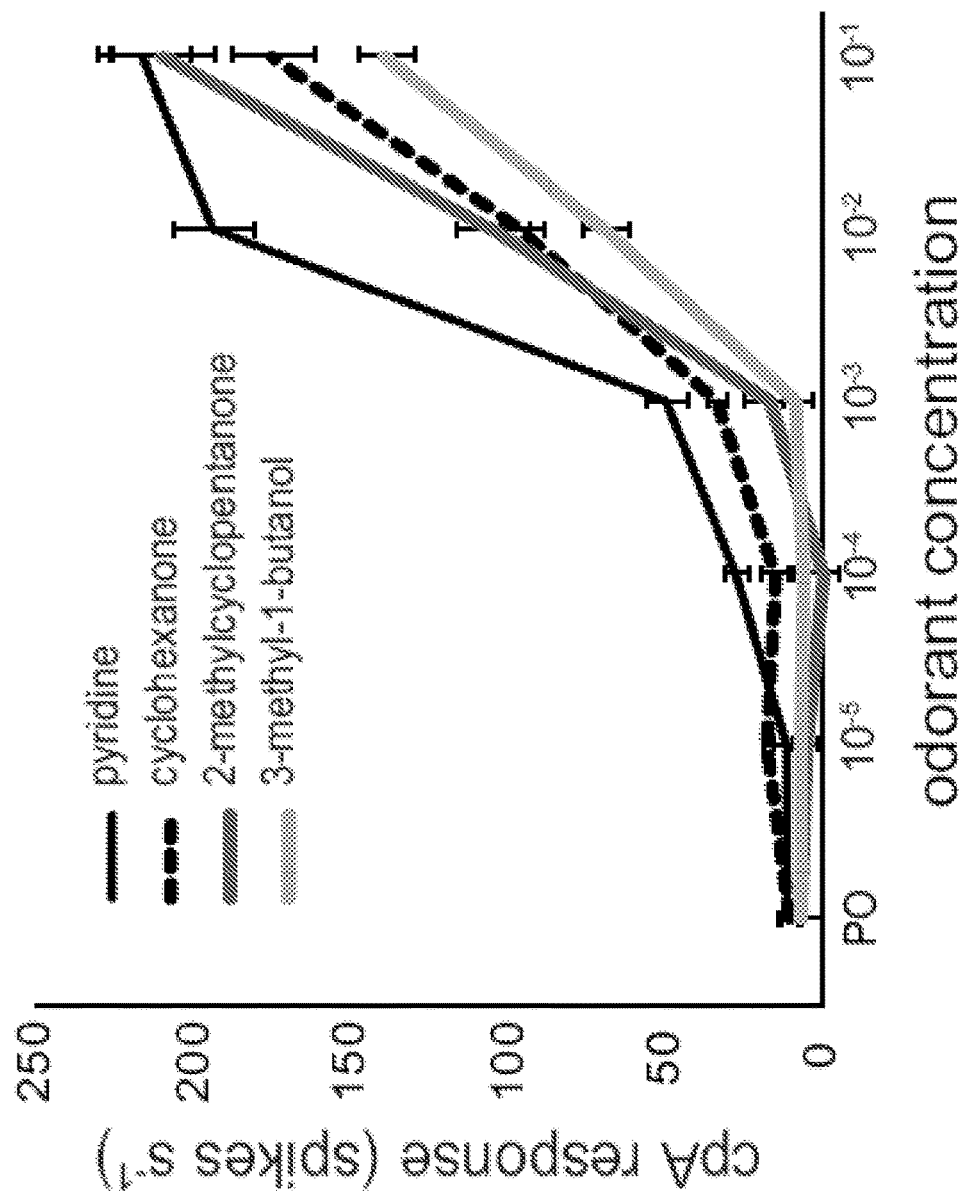
FIG. 1e is a graph illustrating *A. aegypti* cpA responses to representative activating odorants are dose dependent, in which all odorants except $CO_2$ is dissolved in paraffin oil (PO) at $10^{-2}$ except where indicated, and error bars are s.e.m.
Figure 9A:
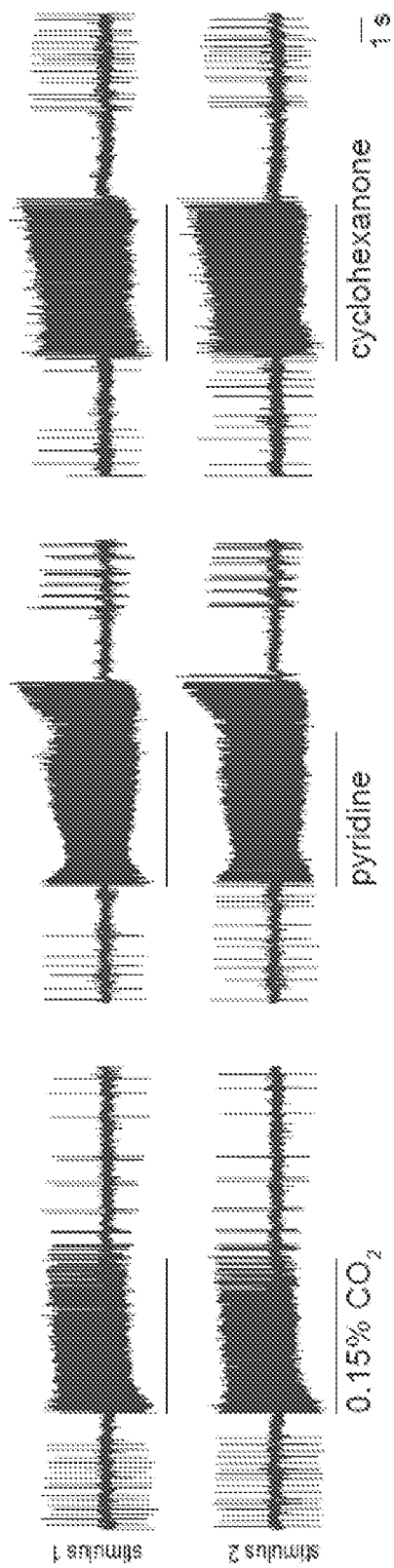
FIG. 9a illustrates sample traces from repeated stimulus experiments: 1-s pulses of odorant (10-2 in PO except $CO_2$) were repeated every 15 s; temporal dynamics of responses to each pulse of the same odorant were virtually identical and are summarized in FIG. 1d.

The panel of odorants were tested for activity with single-sensillum electrophysiology. Over 35% of these odorants activated the neuron strongly (>30 spikes $s^{-1}$) in *A. aegypti* (FIG. 1c). The neuron's responses to these skin-derived odorants were observed to be comparable to its response to $CO_2$ (FIG. 1d, FIG. 9a) and are dose-dependent (FIG. 1e).

Although the anthropophilic *A. aegypti* and *A. gambiae* belong to divergent mosquito subfamilies separated by 145-200 million years of evolution, their $CO_2$ receptor genes are highly conserved. Based on the data in this Example, the responses of the cpA neuron to this panel of odorants were found to be similar between these two species (FIG. 1c), suggesting a conserved role in detecting host odor.

Example 2

Involvement of cpA Neuron for Attraction to Human Skin Odor

This Example demonstrates the involvement of cpA activation by human odor for attraction, using a novel chemical-based strategy to shut down the activity of the $CO_2$ receptor in *A. aegypti*.

Materials and Methods

Electroantennogram Analysis:

Standard whole-antenna recordings were performed with minor modifications. Traces were averaged using Clampfit software (Molecular Devices), and responses were normalized to interspersed pulses of a reference odorant, 3-methyl-1-butanol, according to the formula: Raw response (mV)/(ax+by), where a and b are the responses (mV) to the immediately previous and subsequent reference odor stimulation, respectively, and x and y are the proportion of time elapsed between stimuli (so that x+y=1). Response to reference odorant did not significantly differ across treatment groups.

Wind Tunnel:

Room air (27° C.; 35-40% relative humidity was carbon filtered and drawn through a glass wind tunnel (36 cm×40 cm×128 cm) in a laminar flow at a constant rate of 0.2 m s$^{-1}$. Beads were elevated 7 cm above the floor of the wind tunnel in a covered 10 cm-diameter petri dish, 50 cm upwind from the release cage (FIG. 2h). Female *A. aegypti* were held in individual release cages without access to food or water for 17-23 hr at ~27° C. and ~70% relative humidity and pre-exposed to fresh butyryl chloride (1%) or solvent as above. The mosquito rested in the release cage for at least 60 s, following which covers over the beads and the release cage exit were removed to start the assay, video-recorded for 5 min. Landing was defined as alighting or walking onto the bead surface. Trials were conducted between 1400 and 1830 h. Days with poor response in positive control were not considered.

Figure 9B:
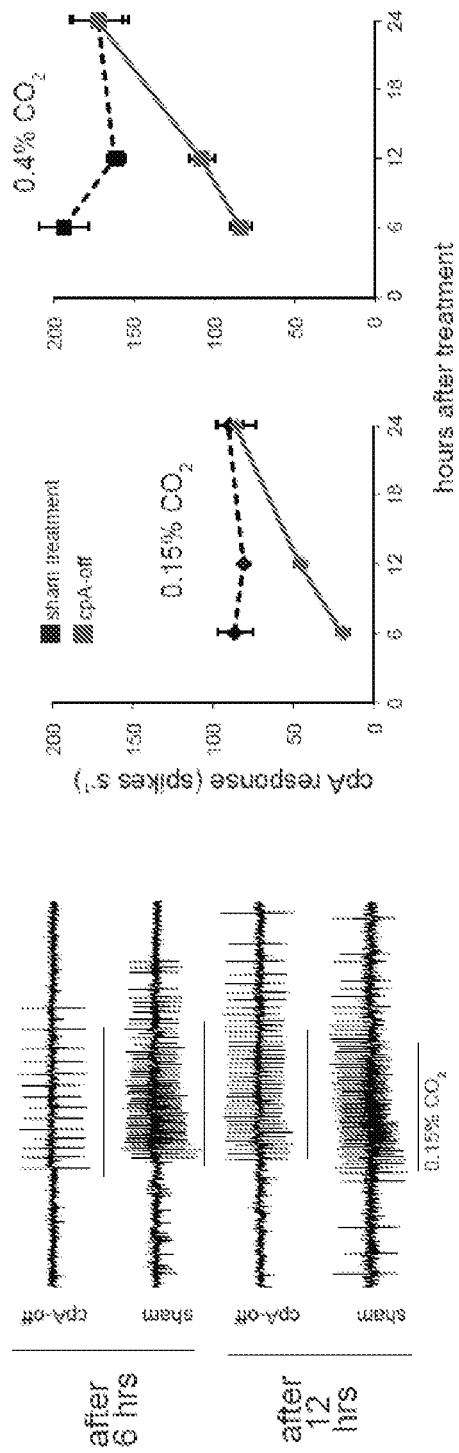
FIG. 9b illustrates sample traces and mean cpA responses to 0.5-s pulses of 0.15% and 0.4% CO2 from cpA-off or sham treated mosquitoes 6, 12, and 24 hours after treatment.
Figure 9C:
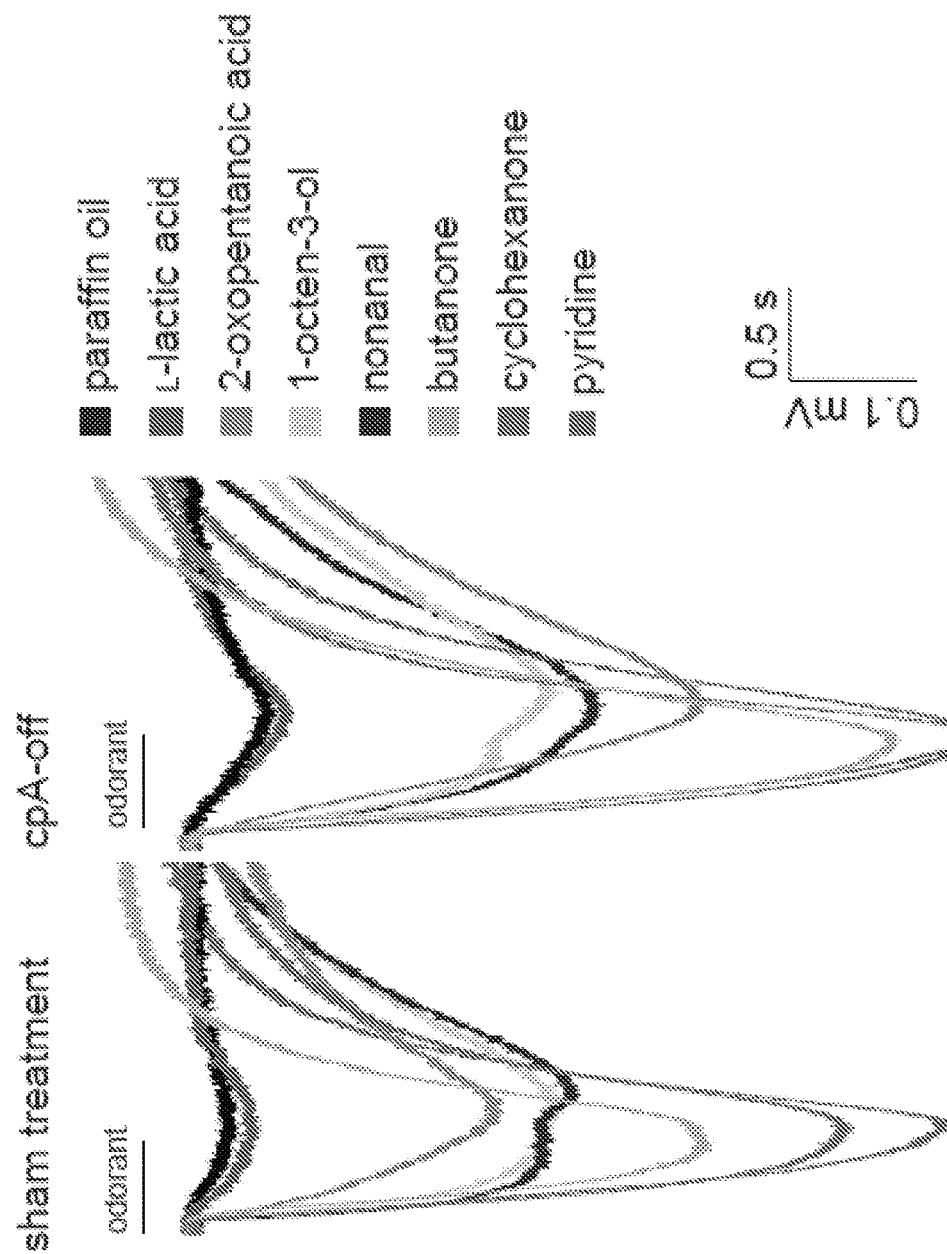
FIG. 9c illustrates averaged traces of EAG responses to 0.5-s stimuli of indicated odorants (10-1 in PO).
Figure 9D:
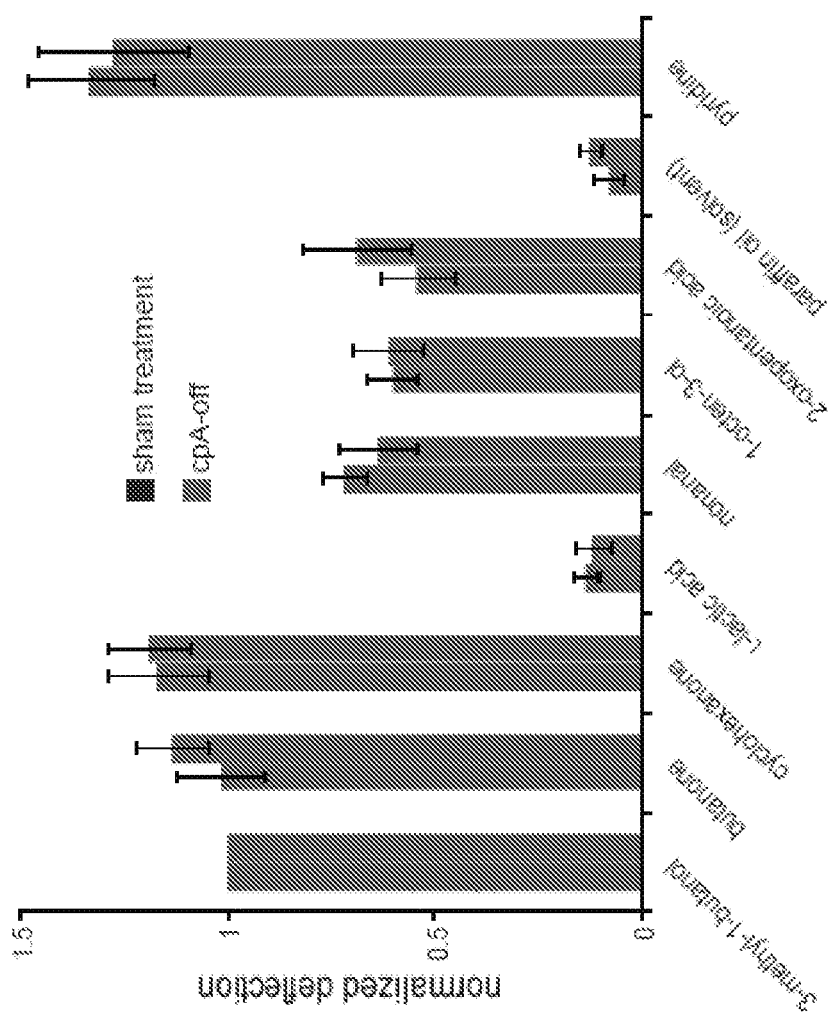
FIG. 9d illustrates EAG responses normalized to the reference odor 3-methyl-1-butanol. No significant differences due to treatment (n=9; t-test).
Figure 9E:
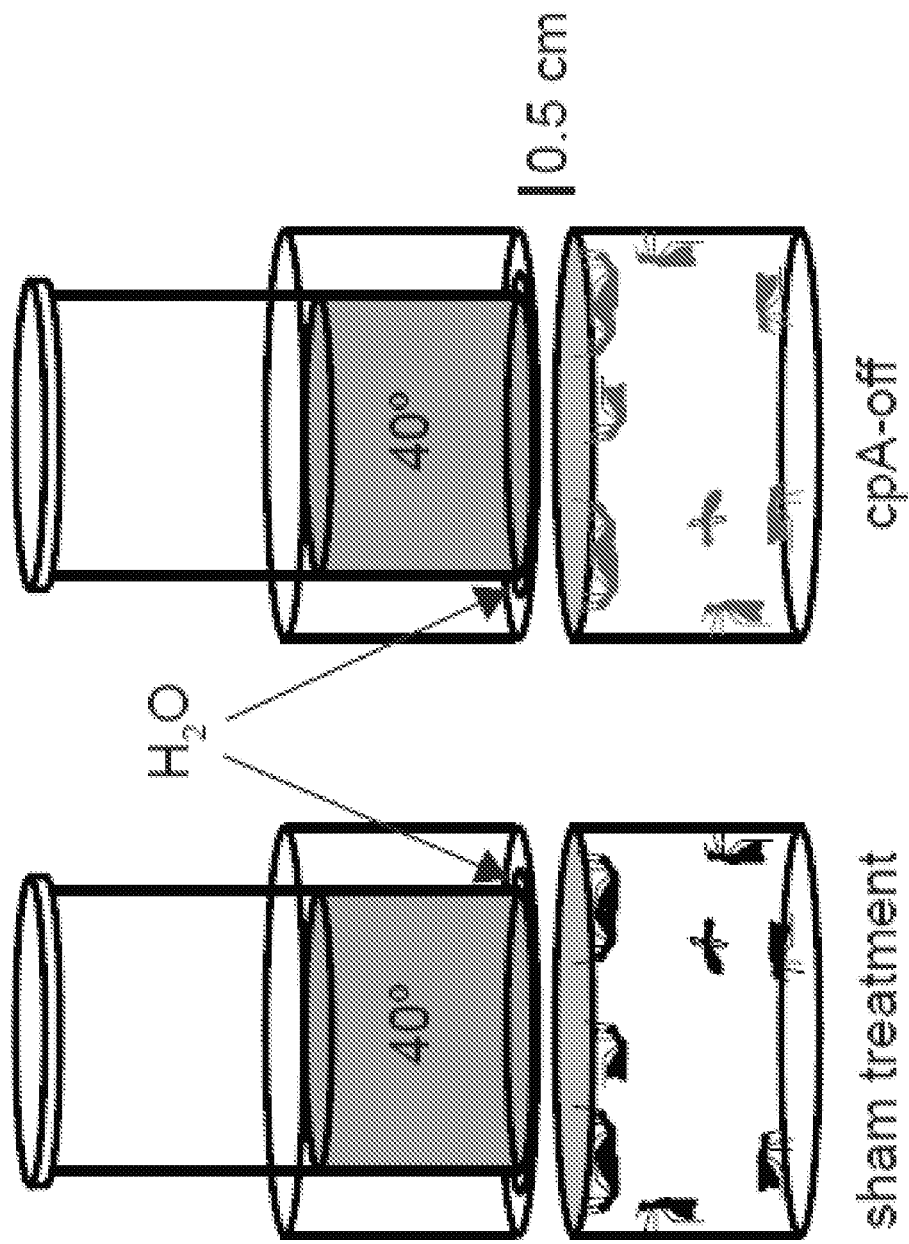
FIG. 9e is a schematic of the apparatus used to assay short-range attraction to heat and humidity.

Short-Range Attraction:

Ten 6-day-old female *A. aegypti* were starved 30 hrs in a 7 cm diameter×~5 cm high cage with wire mesh on one side and placed inside an aquarium. After 5 min a beaker with 750 ml warm water (40° C.) and filter paper soaked with 400 µl water were placed 5 mm above the cage (FIG. 9e). CpA-off and sham treated mosquitoes were video-recorded and counted at 30 s intervals.

Results

Figure 2A:
FIG. 2a is a comparison of chemical structures of butyraldehyde, butyric acid, and butyryl chloride.
Figure 2A:
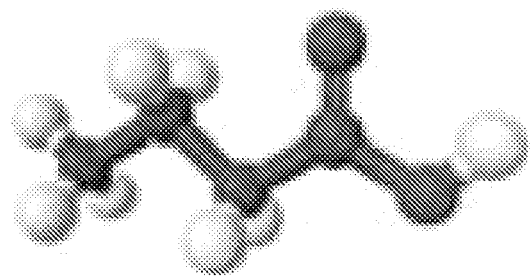
Figure 2A:
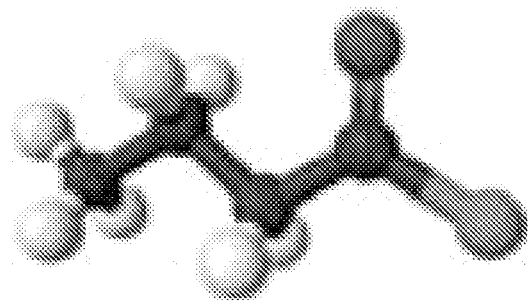
Figure 2B:
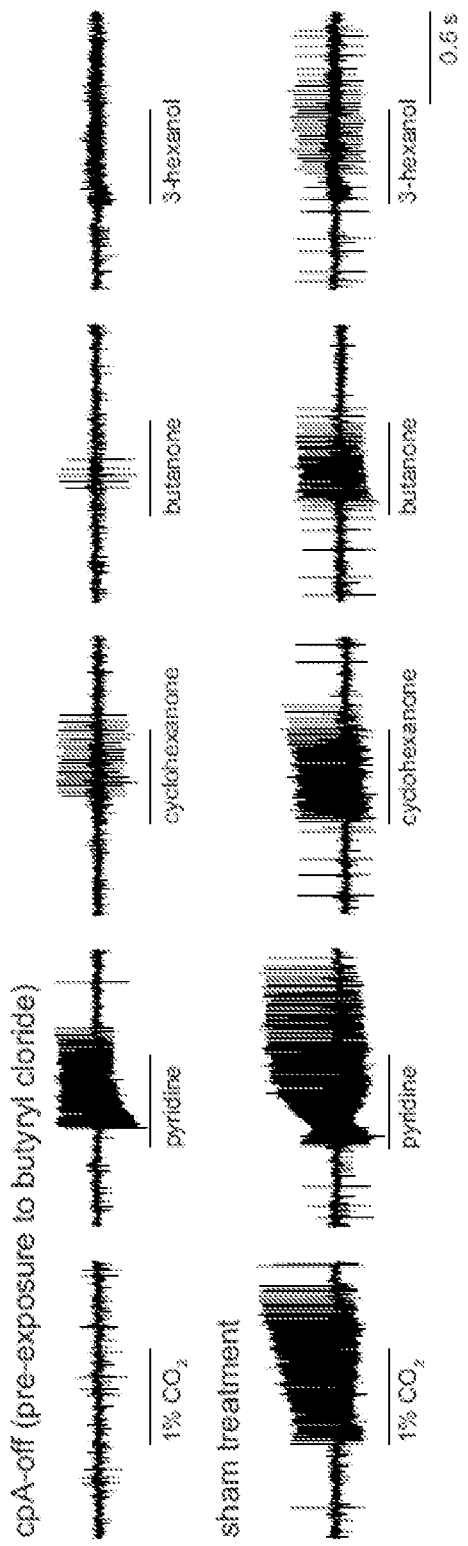
FIG. 2b depicts representative cp responses to 0.5-s pulses of indicated odorants after a 3-min pre-exposure to butyryl chloride ($10^{-2}$) (cpA-off) or solvent (sham treatment).
Figure 2C:
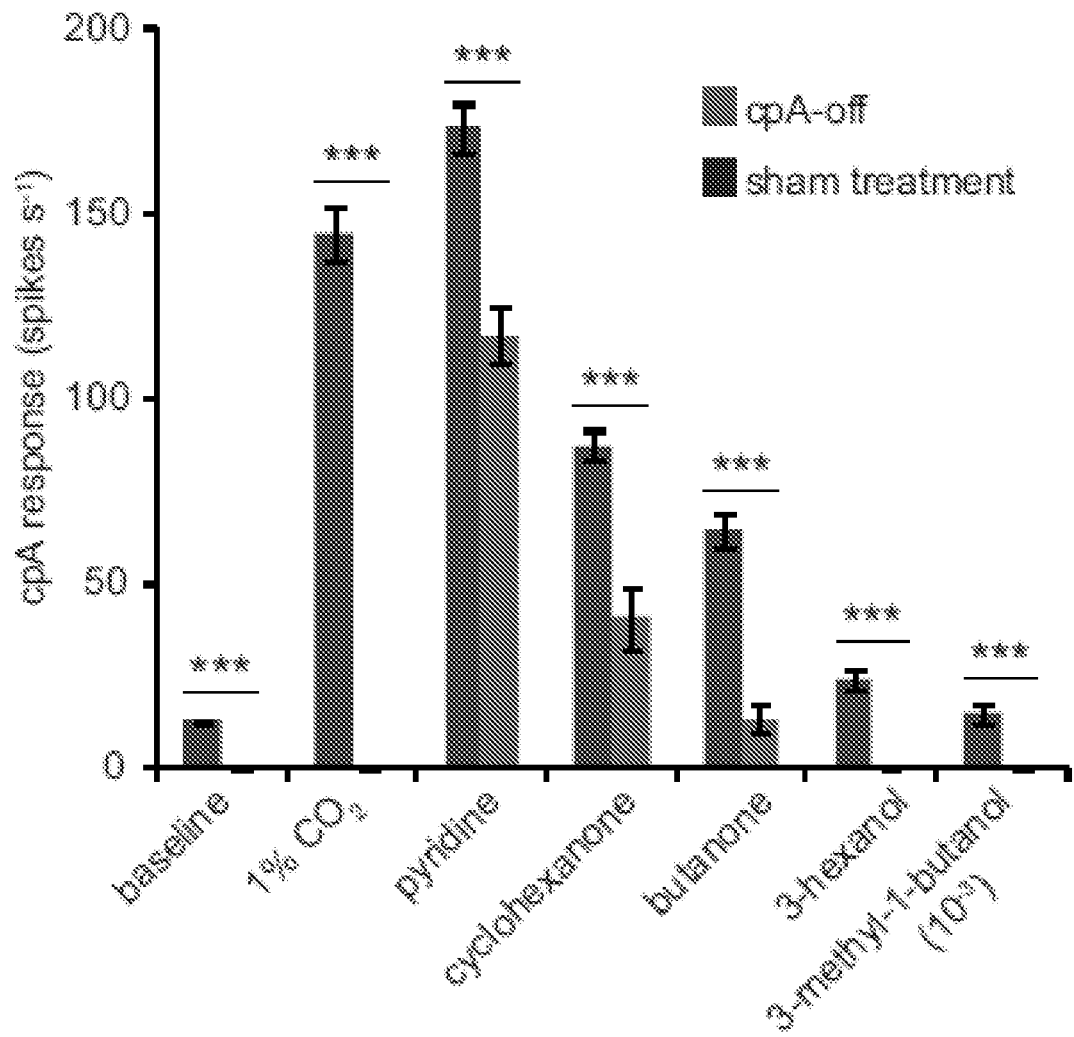
FIG. 2c is a bar graph illustrating the mean odorant-evoked responses of the cpA neuron in cpA-off and sham treated mosquitoes.

Butyryl chloride is a reactive volatile compound and is structurally related to two of the strongest known inhibitors of the $CO_2$ receptor, butyraldehyde and butanoic acid (FIG. 2a). A single puff of 1% butyryl chloride inhibits cpA from firing in response to subsequent $CO_2$ stimuli. Based on dose-response and time-response experiments, a 3-min exposure to a small quantity (100 l, 10$^{-2}$) of butyryl chloride volatiles in an upended glass dish was determined to completely abolished cpA's subsequent responses to 1% $CO_2$ (FIGS. 2b and 2c) or exhaled breath (not shown) when tested in a period ~5-20 min after exposure. The neuron's responses to activating skin odorants were also substantially reduced after this pre-exposure (FIGS. 2b and 2c). The inhibition of cpA was observed to be long-lasting and recovered to control levels between 12-24 hours after treatment (FIG. 9b).

Figure 2D:
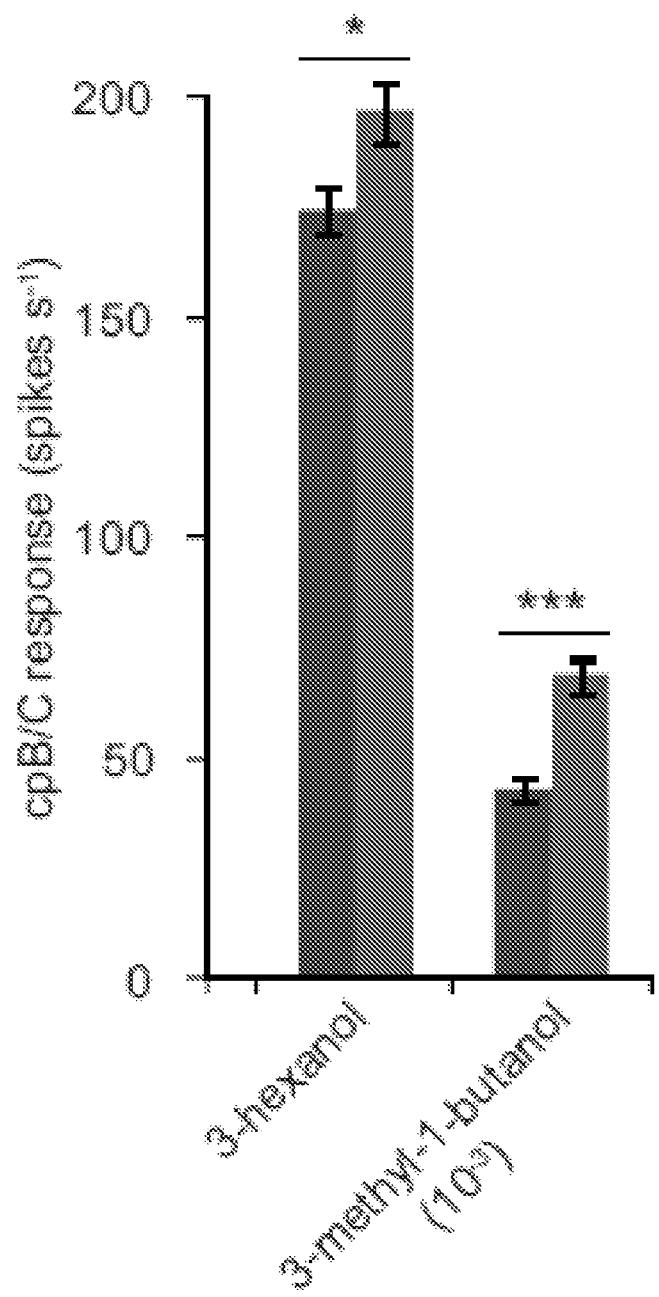
FIG. 2d is a bar graph illustrating the combined odor-evoked responses of two neighbouring neurons, cpB and cpC, where for both of these figures, n=6 individuals, 1-4 sensilla surveyed per individual; analysed by nested ANOVA, and baseline refers to cpA activity in the presence of room air.
Figure 2E:
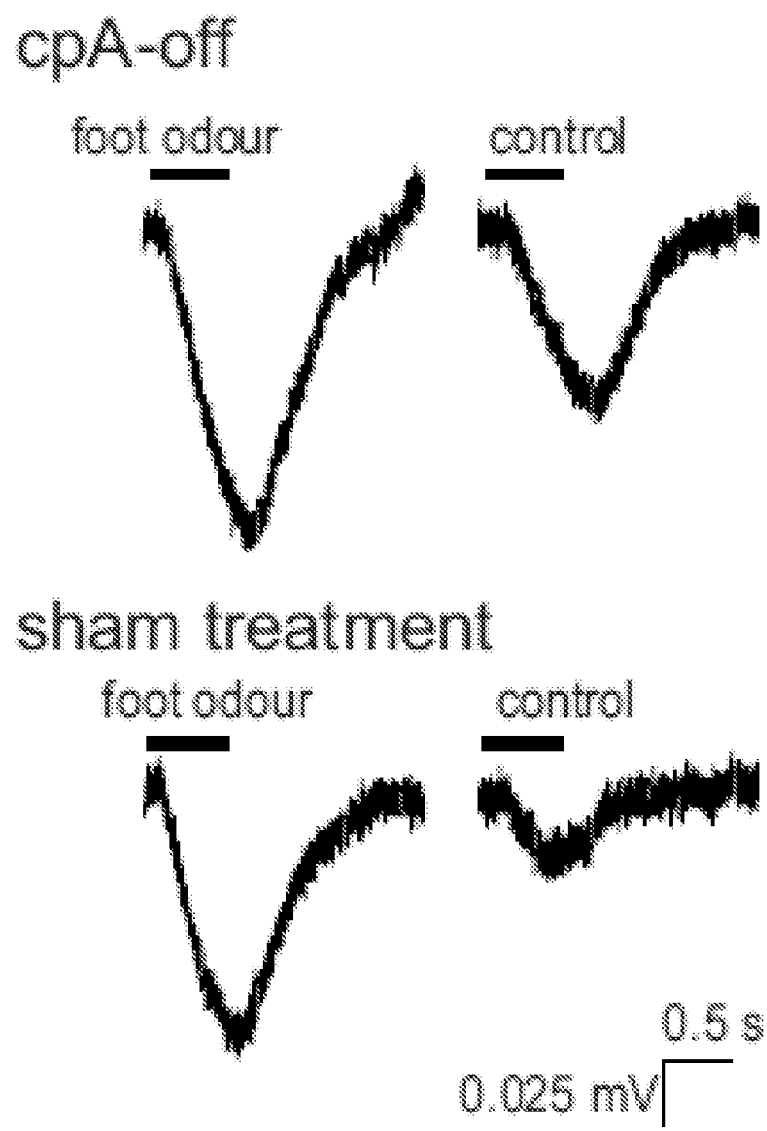
FIG. 2e is a graph illustrating averaged traces and FIG. 2f is a graph illustrating mean electroantennograph (EAG) responses to air puffed over glass beads laden with foot odor or a clean bead control, where EAG peaks are normalized to 3-methyl-1-butanol response, n=9, and analysed by t-test.
Figure 2F:
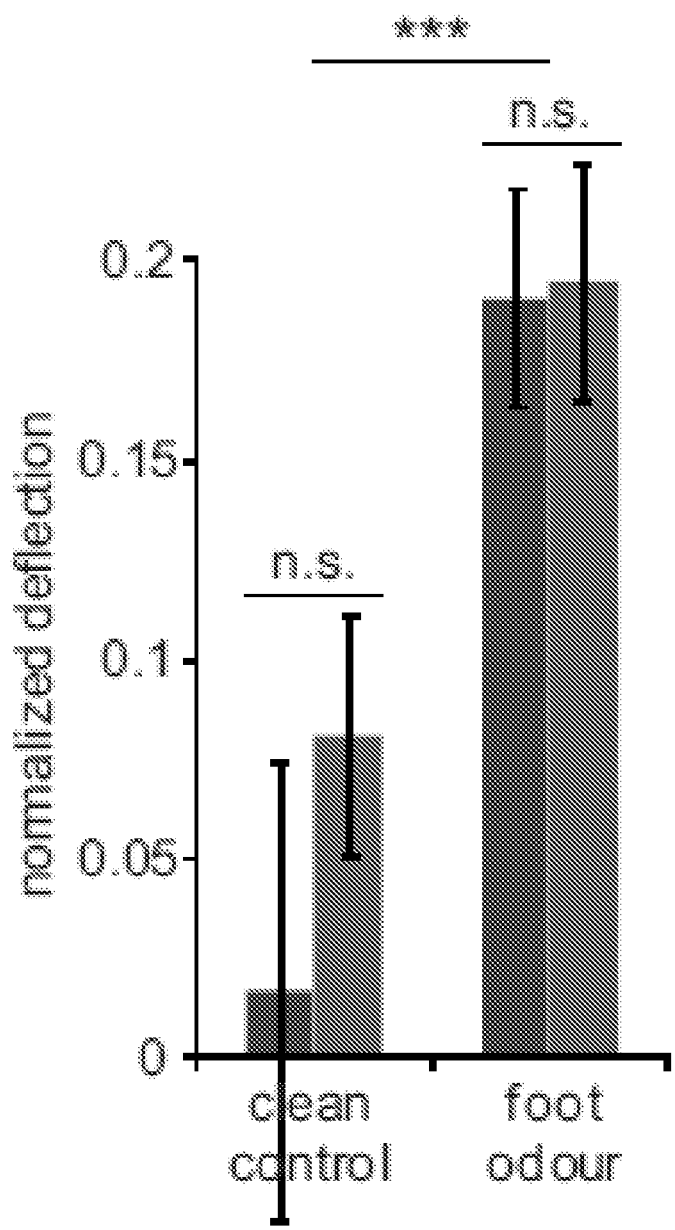

The observed effect is specific to the cpA neuron of the palp. Odor-evoked responses of the other two neurons in the same sensillum (cpB and cpC), which express members of the Or gene family, were not reduced after the treatment (FIG. 2d). In fact, these neurons showed a slight increase in activity. The summed response of antennal neurons to foot odor, with or without butyryl chloride treatment, was not statistically different in electroantennogram (EAG) recordings (FIGS. 2e and 2f). Likewise, the summed responses of antennal neurons to a panel of skin odorants, including those that have been previously implicated in host-seeking behaviour, was also unaffected by butyryl chloride treatment (FIG. 9c and FIG. 9d).

Figure 2G:
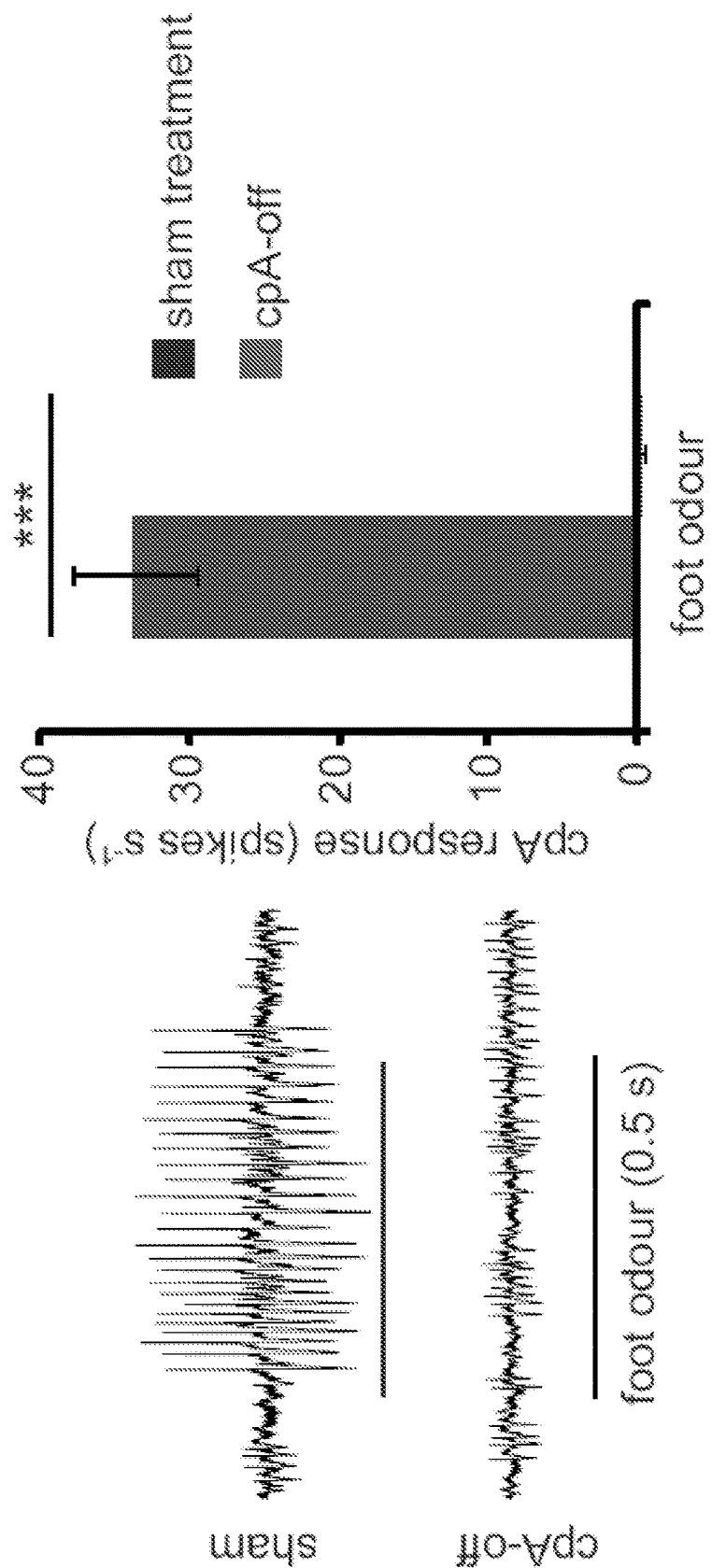
FIG. 2g depicts sample traces and mean cpA responses to 0.5-s pulses of foot odor (mixed beads from Person 1 and Person 2) in cpA-off and sham treated mosquitoes, in which n=4 individuals, 2-3 sensilla surveyed per individual, and analysed by nested ANOVA.
Figure 2H:
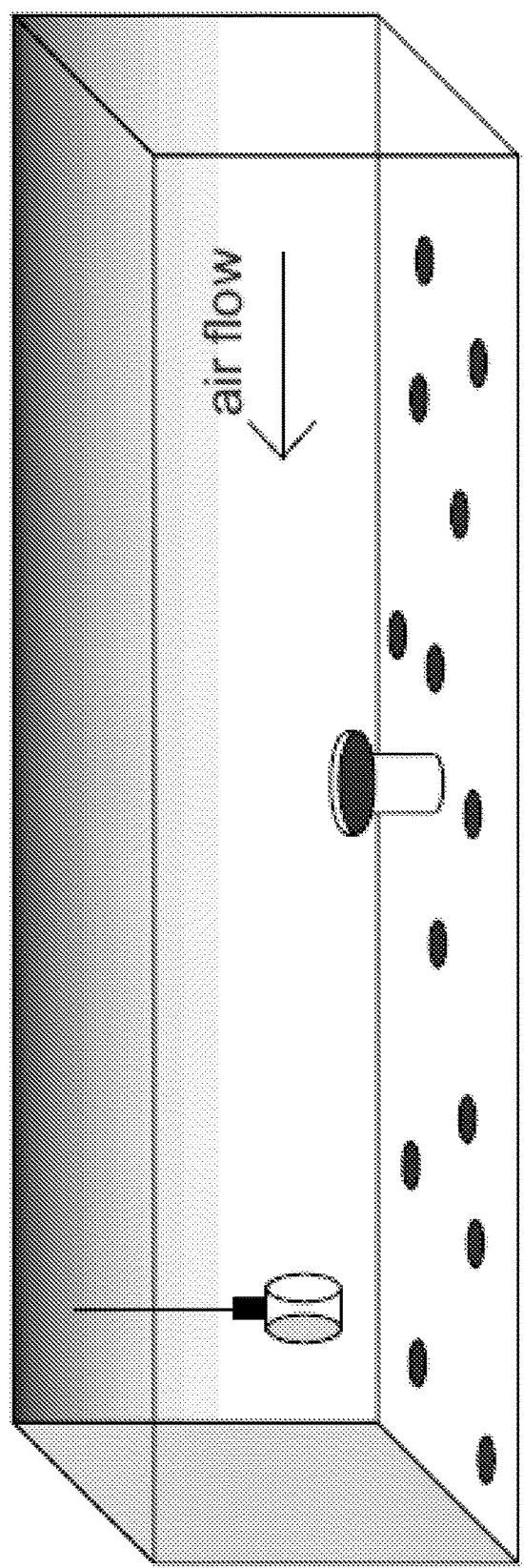
FIG. 2h is a schematic of wind tunnel assay, where human odor was provided by a dish of glass beads that had been worn in socks for ~6 hrs (Person 1), and flight behaviour of individual female mosquitoes was recorded for 5 min or until they landed on the beads.
Figure 2I:
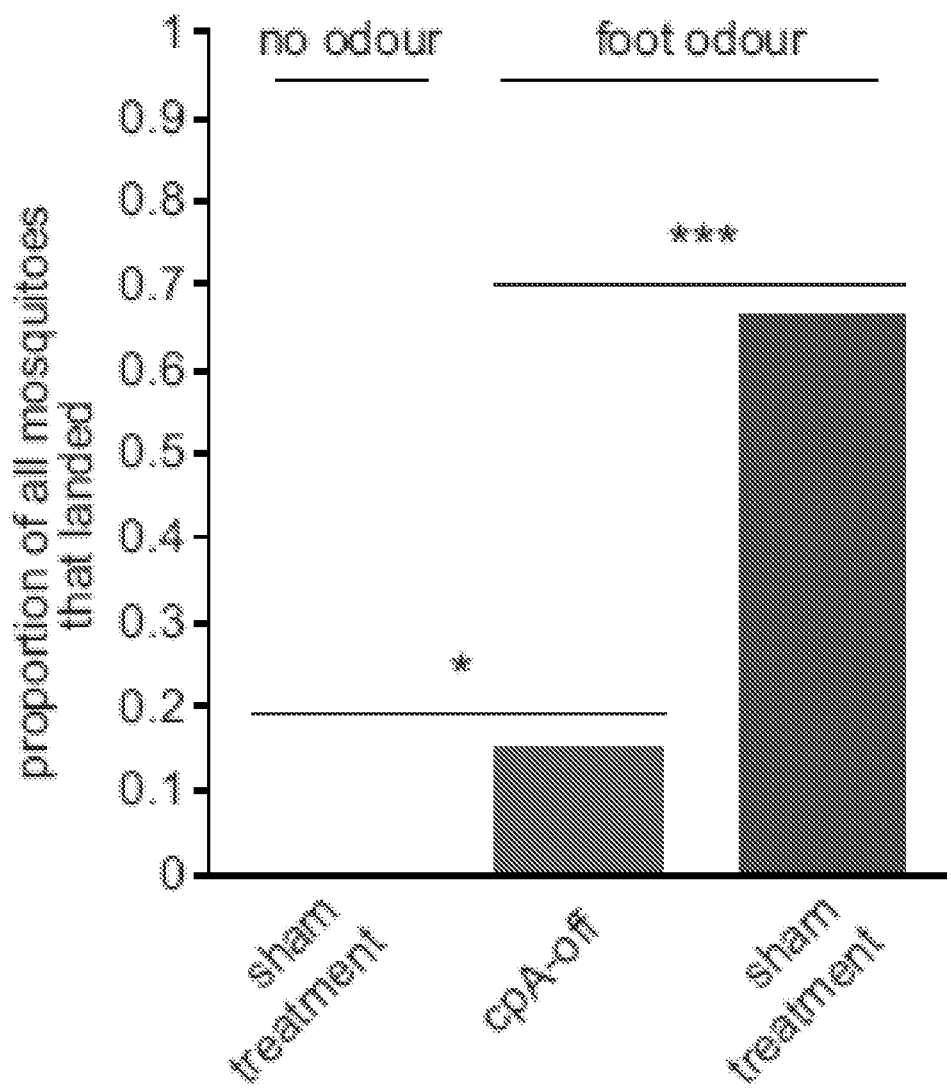
FIGS. 2i-k are bar graphs illustrating the proportion of butyryl chloride pre-exposed and sham treated mosquitoes presented with beads with no odor or foot odor that landed on beads (FIG. 2i), that took off from the release cage (FIG. 2j), and that did take off that succeeded in landing on the beads (FIG. 2k), where n=20-23 individuals per condition, analysed by one-tailed proportion Z-test, *p<0.05, p<0.01, *p<0.001, and error bars are s.e.m. All odorants except $CO_2$ were dissolved in paraffin oil at $10^{-2}$ except where indicated.
Figure 2J:
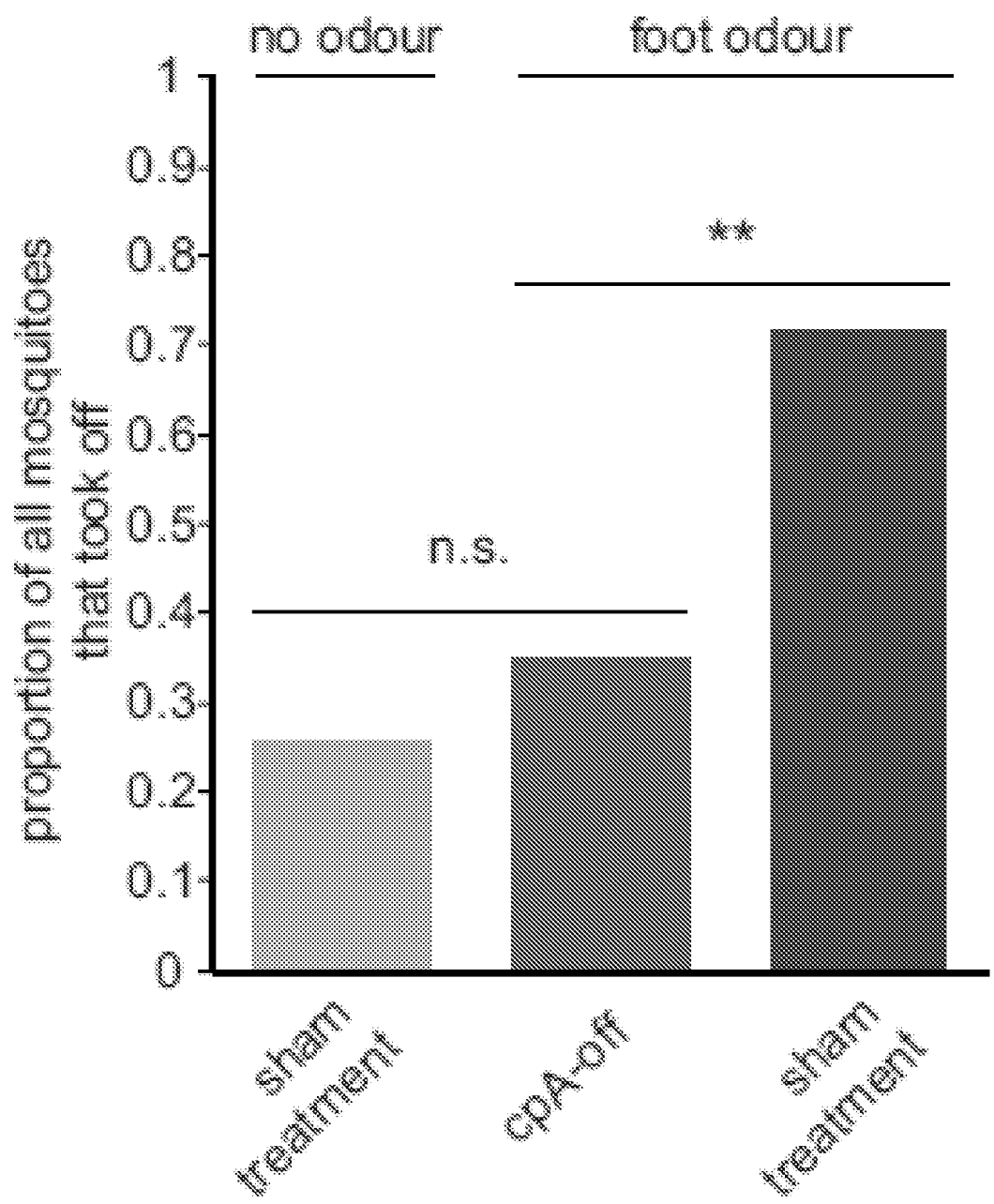

Moreover, the response of cpA to foot odor collected on beads was also completely lost when tested ~5-20 min after exposure (FIG. 2g). The ability to specifically shut down cpA responses provides a system to test whether the neuron is involved in attraction towards human skin odor. *A. aegypti* females were observed to initiate upwind flight, navigate upwind, and land on a dish of foot-odor beads presented in a wind tunnel even in the absence of a $CO_2$ plume (FIGS. 2h-2k). The proportion of mosquitoes that landed on the human odor beads was substantially reduced after pre-exposure to butyryl chloride (FIG. 2i). Analysis of flight videos indicated that the proportion of cpA-off mosquitoes that initiated upwind flight from the release cage was greatly reduced and indistinguishable from the proportion of control mosquitoes that initiated upwind flight in the absence of any human odor (FIG. 2j).

Figure 2K:
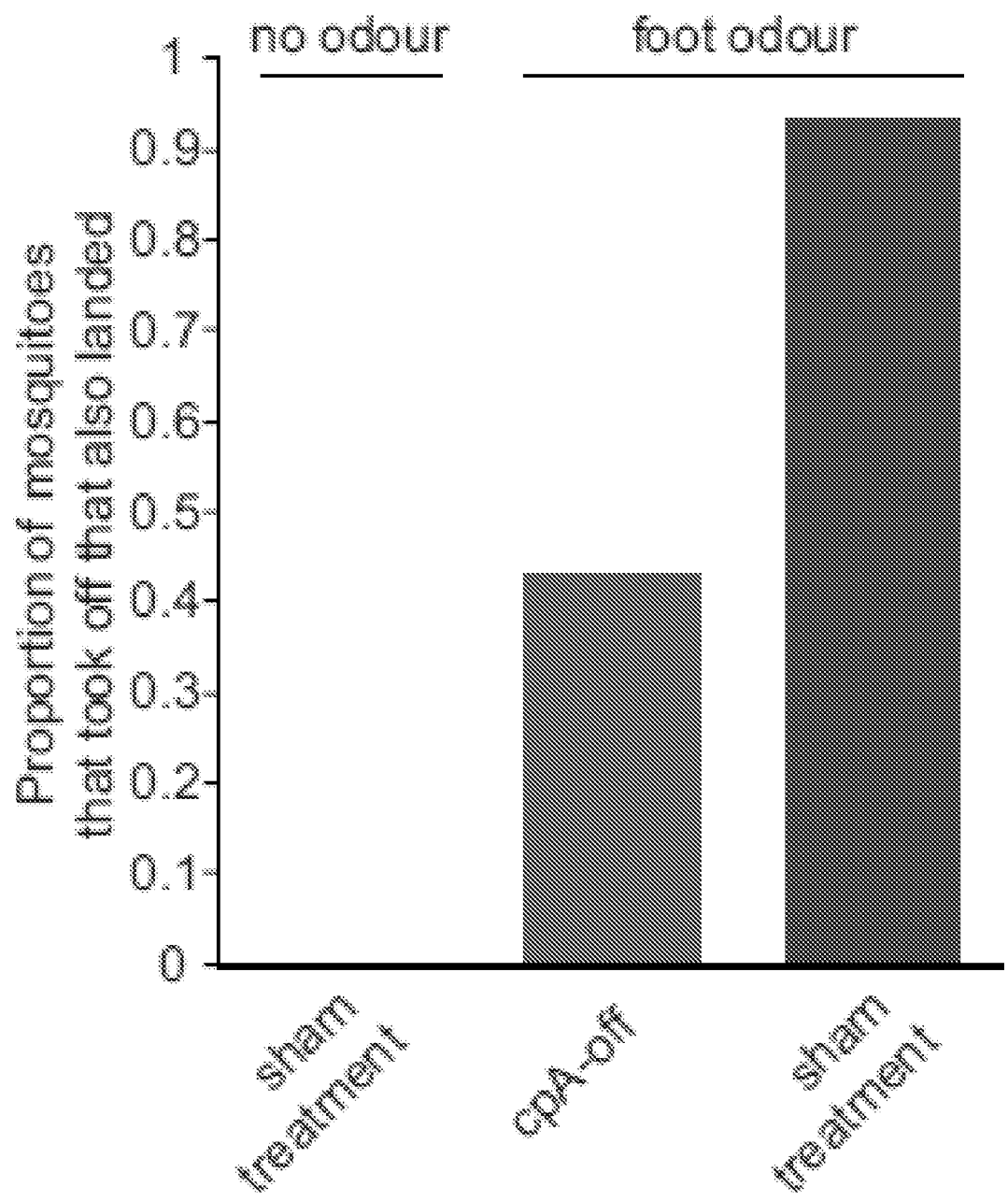
Figure 9F:
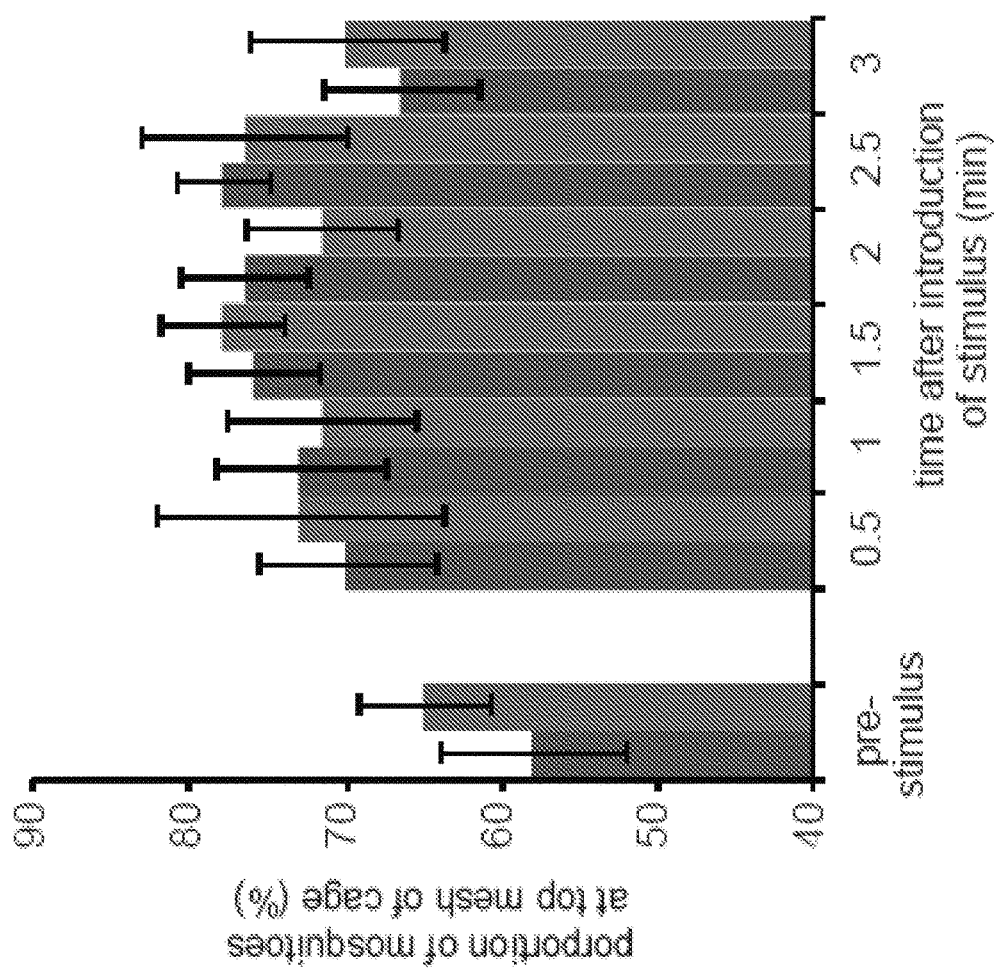
FIG. 9f illustrates mosquitoes' tendency to rest at the top surface of the cage increased in the presence of a warm, wet stimulus. Mosquitoes in each treatment group were observed to probe through the mesh with their proboscides when stimulus was present. No significant differences due to treatment (n=6 replicates; Mann-Whitney rank-sum test).
Figure 10A:
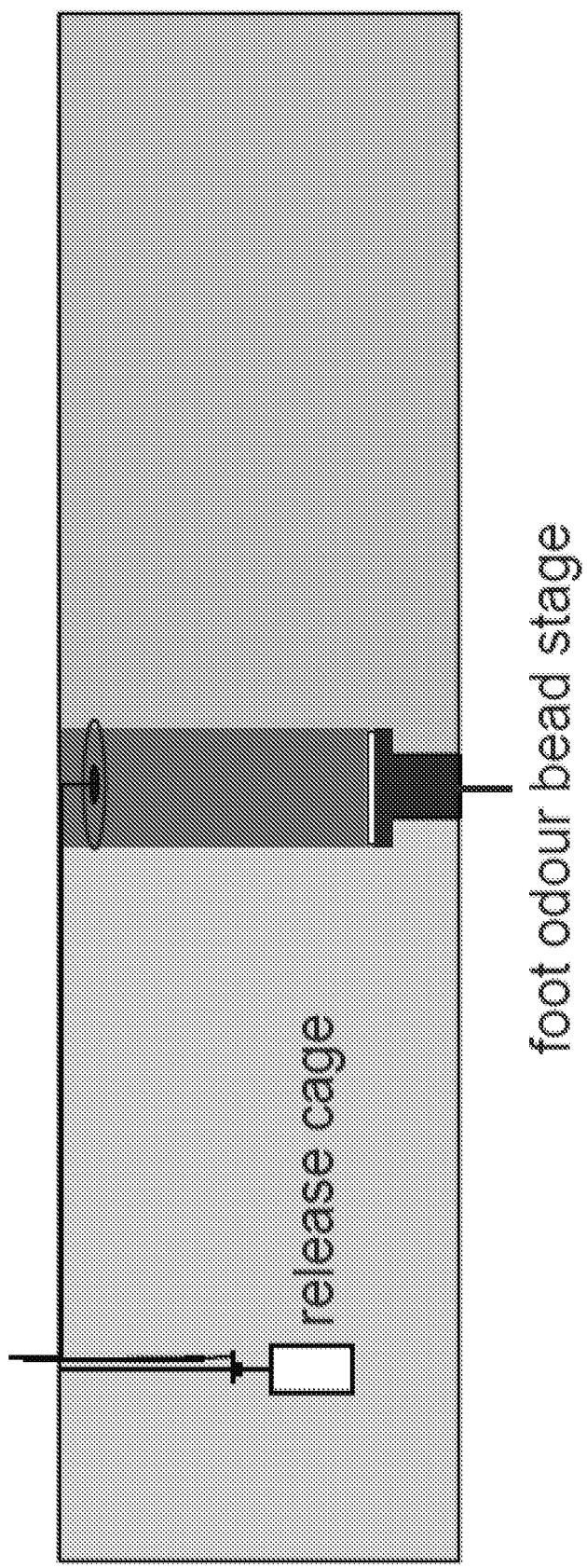
FIG. 10a is a schematic of the wind tunnel used in the wind tunnel assays showing the mosquito release chamber, human foot odor bead stage, and retracted bead cover.
Figure 10B:
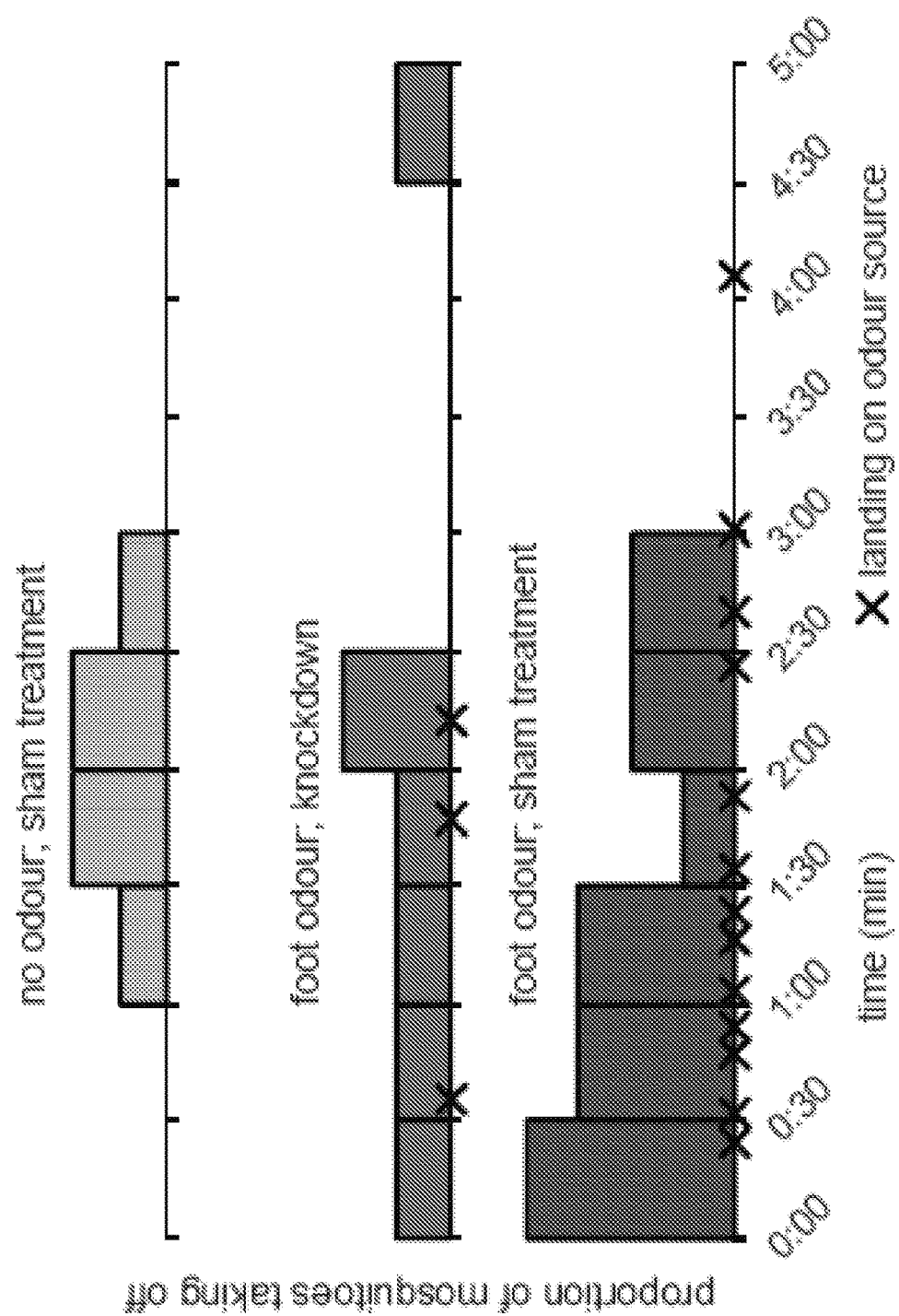
FIG. 10b shows histograms quantifying the number of mosquitoes that took off during the 5-minute assay in each of three experimental conditions. Heights of bars are proportional across all three histograms. X's mark when a mosquito landed on the odor source.
Figure 10C:
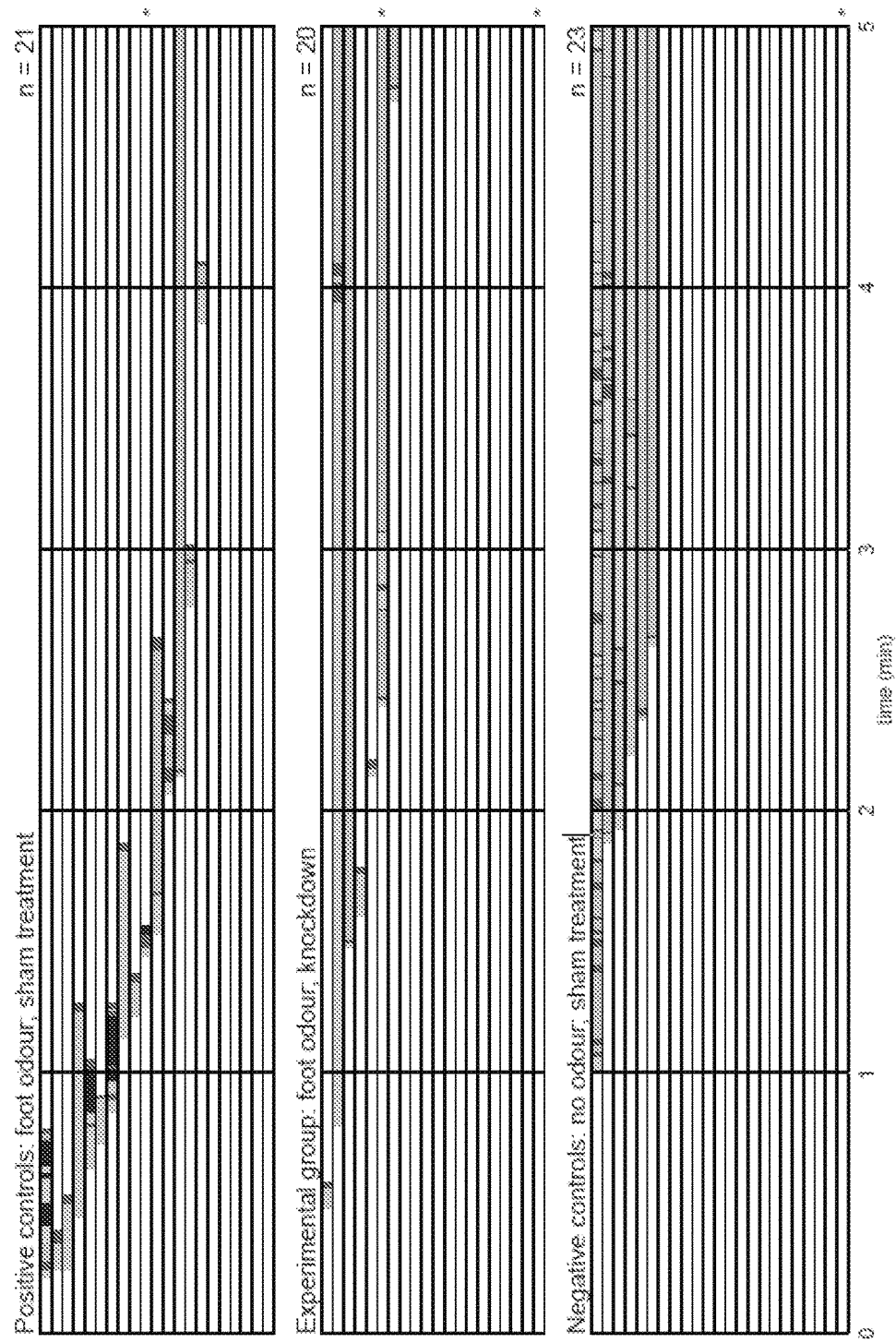
FIG. 10c shows plots where each row indicates flight behavior of each individual mosquito assayed. Shaded areas on each line represent time between when the mosquito left the release cage and when it landed on the beads or the assay ended at 5 min. Colors correspond to where the mosquito was located in the wind tunnel (as indicated in FIG. 10a) at each moment.

Most sham-treated control mosquitoes took off relatively quickly towards foot odor, but the cpA-off mosquitoes that did take off did so throughout the five-minute period of the assay (FIG. 10). CpA-off mosquitoes that did take off from the release cage showed no deficit in ability to fly (FIG. 10). Of these, less than half successfully navigated to or landed on the beads; the behaviour of others resembled that of no-odor controls (FIG. 2k, FIG. 10). Residual landing behaviour observed in treated mosquitoes may be mediated by short-range cues that are detected by other olfactory neurons or due to incomplete shutdown of the cpA neuron in tested individuals. In a separate control assay, pre-exposure to butyryl chloride did not impair mosquitoes' ability or preference for resting at the top of a small cage, or the increase in this preference when a warm, moist stimulus was introduced above the cage (FIG. 9e and FIG. 9f), which suggests that general physical or behavioural deficits are unlikely. Taken together, these results show that the highly conserved $CO_2$ receptor-containing neuron detects human skin odorants and mediates attraction towards skin odor.

Example 3

In Silico Identification of cpA Activators and Inhibitors for Human Use

Figure 3A:
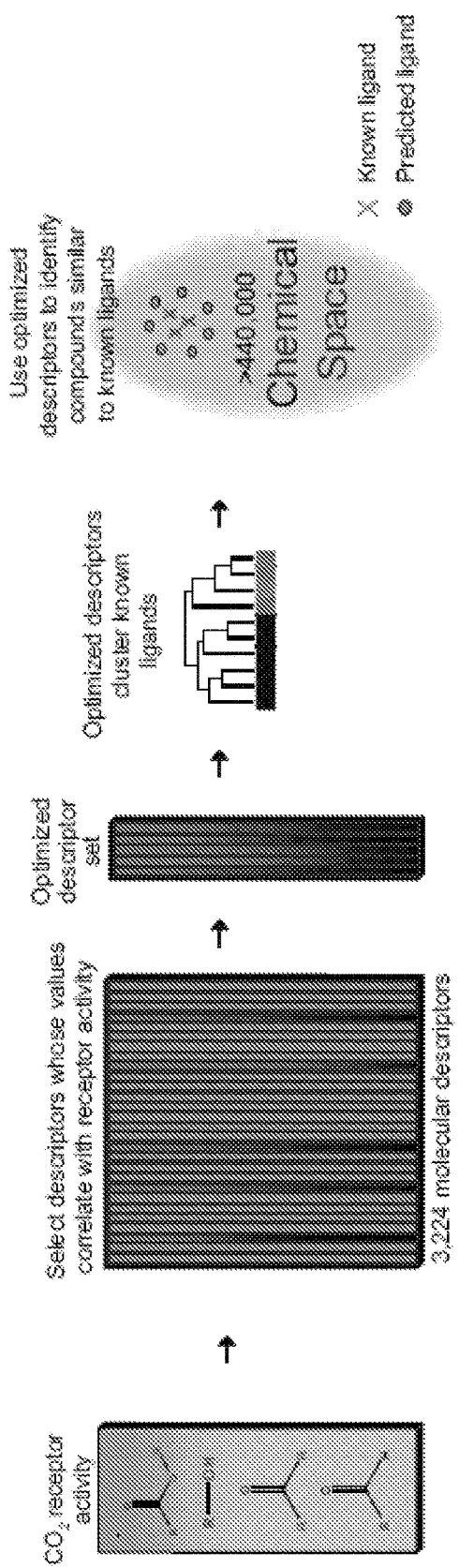
FIG. 3a is a schematic providing an overview of the cheminformatics method used to identify novel cpA ligands from a large untested chemical space.

In this Example, ligands that have stronger effects on cpA activity are identified using an in silico screen. Such ligands are pleasant smelling, safe, and affordable. Using cheminformatics, structural features shared amongst known ligands (inhibitors and activators) of the $CO_2$-sensitive neuron were identified and a structure comparison approach was used to identify new ligands from an extremely large chemical space (>440,000, including 3,197 volatiles from natural sources) (FIG. 3a).

Existing data on odor-evoked activity for the cpA neuron that expresses the conserved $CO_2$ receptor from *A. aegypti*, *A. gambiae*, and *Culex quinquefasciatus* as well as *Drosophila melanogaster* was compiled to generate training sets for cheminformatic analysis. Known ligands fell into multiple structural classes, suggesting the possibility of distinct binding pockets on the receptor. In order to improve chances of identifying structural features for these potentially distinct binding sites, active compounds were separated into three training sets: aromatic/cyclic ligands, straight-chain ligands, and ligands from both sets together.

A single energy-minimized 3D structure was obtained for each odor in the training set and the values for 3,224 molecular descriptors from Dragon (Talete) were calculated. A small subset of molecular descriptors whose values were highly correlated with electrophysiological activity was selected through application of a Sequential Forward Selection method. This process was applied independently for each of the training sets, resulting in three separate activity-optimized molecular descriptor sets (Tables 2a, 2b and 2c below). 3D and 2D molecular descriptors were preferentially selected, suggesting that shape-related features were important for interaction with the receptor.

TABLE 2a

Aromatic/cyclic optimized descriptors

| symbol | breif description | class | dimensionality | occurrence |
|---|---|---|---|---|
| N.075 | R—N—R/R—N—X | atom-centered fragments | 2 | 1 |
| R3v. | R maximal autocorrelation of lag 3/ weighted by atomic van der Waals volumes | GETAWAY descriptors | 3 | 1 |
| H.049 | H attached to C3(sp3)/C2(sp2)/C3(sp2)/C3(sp) | atom-centered fragments | 2 | 1 |
| nRCHO | number of aldehydes (aliphatic) | functional group counts | 1 | 1 |
| nN | number of Nitrogen atoms | constitutional descriptors | 1 | 1 |
| ISH | standardized information content on the leverage equality | GETAWAY descriptors | 3 | 1 |
| EEig07d | Eigenvalue 07 from edge adj. matrix weighted by dipole moments | edge adjacency indices | 2 | 1 |
| piPC04 | molecular multiple path count of order 04 | walk and path counts | 2 | 1 |
| MATS4e | Moran autocorrelation - lag 4/ weighted by atomic Sanderson electronegativities | 2D autocorrelations | 2 | 1 |
| ESpm14d | Spectral moment 14 from edge adj. matrix weighted by dipole moments | edge adjacency indices | 2 | 1 |
| Mor12m | 3D-MoRSE - signal 12/weighted by atomic masses | 3D-MoRSE descriptors | 3 | 1 |

TABLE 2b

Combined-ligands optimized descriptors

| symbol | breif description | class | dimensionality | occurrence |
|---|---|---|---|---|
| HNar | Narumi harmonic topological index | topological descriptors | 2 | 1 |
| R3v+ | R maximal autocorrelation of lag 3/weighted by atomic van der Waals volumes | GETAWAY descriptors | 3 | 4 |
| HATS3m | leverage-weighted autocorrelation of lag 3/weighted by atomic masses | GETAWAY descriptors | 3 | 1 |
| Mor13p | 3D-MoRSE - signal 13/ weighted by atomic polarizabilities | 3D-MoRSE descriptors | 3 | 1 |
| ISH | standardized information content on the leverage equality | GETAWAY descriptors | 3 | 2 |
| P1s | 1st component shape directional WHIM index/weighted by atomic electrotopological states | WHIM descriptors | 3 | 1 |
| R4e+ | R maximal autocorrelation of lag 4/weighted by atomic Sanderson electronegativities | GETAWAY descriptors | 3 | 1 |
| nRCHO | Number of aldehydes (aliphatic) | functional group counts | 1 | 2 |

TABLE 2b-continued

Combined-ligands optimized descriptors

| symbol | breif description | class | dimensionality | occurrence |
|---|---|---|---|---|
| JG12 | Mean topological charge indext of order2 | topological charge indices | 2 | 2 |
| E1u | 1st component accessibility directional WHIM index/ unweighted | WHIM descriptors | 3 | 2 |
| MATS5m | Moran autocorrelation - lag 5/ weighted by atomic masses | 2D autocorrelations | 2 | 1 |
| STN | spanning tree number (log) | topological descriptors | 2 | 2 |
| DISPe | D COMMA2 value/weighted by atomic Sanderson electronegativities | geometrial descriptors | 3 | 1 |
| B06.C.O. | presence/absence of C—O at topological distance 06 | 2D binary fingerprints | 2 | 1 |
| X4A | average connectivity index chi-4 | connectivity indices | 2 | 4 |
| JG13 | mean topological charge index of order3 | topological charge indices | 2 | 1 |
| De | D total accessibility index/ weighted by atomic Sanderson electronegativities | WHIM descriptors | 3 | 2 |
| Mor25u | 3D-MoRSE - signal 25/ unweighted | 3D-MoRSE descriptors | 3 | 1 |
| nRCOX | number of acyl halogenides (aliphatic) | functrional group counts | 1 | 1 |
| B03.O.O. | presence/absence of O-O at topological distance 03 | 2D binary fingerprints | 2 | 1 |
| nHDon | number of donor atoms for H-bonds (N and O) | functional group counts | 1 | 1 |
| MATS3e | Moran autocorrelation - lag 3/ weighted by atomic Sanderson electronegativities | 2D autocorrelations | 2 | 1 |
| RBF | rotable bond fraction | constitutional descriptors | 2 | 1 |
| GATS5m | Geary autocorrelation - lag 5/ weighted by atomic masses | 2D autocorrelations | 2 | 1 |
| C.008 | CHR2X | atom-centered fragments | 2 | 1 |
| Mor13v | 3D-MoRSE - signal 13/ weighted by atomic van der Waals volumes | 3D-MoRSE descriptors | 3 | 1 |
| R6u. | R maximal autocorrelation of lag 6/unweighted | GETAWAY descriptors | 3 | 1 |

TABLE 2c

Aliphatic optimized descriptors

| symbol | brief description | class | dimensionality | occurrence |
|---|---|---|---|---|
| ATS1p | Broto-Moreau autocorrelation of lag 1 (log function) weighted by polarizability | 2D autocorrelations | 2 | 1 |
| Gu | total symmetry index/unweighted | WHIM descriptors | 3 | 6 |
| PW5 | path/walk 5 - Randic shape index | Topological indices | 2 | 1 |
| H-052 | H attached to C0(sp3) with 1X attached to next C | Atom-centered fragments | 2 | 4 |
| H4m | H autocorrelation of lag 4/ weighted by mass | GETAWAY descriptors | 3 | 3 |
| Rtu+ | R total index/unweighted | GETAWAY descriptors | 3 | 3 |
| HATS6m | leverage-weighted autocorrelation of lag 6/weighted by mass | GETAWAY descriptors | 3 | 3 |
| B03[C—O] | Presence/absence of C—O at topological distance 3 | 2D Atom Pairs | 2 | 1 |
| nR=Cs | number of aliphatic secondary C(sp2) | Functional group counts | 1 | 2 |
| EEig09r | Eigenvalue 09 from edge adj. matrix weighted by resonance integrals | edge adjacency indices | 2 | 1 |

TABLE 2c-continued

Aliphatic optimized descriptors

| symbol | brief description | class | dimensionality | occurrence |
|---|---|---|---|---|
| Mor16m | 3D-MoRSE - signal 16/weighted by atomic masses | 3D-MoRSE descriptors | 3 | 3 |
| X5A | average connectvity index chi-5 | connectivity indices | 2 | 1 |
| EEig02r | Eigenvalue 02 from edge adj. matrix weighted by resonance integrals | edge adjacency indices | 2 | 2 |
| RDF055m | Radial Distribution Function - 5.5/ weighted by atomic masses | RDF descriptors | 3 | 1 |
| EEig04d | Eigenvalue 04 from edge adj. matrix weighted by dipole moments | edge adjacency indices | 2 | 2 |
| B06[C-C] | presence/absence of C-C at topological distance 06 | 2D binary fingerprints | 2 | 1 |
| JG14 | mean topological charge index of order4 | topological charge indices | 2 | 1 |
| RDF085m | Radial Distribution Function - 8.5/ weighted by atomic masses | RDF descriptors | 3 | 1 |
| Mor08u | 3D-MoRSE - signal 08/ unweighted | 3D-MoRSE descriptors | 3 | 1 |
| MATS5e | Moran autocorrleation - lag 5/ weighted by atomic Sanderson electronegativities | 2D autocorrelations | 2 | 2 |
| B02[C-C] | presence/absence of C-C at topological distance 02 | 2D binary fingerprints | 2 | 1 |
| nCrs | number of ring secondary C(sp3) | functional group counts | 1 | 1 |
| X4Av | average valence connectivity index chi-4 | connectivity indices | 2 | 1 |
| R7e+ | R maximal autocorrelation of lag 7/ weighted by atomic Sanderson electronegativities | GETAWAY descriptors | 3 | 1 |
| EEig08r | Eigenvalue 08 from edge adj. matrix weighted by resonance integrals | edge adjacecy indices | 2 | 1 |
| E3s | 3rd component accessibility directional WHIM index/weighted by atomic electrotopological states | WHIM descriptors | 3 | 1 |

The library of >440,000 chemicals by their computationally determined similarity to known ligands using the three optimized descriptor sets and generated three lists of predicted ligands that cumulatively represent numerous potential ligands for the $CO_2$ receptor-expressing cpA neuron.

Example 4

Predicted Ligands Contain Effective Activators, Inhibitors, and an Ultra-Prolonged Activator From the large list of cpA receptor ligands predicted from Example 3 above, 138 compounds were selected based on desirable criteria for application such as smell, presence in natural sources, human safety profile, and cost to procure. These compounds were tested individually using single-sensillum electrophysiology on the cp sensillum of female *A. aegypti*, according to the procedure described in Example 1 above.

Figure 3B:
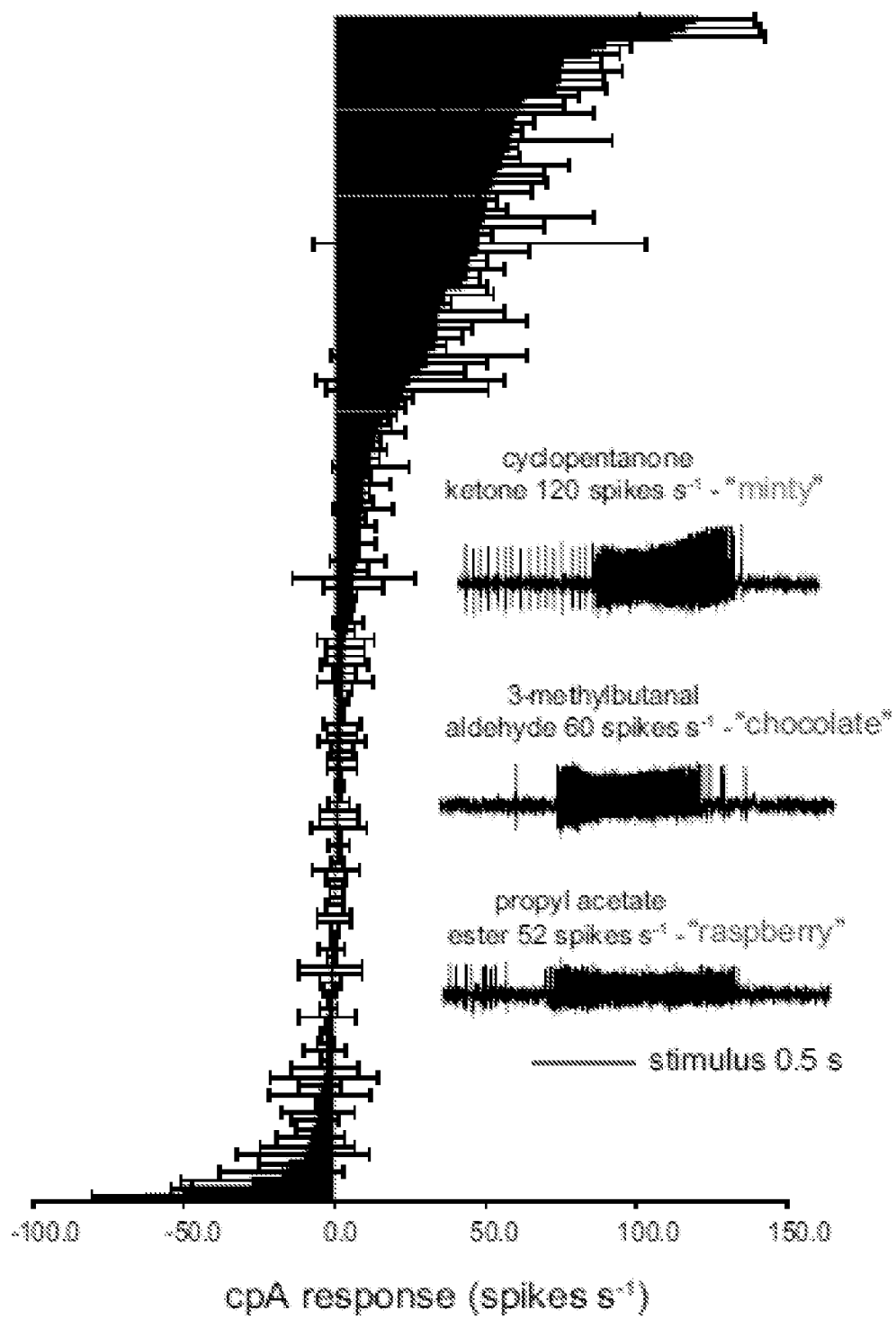
FIG. 3b depicts representative traces and mean responses of the A. aegypti cpA neuron to 0.5-s pulses of 138 predicted compounds screened using single-sensillum recordings, in which odorants were diluted to $10^{-2}$ in paraffin oil or water, and responses to solvent have been subtracted, n=2-6, and error bars are s.d.

Approximately 30% of the tested odors activated the cpA neuron with >30 spikes $s^{-1}$ (FIG. 3b). To our satisfaction, ~85% of these activators are already approved for use as flavor, fragrance, or cosmetic agents and many have been listed in "generally recognized as safe" (GRAS) list by the Flavor and Extract Manufacturer's Association (Table 3 below).

TABLE 3

List of tested odors

| IUPAC | Activation (spikes $s^{-1}$) | s.d. | N | % Inhibition | s.d | N |
|---|---|---|---|---|---|---|
| Cyclopentanone | 120.1 | 19.0 | 5 | n/d | n/d | n/d |
| Thiophene | 116.6 | 24.4 | 5 | n/d | n/d | n/d |
| 4-methyl-1,3-thiazole | 111.8 | 30.8 | 5 | n/d | n/d | n/d |
| 1H-pyrrole | 89.8 | 8.4 | 5 | n/d | n/d | n/d |
| furan-3-carbaldehyde | 85.0 | 9.4 | 5 | n/d | n/d | n/d |
| 3-methylbutanenitrile | 75.8 | 12.4 | 5 | n/d | n/d | n/d |
| methyl propanoate | 75.0 | 20.2 | 5 | n/d | n/d | n/d |
| propane-1-thiol | 75.0 | 14.0 | 5 | n/d | n/d | n/d |
| dimethyl carbonate | 73.6 | 16.3 | 5 | n/d | n/d | n/d |
| hex-5-en-2-one | 63.4 | 17.7 | 5 | n/d | n/d | n/d |
| ethyl acetate | 62.4 | 13.7 | 5 | n/d | n/d | n/d |
| 3-methylbutanal | 60.2 | 25.9 | 5 | n/d | n/d | n/d |

TABLE 3-continued

List of tested odors

| IUPAC | Activation (spikes s$^{-1}$) | s.d. | N | % Inhibition | s.d | N |
|---|---|---|---|---|---|---|
| (E)-2-methylbut-2-enal | 59.5 | 6.4 | 2 | n/d | n/d | n/d |
| cyclohexanol | 59.0 | 2.8 | 2 | n/d | n/d | n/d |
| 2-methyloxolan-3-one | 58.4 | 33.5 | 5 | n/d | n/d | n/d |
| propyl formate | 58.0 | 2.8 | 2 | n/d | n/d | n/d |
| 5-methyl-3H-furan-2-one | 56.0 | 5.7 | 2 | n/d | n/d | n/d |
| 3-methylbut-2-enal | 55.5 | 21.9 | 2 | n/d | n/d | n/d |
| 1-methylpyrrole | 54.2 | 15.3 | 3 | n/d | n/d | n/d |
| propyl acetate | 52.6 | 17.8 | 5 | n/d | n/d | n/d |
| 3-methylbutan-1-ol | 51.8 | 13.8 | 5 | n/d | n/d | n/d |
| 5-ethenyl-4-methyl-1,3-thiazole | 50.5 | 3.5 | 2 | n/d | n/d | n/d |
| pentan-1-ol | 50.5 | 6.4 | 2 | n/d | n/d | n/d |
| prop-2-enyl propanoate | 49.5 | 36.1 | 2 | n/d | n/d | n/d |
| methyl 2-methylpropanoate | 49.4 | 19.9 | 5 | n/d | n/d | n/d |
| 2-methylfuran | 48.0 | 4.2 | 2 | n/d | n/d | n/d |
| 2-methylpropyl formate | 48.0 | 55.2 | 2 | n/d | n/d | n/d |
| cyclopentylmethanol | 47.5 | 17.0 | 3 | n/d | n/d | n/d |
| methyl 2-methylprop-2-enoate | 45.0 | 5.7 | 2 | n/d | n/d | n/d |
| methyl butanoate | 44.5 | 12.0 | 2 | n/d | n/d | n/d |
| 3-methylphenol | 44.0 | 4.2 | 2 | n/d | n/d | n/d |
| 3-ethylpyridine | 42.5 | 7.8 | 2 | n/d | n/d | n/d |
| 2-methylpropane-1-thiol | 37.0 | 15.6 | 2 | −2.9 | 2.7 | 2 |
| 2-methylpent-2-enal | 36.5 | 2.1 | 2 | 0.7 | 2.0 | 2 |
| 2-ethylpyrazine | 34.5 | 21.9 | 2 | −10.6 | 4.0 | 2 |
| ethyl formate | 34.5 | 29.0 | 2 | 0.7 | 4.0 | 2 |
| 4-methylpent-3-en-2-one | 34.0 | 11.3 | 2 | −5.5 | 3.7 | 2 |
| 4-propylpyridine | 34.0 | 8.5 | 2 | −4.3 | 3.0 | 2 |
| 2-methylbutanal | 33.5 | 3.5 | 2 | 0.0 | 5.0 | 2 |
| 3-methylcyclopent-2-en-1-one | 31.0 | 32.5 | 2 | −15.6 | 7.0 | 2 |
| (E)-hex-2-en-1-ol | 31.0 | 19.8 | 2 | 0.0 | 1.0 | 2 |
| 2-methylpropanal | 29.0 | 14.2 | 3 | 5.8 | 3.3 | 2 |
| butane-2,3-dithiol | 25.0 | 31.1 | 2 | −4.3 | 2.9 | 2 |
| 4-methylpentan-2-ol | 24.0 | 26.9 | 2 | −18.7 | 17.4 | 2 |
| 3-methylcyclohex-2-en-1-ol | 23.0 | 2.8 | 2 | −7.7 | 5.9 | 2 |
| ethyl (E)-but-2-enoate | 22.0 | 1.4 | 2 | −3.0 | 0.1 | 2 |
| 2-methylbenzaldehyde | 19.0 | 1.4 | 2 | −6.4 | 1.9 | 2 |
| prop-2-enyl butanoate | 16.0 | 2.8 | 2 | 3.4 | 2.0 | 2 |
| 2,6-dimethylpyrazine | 14.8 | 8.5 | 3 | −0.4 | 0.5 | 2 |
| 2-ethyl-5(6)-methylpyrazine | 14.0 | 1.4 | 2 | −2.0 | 4.3 | 2 |
| 4-methyl-2-propyl-1,3-dioxolane | 13.0 | 4.2 | 2 | −2.4 | 1.7 | 2 |
| 2-(2-methylpropyl)-1,3-thiazole | 12.0 | 2.8 | 2 | −11.0 | 2.8 | 2 |
| 2-methyl-3-methylsulfanylfuran | 12.0 | 12.7 | 2 | −7.5 | 3.5 | 2 |
| methoxymethylbenzene | 12.0 | 0.0 | 2 | −2.0 | 6.2 | 2 |
| 5-methyloxolan-2-one | 10.0 | 8.5 | 2 | −10.0 | 5.9 | 2 |
| oxolan-2-ylmethyl acetate | 10.0 | 1.4 | 2 | −4.5 | 2.2 | 2 |
| 2,3-dimethylbuta-1,3-diene | 10.0 | 2.8 | 2 | 4.4 | 3.4 | 2 |
| 6-methylquinoline | 9.5 | 10.0 | 3 | −4.5 | 7.8 | 2 |
| 4-hydroxy-2,3-dimethyl-2H-furan-5-one | 9.0 | 1.4 | 2 | −5.0 | 7.1 | 2 |
| 2-ethyl-1H-pyrrole | 8.5 | 4.9 | 2 | −7.5 | 3.5 | 2 |
| 1-(4,5-dihydro-1,3-thiazol-2-yl)ethanone | 8.0 | 0.0 | 2 | −9.0 | 11.3 | 2 |
| benzyl formate | 8.0 | 5.7 | 2 | −3.5 | 4.9 | 2 |
| 3-aminopropanoic acid | 8.0 | 0.0 | 2 | −2.5 | 9.2 | 2 |
| 3,5-dimethylpyridine | 7.5 | 9.2 | 2 | −8.0 | 5.7 | 2 |
| 2-oxobutanoic acid | 7.0 | 4.2 | 2 | −4.0 | 2.8 | 2 |
| 2-ethoxyoxolane | 6.5 | 20.5 | 2 | −2.5 | 6.4 | 2 |
| 3,7-dimethyloct-6-enoic acid | 6.0 | 9.9 | 2 | −3.5 | 12.0 | 2 |
| propan-2-yl benzoate | 6.0 | 1.4 | 2 | −2.0 | 1.5 | 2 |
| 3-(2-methylpropyl)pyridine | 5.5 | 0.7 | 2 | 1.0 | 12.7 | 2 |
| 2-phenylethyl 3-methylbutanoate | 4.5 | 0.7 | 2 | −0.5 | 13.4 | 2 |
| 2-(4-methyl-1,3-thiazol-5-yl)ethanol | 4.5 | 4.9 | 2 | 4.9 | 2.8 | 2 |
| 4-oxopentanoic acid | 4.5 | 2.1 | 2 | 6.3 | 3.2 | 2 |
| 3-methylpentanoic acid | 3.7 | 9.5 | 3 | 0.5 | 16.3 | 2 |
| 3-methylcyclopentane-1,2-dione | 3.5 | 6.4 | 2 | −2.1 | 2.9 | 2 |

TABLE 3-continued

List of tested odors

| IUPAC | Activation (spikes s$^{-1}$) | s.d. | N | % Inhibition | s.d | N |
|---|---|---|---|---|---|---|
| (2S)-2-amino-3-methylbutanoic acid | 3.5 | 6.4 | 2 | 2.2 | 9.0 | 2 |
| 1-pyridin-4-ylethanone | 3.5 | 7.8 | 2 | 3.5 | 13.4 | 2 |
| 1H-pyrazole | 3.5 | 3.5 | 2 | 4.9 | 2.8 | 2 |
| (2S)-pyrrolidine-2-carboxylic acid | 3.5 | 9.2 | 2 | 5.0 | 9.0 | 2 |
| (2E)-3,7-dimethylocta-2,6-dienoic acid | 3.0 | 2.8 | 2 | −5.7 | 4.0 | 2 |
| [(E)-3-phenylprop-2-enyl] formate | 3.0 | 1.4 | 2 | 5.5 | 20.5 | 2 |
| 2-phenylethyl (E)-2-methylbut-2-enoate | 2.5 | 0.7 | 2 | −4.3 | 4.0 | 2 |
| 1H-imidazole-5-carbaldehyde | 2.5 | 0.7 | 2 | −2.2 | 9.0 | 2 |
| 4-ethylbenzaldehyde | 2.5 | 6.4 | 2 | −0.7 | 7.1 | 2 |
| (Z)-hex-3-en-1-ol | 2.5 | 4.9 | 2 | −0.7 | 3.0 | 2 |
| 2-(trimethylazaniumyl)acetate | 2.5 | 7.8 | 2 | 3.7 | 14.9 | 2 |
| pyridazine | 2.5 | 3.5 | 2 | 10.3 | 10.6 | 2 |
| (E)-2-methylbut-2-enoic acid | 2.5 | 4.9 | 2 | 24.6 | 5.7 | 2 |
| 2,6-dimethylpiperidine | 2.5 | 4.9 | 2 | 27.1 | 10.1 | 2 |
| (Z)-non-6-en-1-ol | 2.0 | 0.0 | 2 | −5.7 | 2.0 | 2 |
| 4-hydroxy-4-methylpentan-2-one | 2.0 | 1.4 | 2 | −1.0 | 1.4 | 2 |
| cyclohexane-1,3-dione | 1.5 | 0.7 | 3 | −5.1 | 13.0 | 2 |
| 1-phenylbutan-1-one | 1.5 | 3.5 | 2 | −4.3 | 12.1 | 2 |
| 3,7-dimethyloct-6-en-1-ol | 1.5 | 6.4 | 2 | −3.6 | 11.1 | 2 |
| 1-(1H-pyrrol-2-yl)ethanone | 1.5 | 6.4 | 2 | −3.5 | 0.9 | 2 |
| 3,4-dimethylcyclopentane-1,2-dione | 1.5 | 9.2 | 2 | −3.5 | 0.9 | 2 |
| 6-hexyloxan-2-one | 1.5 | 0.7 | 2 | −2.9 | 20.2 | 2 |
| 4-methyl-2-(2-methylprop-1-enyl)oxane | 1.5 | 3.5 | 2 | 2.1 | 7.1 | 2 |
| 1,5-naphthyridine | 1.5 | 0.7 | 3 | 4.6 | 18.7 | 2 |
| 2-methyl-3-(2-methylpropyl)pyrazine | 1.0 | 2.0 | 2 | −2.9 | 14.1 | 2 |
| 3-hydroxybutan-2-one | 0.5 | 7.8 | 2 | −9.1 | 0.7 | 2 |
| 5-methylbenzene-1,3-diol | 0.5 | 3.5 | 2 | −7.7 | 2.7 | 2 |
| 4-phenylbutan-2-one | 0.5 | 2.1 | 2 | −0.7 | 9.1 | 2 |
| 3-methylbut-2-enoic acid | 0.5 | 2.1 | 2 | 27.4 | 5.8 | 2 |
| 2-oxopentanoic acid | 0.0 | 2.8 | 2 | −14.5 | 12.4 | 2 |
| pyrrolidin-2-one | 0.0 | 5.7 | 2 | −7.5 | 10.7 | 2 |
| piperidin-2-one | 0.0 | 5.7 | 2 | −6.3 | 3.2 | 2 |
| oct-1-en-3-yl butanoate | 0.0 | 1.4 | 2 | −4.0 | 2.9 | 2 |
| 2-(propan-2-ylsulfanylmethyl)furan | −0.5 | 0.7 | 2 | −4.3 | 8.1 | 2 |
| 4-hydroxy-4-methyloxan-2-one | −1.0 | 4.2 | 2 | −21.2 | 30.0 | 2 |
| 2-hydroxypropanoic acid | −1.0 | 1.4 | 2 | 9.7 | 5.0 | 2 |
| (E)-but-2-enoic acid | −1.5 | 10.6 | 2 | −4.8 | 6.8 | 2 |
| 2-aminopropanoic acid | −1.5 | 10.6 | 2 | −0.8 | 6.9 | 2 |
| (Z)-non-2-en-1-ol | −1.5 | 3.5 | 2 | 10.3 | 0.3 | 2 |
| 2-phenylethyl propanoate | −1.5 | 2.1 | 2 | 16.3 | 5.6 | 2 |
| benzyl 3-oxobutanoate | −1.5 | 0.7 | 2 | 21.1 | 14.9 | 2 |
| 2-oxopropanal | −2.0 | 2.8 | 2 | −33.6 | 47.5 | 2 |
| 2-amino-3-methylpentanoic acid | −2.5 | 9.2 | 2 | −16.2 | 9.4 | 2 |
| [(2E)-3,7-dimethylocta-2,6-dienyl] formate | −2.5 | 0.7 | 2 | 12.0 | 4.5 | 2 |
| 2-aminobutanoic acid | −3.0 | 1.4 | 2 | −10.3 | 10.6 | 2 |
| heptan-4-ol | −3.0 | 2.8 | 2 | −3.1 | 7.1 | 2 |
| 3-phenylpropan-1-ol | −3.0 | 7.1 | 2 | 14.5 | 8.1 | 2 |
| 5-phenylpentan-1-ol | −3.0 | 1.4 | 2 | 16.0 | 7.8 | 2 |
| piperazin-2-one | −3.2 | 10.9 | 2 | 16.4 | 10.8 | 2 |
| 1-phenylpropan-1-ol | −3.5 | 17.7 | 2 | 5.7 | 4.4 | 2 |
| 2-methylpropyl (Z)-but-2-enoate | −5.0 | 7.1 | 2 | −3.0 | 0.1 | 2 |
| (E)-pent-2-enal | −5.0 | 17.0 | 2 | 11.4 | 3.7 | 2 |
| 2-phenylethyl butanoate | −5.5 | 0.7 | 2 | 0.7 | 18.9 | 2 |
| 5,6,7,8-tetrahydroquinoxaline | −5.5 | 12.0 | 2 | 9.9 | 3.3 | 2 |
| 2-pentylpyridine | −6.5 | 7.8 | 2 | 9.8 | 4.0 | 2 |
| 2-ethyl-3-methylpyrazine | −7.5 | 4.9 | 2 | 6.7 | 8.1 | 2 |
| 2-(ethoxymethyl)pyrazine | −8.0 | 11.3 | 2 | 3.0 | 0.3 | 2 |

TABLE 3-continued

List of tested odors

| IUPAC | Activation (spikes s$^{-1}$) | s.d. | N | % Inhibition | s.d | N |
|---|---|---|---|---|---|---|
| 4-propylphenol | −9.0 | 15.6 | 2 | −1.0 | 1.4 | 2 |
| 2-butan-2-yl-3-methoxypyrazine | −10.5 | 21.9 | 2 | 0.5 | 0.7 | 2 |
| 2,3-diethylpyrazine | −15.5 | 9.2 | 2 | 1.3 | 0.5 | 2 |
| 2-ethyl-3-methoxypyrazine | −17.5 | 20.5 | 2 | 2.7 | 5.2 | 2 |
| 2-methoxy-3-methylpyrazine | −27.5 | 23.3 | 2 | 12.6 | 8.4 | 2 |
| methyl acetate | −50.5 | 3.5 | 2 | −4.5 | 3.1 | 2 |
| ethyl 2-oxopropanoate (ethyl pyruvate) | −63.0 | 17.3 | 3 | 92.8 | 2.7 | 6 |
| methyl 2-oxopropanoate (methyl pyruvate) |  |  |  | 100 | 0 | 6 |

*n/d refers to "no data"

Several of these were also pleasant-smelling to humans. Odorants in this initial electrophysiology screen were presented in a manner so that cpA's background firing rate was raised during stimulation by ~50 spikes s$^{-1}$, thus also revealing a number of potential inhibitors (FIG. 3b).

Figure 3C:
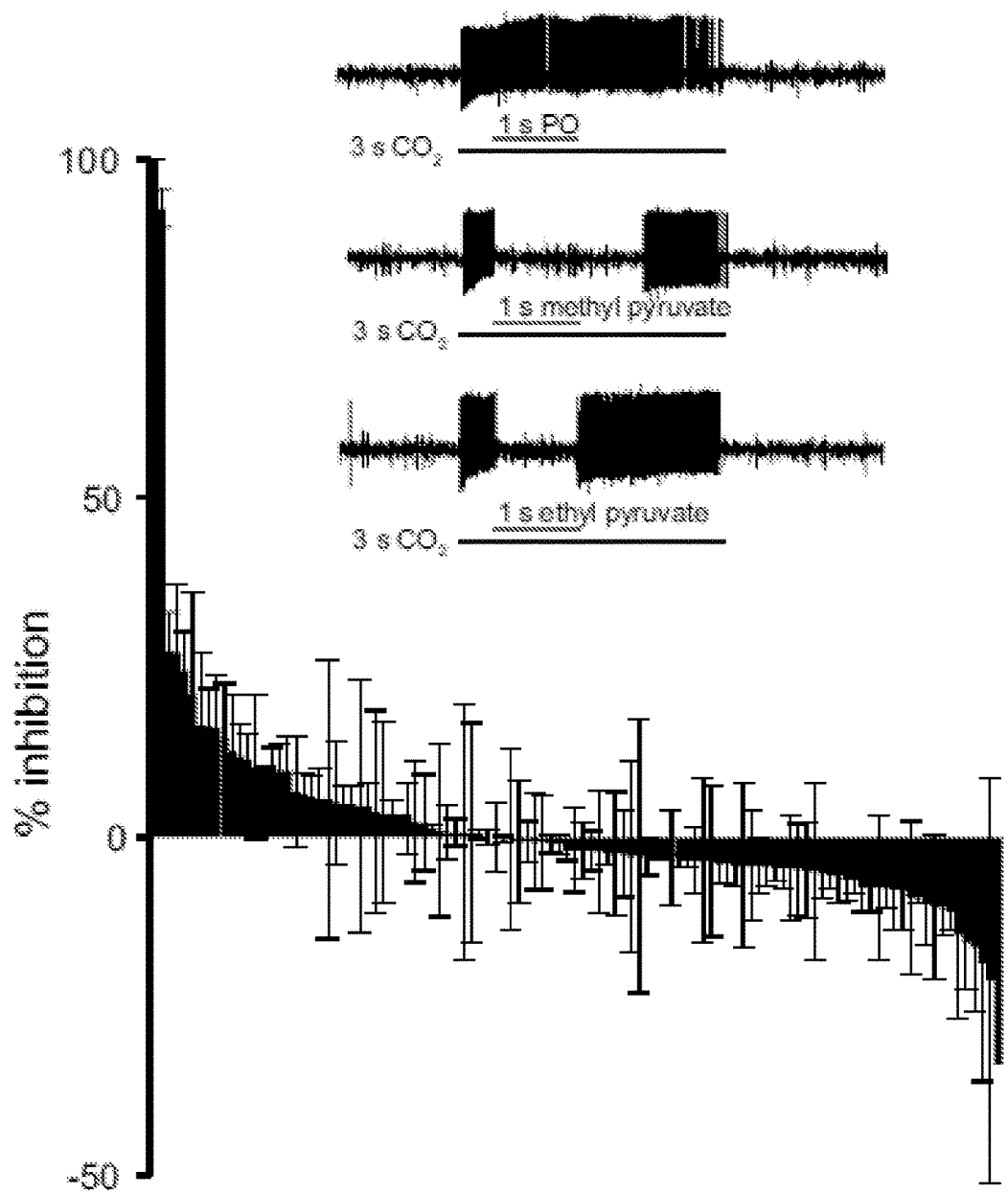
FIG. 3c depicts representative traces and mean percent inhibition of the A. aegypti cpA neuron's response to 0.15% $CO_2$ by a panel of 107 odorants presented as a 1-s stimulus ($10^{-2}$) in the middle of a 3-s $CO_2$ stimulus, where n=2, except for ethyl and methyl pyruvate, n=6. Percent inhibition was calculated by comparing mean odorant overlay responses to mean solvent overlay responses, and error bars are s.d.
Figures 11A, 11B:
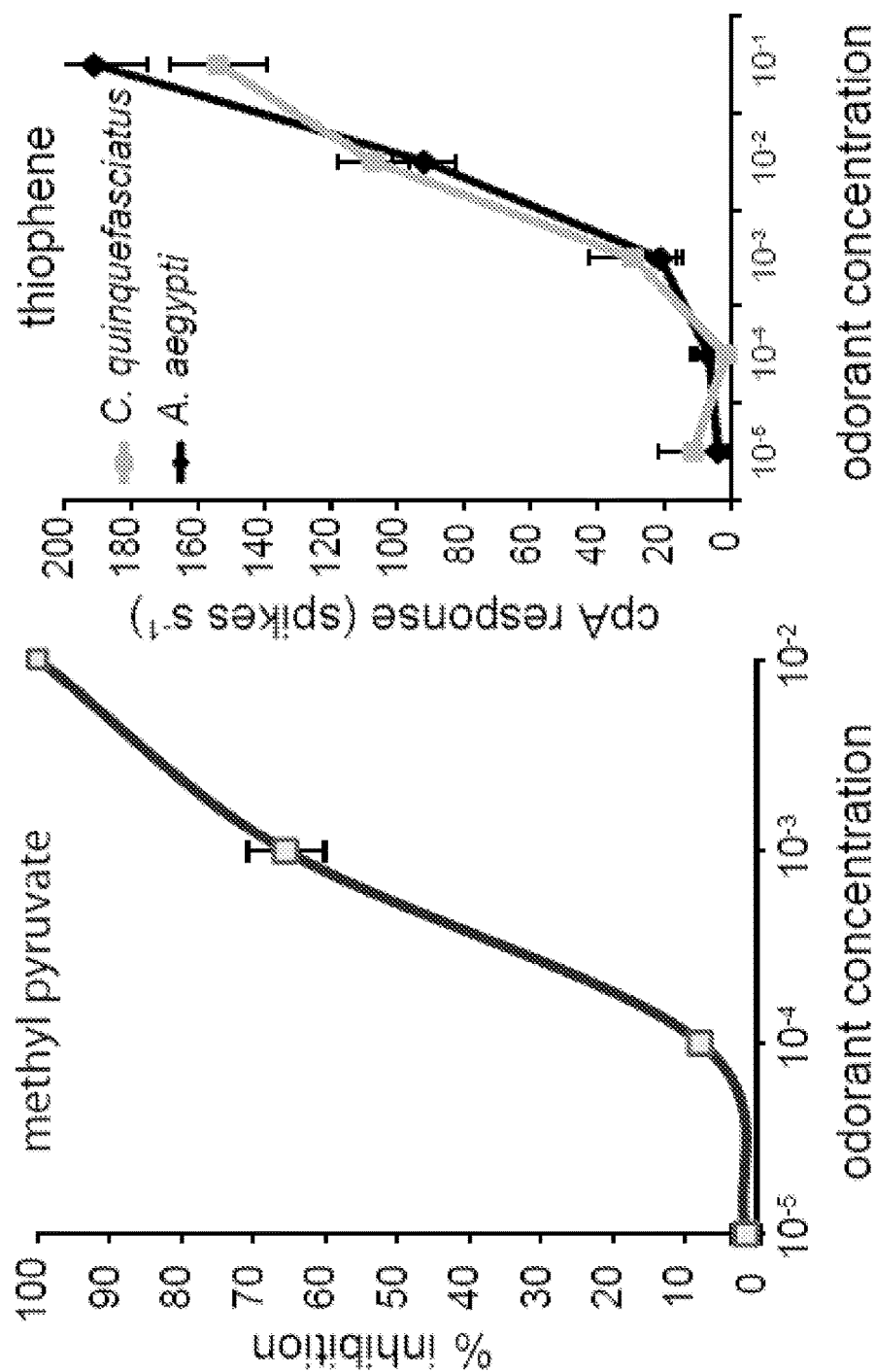
FIG. 11a illustrates the mean percent inhibition of *A. aegypti* cpA response to 0.15% $CO_2$ overlaid with different concentrations of methyl pyruvate (n=6).
FIG. 11b illustrates the mean responses of the cpA neuron to different concentrations of thiophene for *C. quinquefasciatus* and *A. aegypti* (n=4).

Along with the 15 odors that reduced the background firing rate, all odorants that did not activate cpA with >40 spikes s$^{-1}$ were retested in an additional electrophysiology screen for ability to inhibit response to an overlaid 0.15% $CO_2$ stimulus (FIG. 3c). Several compounds inhibited cpA to some degree; ethyl pyruvate strongly inhibited cpA activity (FIG. 3c and Table 3 above). A structurally related odorant, methyl pyruvate, also strongly inhibited cpA even at low concentrations (FIG. 3c, Table 3 above, FIG. 11a). Comparable inhibition was observed at ~10 times lower concentrations than for previously reported inhibitors such as 1-hexanol.

Figure 3D:
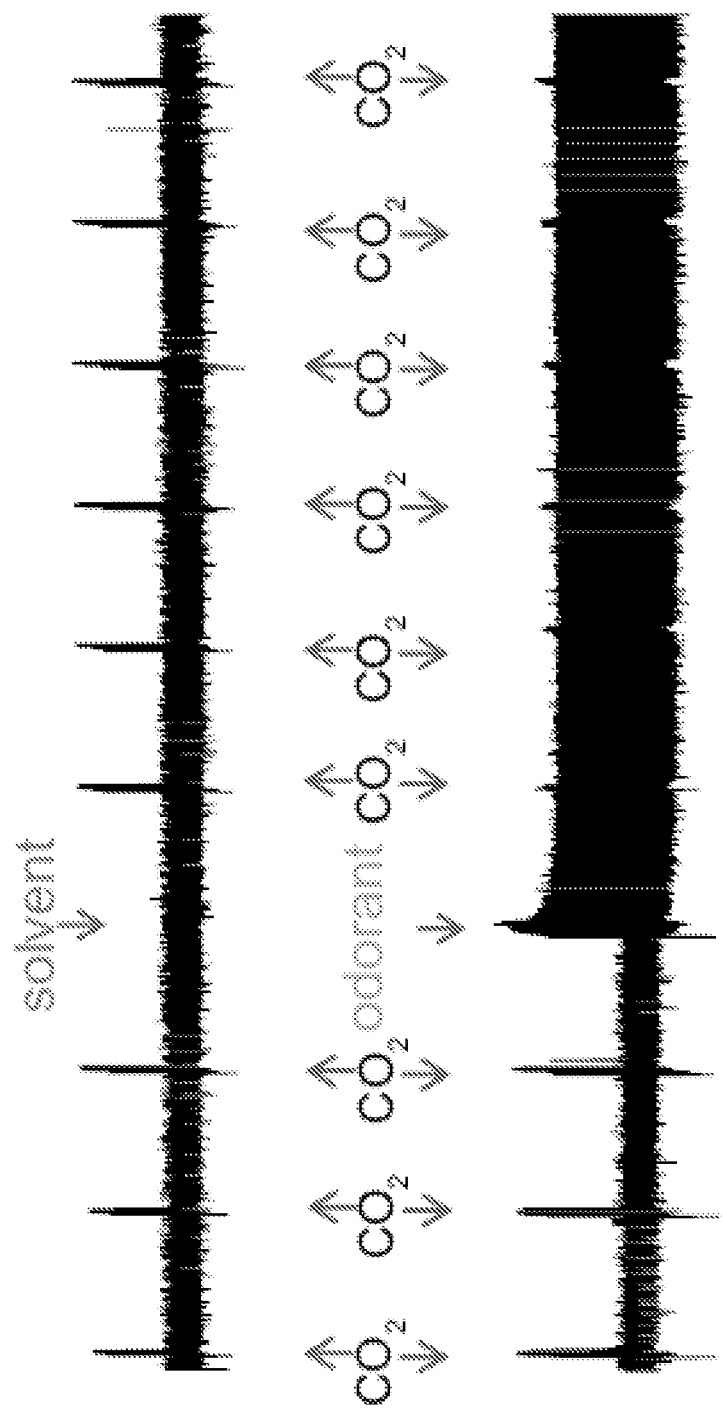
FIG. 3d depicts representative traces from the A. aegypti cp sensillum to 1-s pulses of 0.15% $CO_2$ prior to and following a 3-s exposure to either solvent (paraffin oil) or (E)-2-methylbut-2-enal ($10^{-1}$).
Figure 3E:
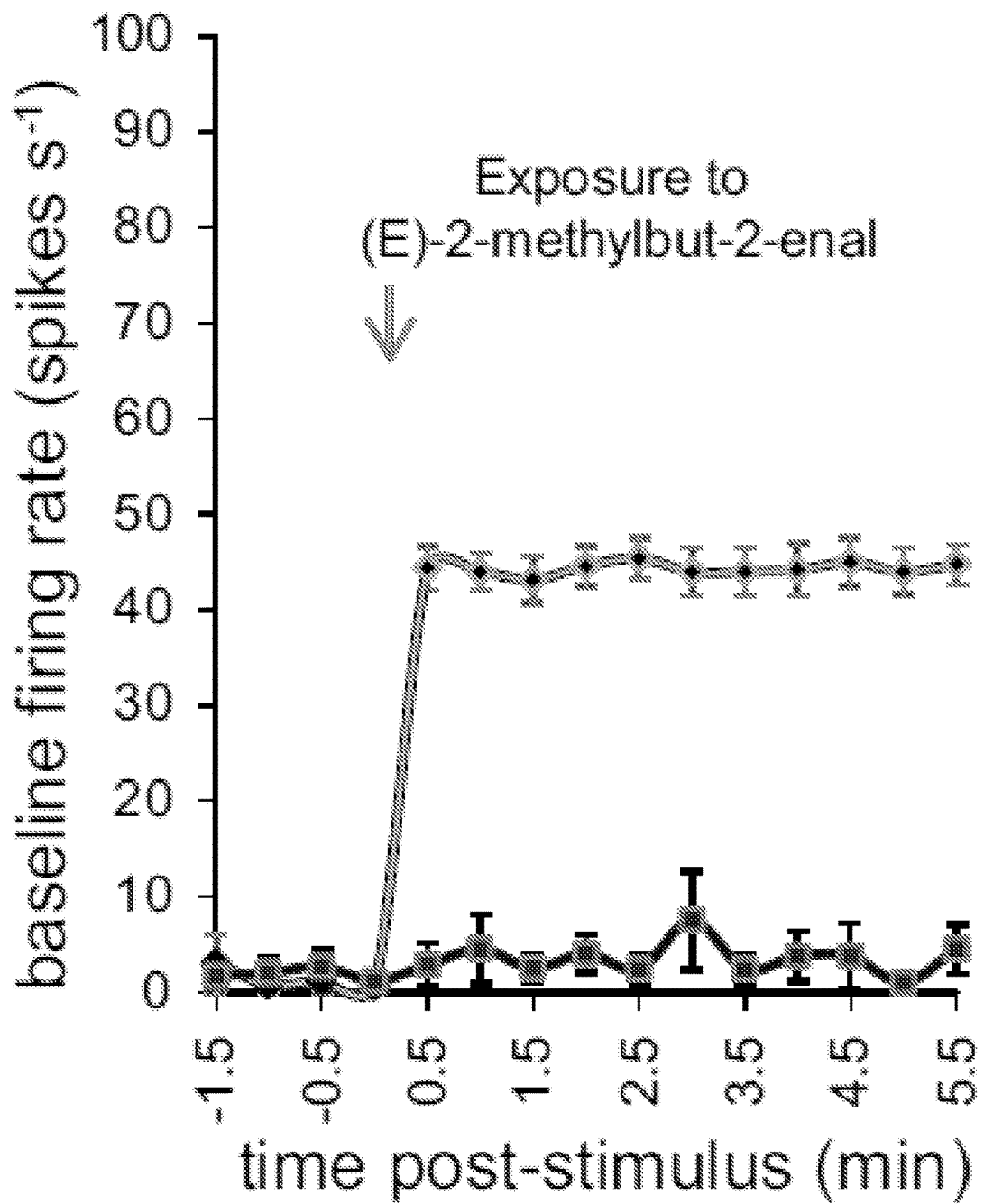
FIG. 3e is a graph illustrating the cpA baseline activity in the 1 s prior to each stimulus is elevated following exposure to odorant, where error bars are s.e.m.
Figure 3F:
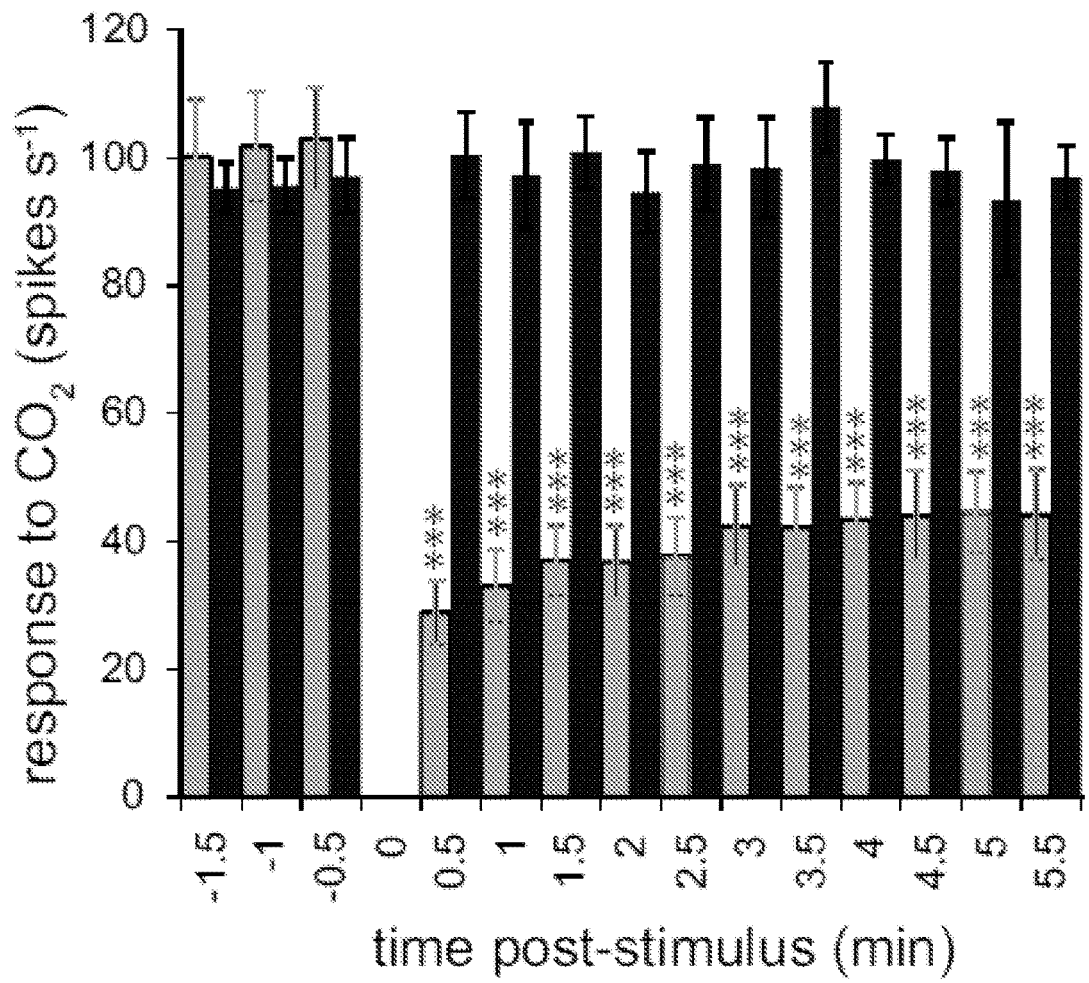
FIG. 3f is a bar graph illustrating the mean responses of the cpA neuron to 1-s pulses of 0.15% $CO_2$, calculated by subtracting the 1 s of the baseline activity prior to each stimulus, where n=5-6 individuals, analysed by t-test, ***p<0.001, and error bars are s.e.m.

Additionally, longer-term recordings with newly-discovered activators revealed that a 3-s exposure to (E)-2-methylbut-2-enal results in sustained firing of cpA at ~45 spikes s$^{-1}$ for at least 5.5 min (FIG. 3d,e). Responses to 1-s pulses of 0.15% $CO_2$ during this period are significantly reduced relative to controls (FIG. 3f), suggesting that this odor, which smells better (green fruit) than butanedione (rancid butter), may also disrupt navigation towards a $CO_2$ source.

Example 5

A cpA Inhibitor Reduces Attraction of Mosquitoes to Skin

Figure 4A:
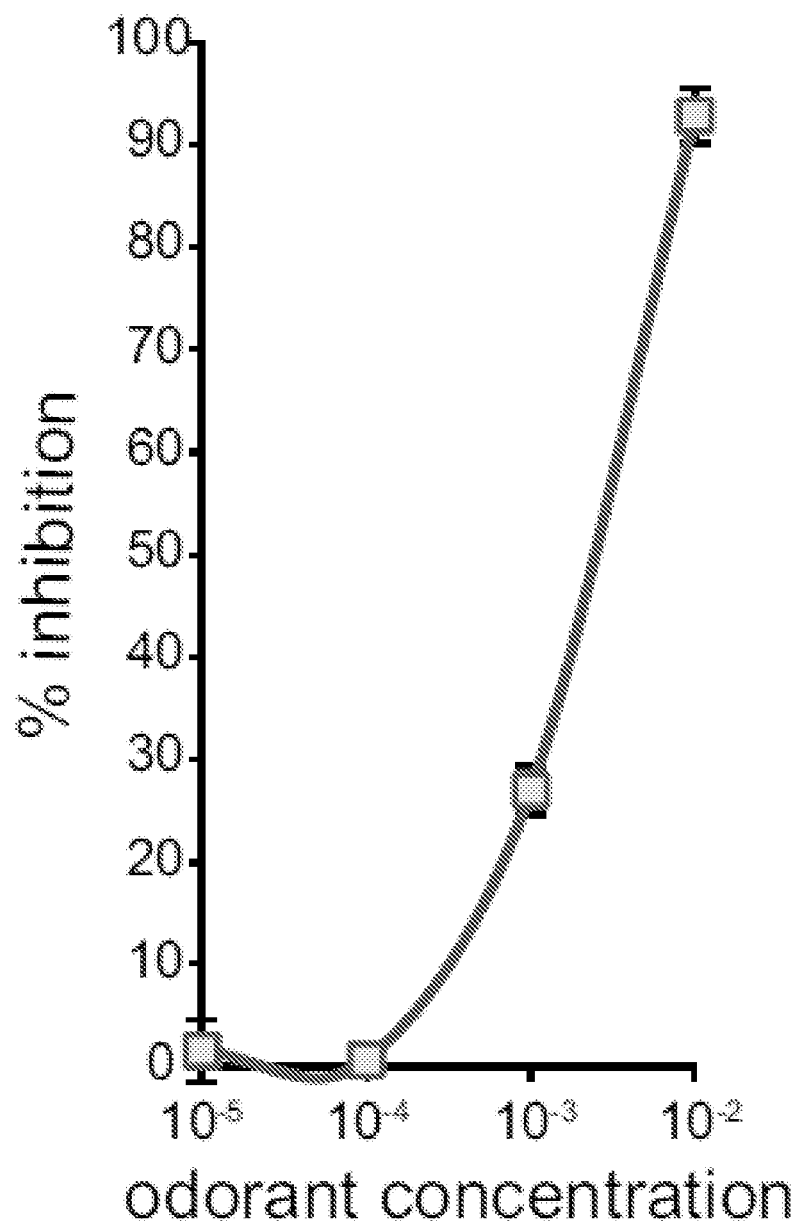
FIG. 4a is a graph illustrating the dose response of inhibition of A. aegypti cpA neuron when a 1-s stimulus of ethyl pyruvate is overlaid on a 3-s stimulus of 0.15% $CO_2$, where n=6 for each concentration.
Figure 4B:
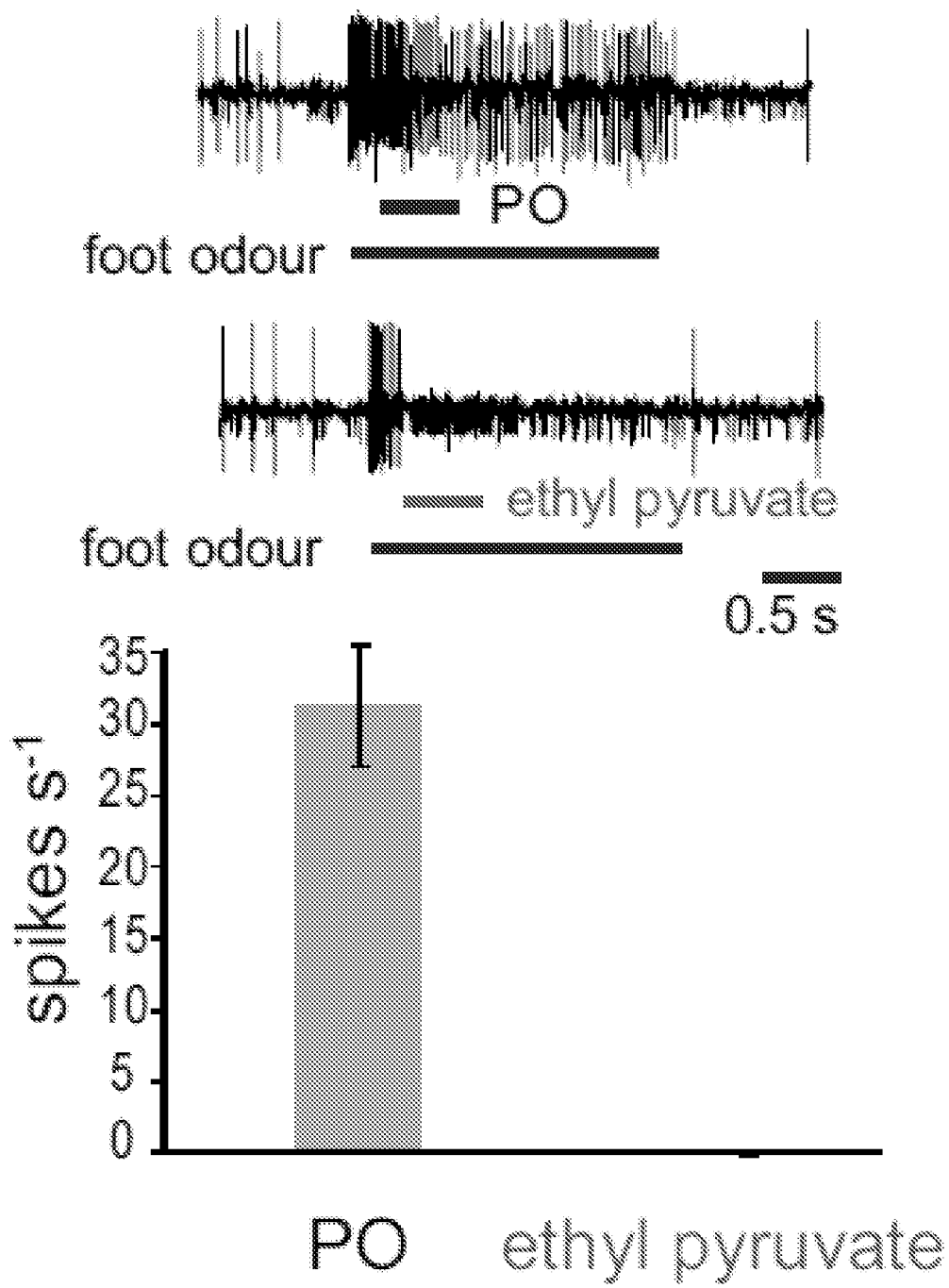
FIG. 4b depicts representative trace and mean response when a 1-s stimulus of ethyl pyruvate ($10^{-2}$) is overlaid on a 2-s stimulus of foot odor (mixed beads from Person 1 and Person 2), where n=6.

This Example demonstrates that an inhibitory odorant may block attraction of mosquitoes to skin.
Materials and Methods
Hand-in-Cage:
Forty 4-10-day-old female *A. aegypti* were starved 24 hrs and released in a 30×30 cm cage with a glass top, and trials commenced between 1400 and 1700 hrs. A human hand wearing a nitrile glove (Sol-vex) with a 7×6 cm window covered by two layers of fine polyester mesh (BioQuip, mesh size 26×22 holes per in$^2$) held in place by magnetic spacers, was inserted into the cage. The lower mesh was 1.5 mm above, and upper mesh was 6 mm above the hand. While skin emanations passed freely through the mesh window, the hand was protected from contact with mosquitoes and treated mesh. The outside mesh was treated with ethyl pyruvate (500 μl, 10% in acetone) or solvent. After letting solvent evaporate the glove was assembled. Experimenter inserted a hand in a control glove into the cage for 5 min, then the same hand was placed inside a test glove and reinserted into the same cage for an additional 5 min. Trials were video recorded and mosquitoes on the mesh were counted every 15 s.
Results
The cpA inhibitor ethyl pyruvate was selected for testing since it is listed as a GRAS compound, is approved as a flavor agent in food, and has a pleasant smell (fruity, sweet, rum, caramel) (Table 3 above). Ethyl pyruvate completely eliminates response of the cpA neuron to human foot odor when they are presented together (FIG. 4b).

Figure 4C:
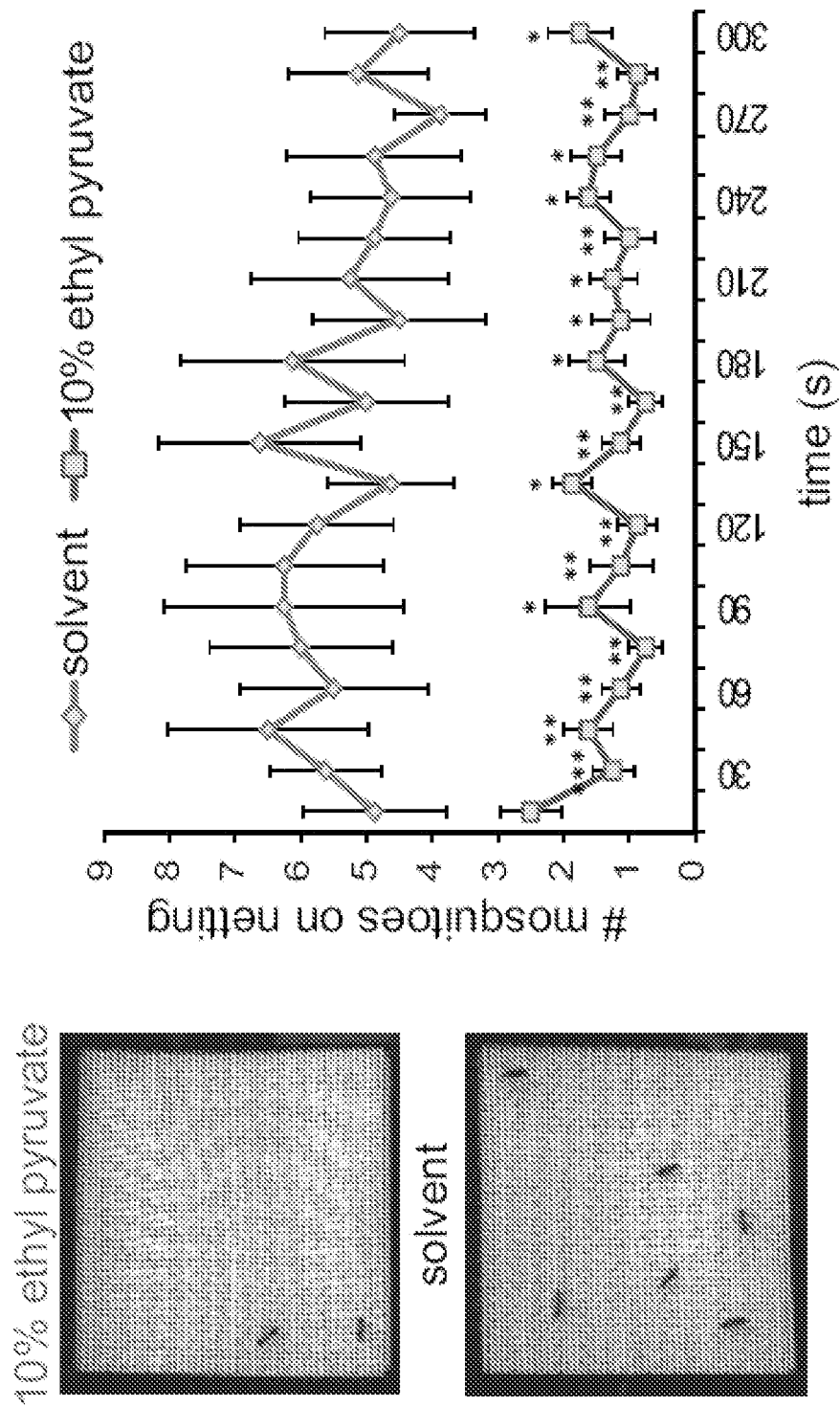
FIG. 4c depicts representative images (left) of hand-in-cage assay mesh window and a graph (right) illustrating the mean number of mosquitoes on the netting at the indicated time points for ethyl pyruvate-treated or solvent-treated netting. n=8 each.

An arm-in-cage repellency assay was used in this Example using gloves with chemical treated mesh-covered windows to quantify attraction of *A. aegypti* mosquitoes to the human hand without exposing the hand to mosquito bites or skin to contact with test chemicals. Ethyl pyruvate substantially reduced the number of times mosquitoes landed on the mesh over a human hand (FIG. 4c). The simplest interpretation of these results when considered along with the previous wind tunnel experiments is that inhibition of the cpA neuron reduces attraction by masking detection of skin odor.

Example 6

A cpA Activator Lures Mosquitoes to a Trap as Effectively as $CO_2$

This Example demonstrates whether an odorant that can mimic $CO_2$-mediated activation of the cpA neuron can substitute for $CO_2$ as an effective lure.
Materials and Methods
Semi-field trapping: Two modified greenhouses at the Agricultural Experiment Station at the University of California, Riverside, were used as described previously[2], with modifications. Fifty laboratory-reared, mated, non-blood fed female *C. quinquefasciatus* aged 8-14 days and starved for 24 hrs were released each evening around 5 pm and traps collected at ~7 am. Counter flow geometry traps baited with $CO_2$ (250 ml min$^{-1}$, ~670 mmol/hr) odorant were used as described[2], with modifications. Odorant solutions in water were dispensed from 20 cm long gauze wicks protruding from uncapped 50 ml tubes beneath the trap outflow. For each trial, one baited trap and one control trap (water-filled) were placed in each of two greenhouses (FIG. 4g). For two-choice $CO_2$ trials, water was placed under both traps. For two-choice ethyl pyruvate trials, both traps expelled $CO_2$, and one trap also released ethyl pyruvate from an open 2.8×7 cm glass vial. Since ethyl pyruvate has very low volatility pure compound was used to generate ~1.7 mmol/hr. An empty vial was placed under control traps. Treatment position and trap were alternated across trials. Volume of solution lost from tubes containing 5%, 10%, or 20% cyclopentanone were measured after each trial and the average loss of molecules calculated respectively for 3 concentrations as (±s.d.) of 0.7 (±0.1), 1.7 (±0.4), and 3.8 (±0.3) mmol/hr, respectively. Preference index=(# mosquitoes in odor-baited trap−# mosquitoes in control trap)/(total # mosquitoes caught in both traps).

Results

Figures 4D, 4E:
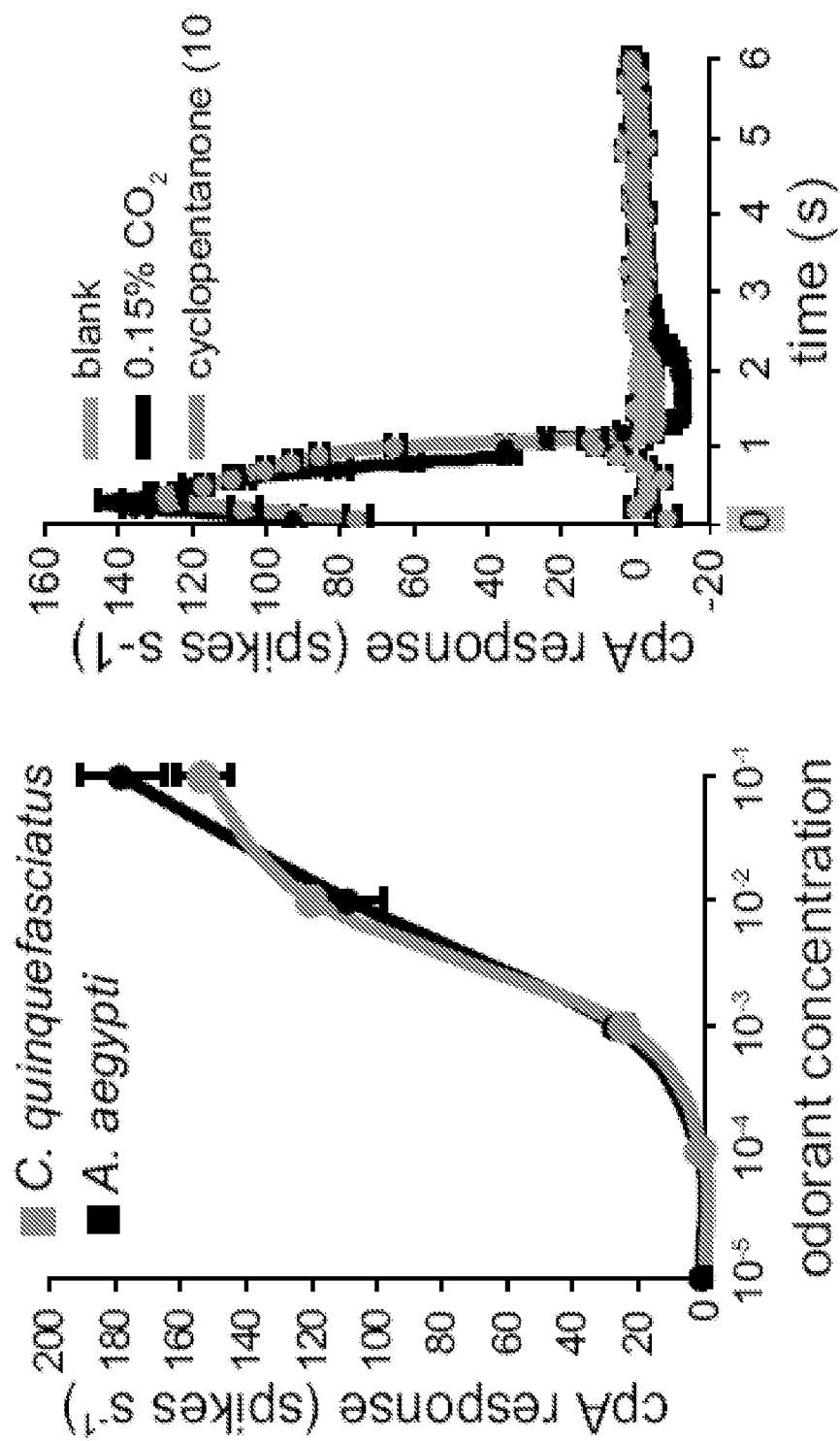
FIG. 4d is a graph illustrating the dose responses of the cpA neuron to cyclopentanone in A. aegypti and C. quinquefasciatus, where n=5-6.
FIG. 4e is a graph illustrating the mean responses in 100 ms bins to pulses of cyclopentanone ($10^{-2}$), $CO_2$, or blank odor cartridges. n=4 replicates of 6 repeated pulses of each odorant.
Figure 4F:
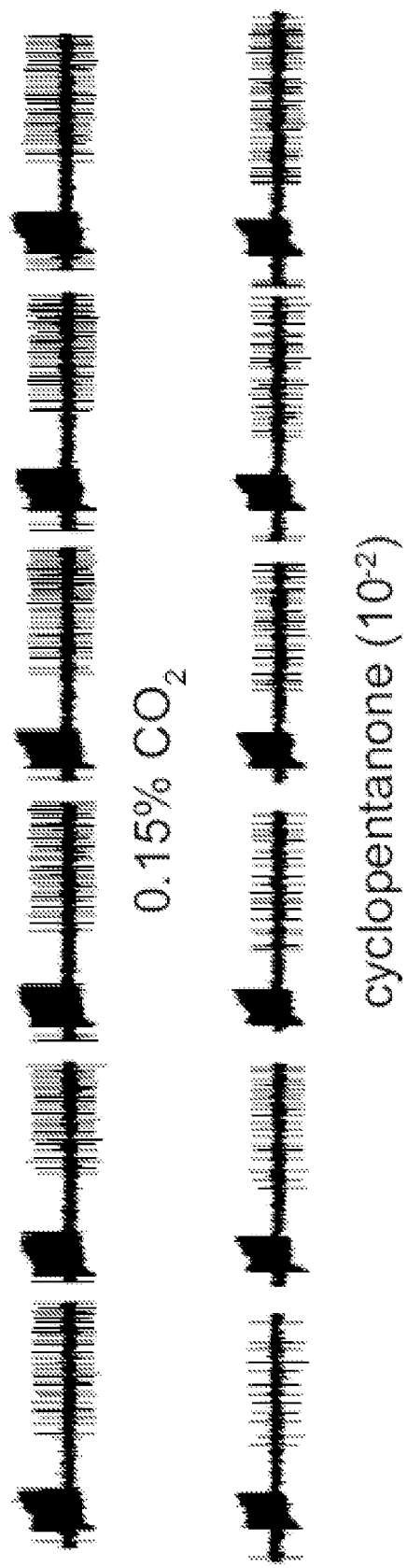
FIG. 4f depicts representative traces of repeated 1-s stimuli of cyclopentanone ($10^{-2}$) and 0.15% $CO_2$.
Figure 4G:
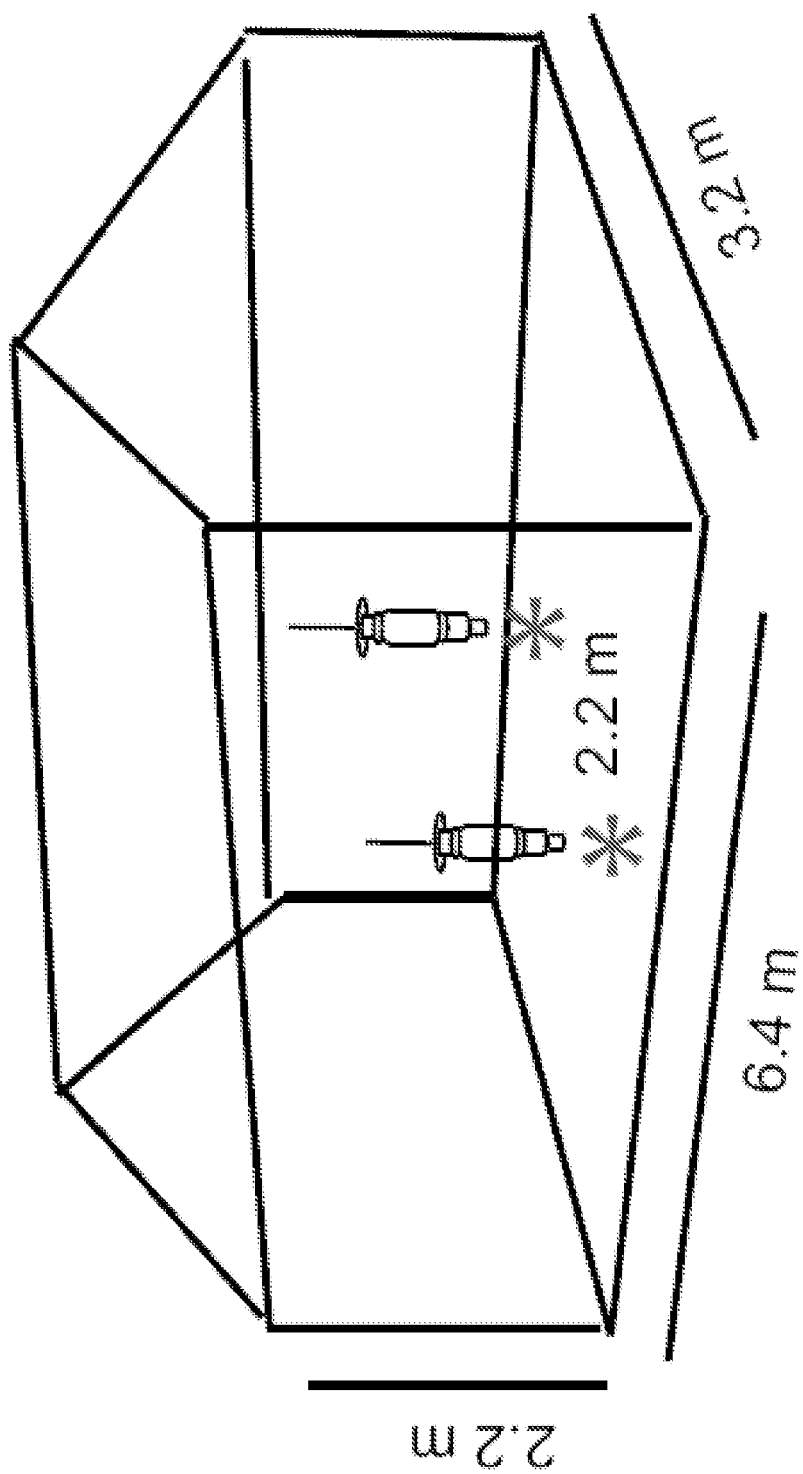
FIG. 4g is a schematic of two-choice greenhouse experiments with two counterflow geometry traps, in which mosquitoes were trapped overnight in odorant-baited and solvent (water)-baited traps.
Figure 11C:
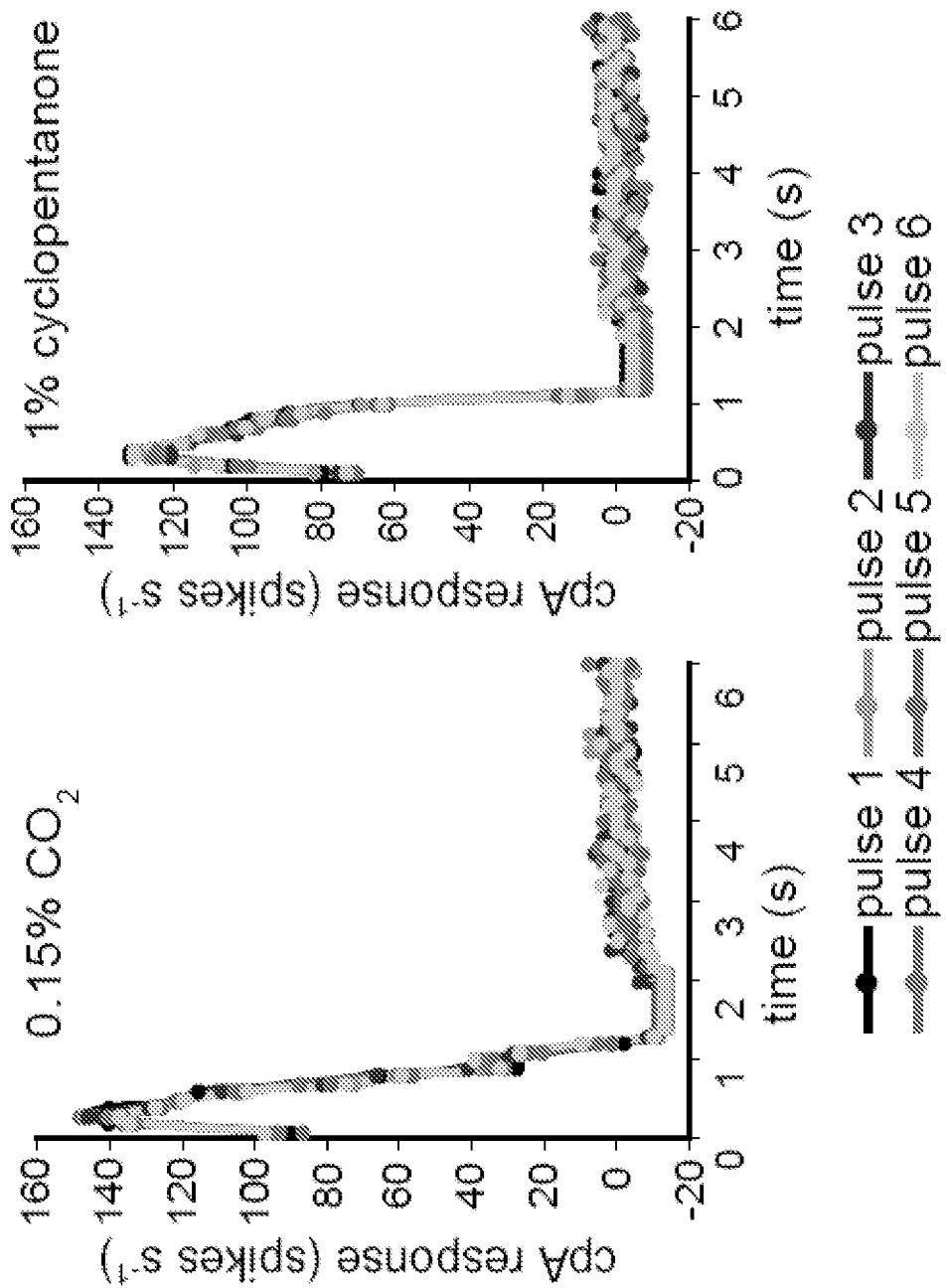
FIG. 11c illustrates that the temporal response profiles elicited by repeated exposures to cyclopentanone are similar to those elicited by $CO_2$. Individuals were exposed to 6 repeated 1-s pulses of either 0.15% $CO_2$ or cyclopentanone (10-2), spaced 20 s apart. Shown are the mean responses (across 4 animals per treatment) for each sequential pulse. Activity was calculated in 100 ms bins for a total of 6 s following the onset of the stimulus. Values were adjusted by subtracting baseline activity measured 5-6 s after each pulse.

Dose response curves were generated for two strong activators in both *A. aegypti* and *C. quinquefasciatus* (FIG. 4d, FIG. 11b). Cyclopentanone is a strong activator in both these species, is approved as a flavor and fragrance agent, is listed as a GRAS substance, and also has a pleasant minty smell (Table 3 above). Cyclopentanone mimics $CO_2$'s temporal activation profile to repeated 1-s stimuli (FIG. 4e,f), and the cpA neuron tracks changes in levels of both compounds with similar temporal acuity (FIG. 4e, FIG. 11c), suggesting that mosquitoes will be able to efficiently navigate along plumes of this odorant. Taken together, the strong and conserved cpA response, promising safety and fragrance profile, and ability to mimic $CO_2$ activation made cyclopentanone an excellent candidate for behavioural testing.

Figures 4H, 4I:
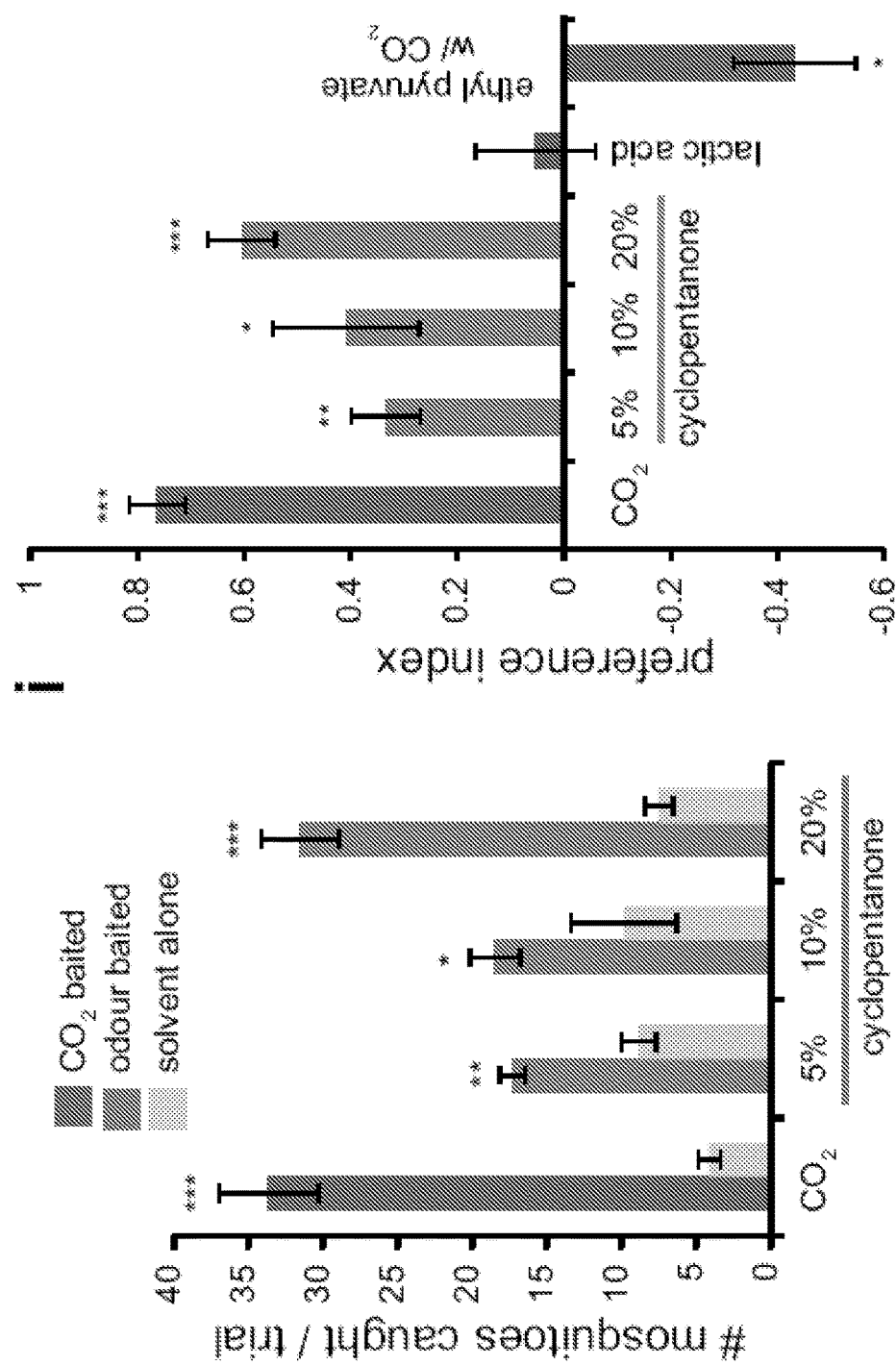
FIG. 4h is a graph illustrating the mean number of mosquitoes/trial captured in baited and control traps. n=9 trials with $CO_2$, n=6 with each concentration of cyclopentanone.
FIG. 4i is a graph illustrating the preference index for $CO_2$ and cyclopentanone trials (from FIG. 4h), and for similar two-choice assays between lactic acid and solvent (n=6) or between $CO_2$ and $CO_2$ with ethyl pyruvate. n=5, where error bars are s.e.m, t-test, *p<0.05, p<0.01, *p<0.001.

The efficacy of cyclopentanone as a lure was tested using traps in controlled semi-field experiments with *C. quinquefasciatus*, a mosquito present in Southern California, where the experiments took place. 50 female mosquitoes were released overnight in a modified greenhouse that contained two counter-flow geometry mosquito traps (FIG. 4g). One trap was baited with an evaporative lure of cyclopentanone diluted in water, and the second trap was baited with water alone. Mosquitoes preferred cyclopentanone over solvent-baited traps in a dose-dependent manner (FIGS. 4h and 4i). Remarkably, capture numbers for traps baited with cyclopentanone were comparable to those recorded for traps baited with $CO_2$ in similar trials performed in parallel (FIGS. 4h and 4i). The number of molecules of cyclopentanone released, calculated from the amount that evaporated during the assay, was ~176-fold less than the number of molecules of $CO_2$ released to produce a comparable catch rate (Online Methods). To our knowledge, no other odorant-based lure has been able to trap mosquitoes effectively in the absence of $CO_2$, let alone at rates comparable with $CO_2$. For example, traps baited with 10% lactic acid, one of the few known weak attractants of mosquitoes in laboratory assays, did not catch significantly more mosquitoes than control traps (FIG. 4i).

The same assay was also used to test whether the inhibitor ethyl pyruvate could mask detection of a $CO_2$ source. A $CO_2$-baited trap that was also dispensing ethyl pyruvate caught significantly fewer mosquitoes than a control $CO_2$-baited trap (FIG. 4i).

Example 7

Odor Space Detected by the cpA Neuron

This Example explores the nature of the odorant chemical space detected by the cpA neuron.

Materials and Methods

Optimized Descriptor Sets:

A single energy-minimized 3D structure was generated for each chemical using Omega2 software (OpenEye). 3,224 molecular descriptors were calculated from 3D structures with the Dragon software package (Talete), values were normalized across compounds, and descriptors that did not show variation were removed. Optimized descriptor subsets were iteratively identified using a Sequential Forward Selection (SFS) method. The SFS approach selected descriptors that increased the correlation between ligand activity and chemical similarity, calculated using Euclidean distance from descriptor values. Ligands that evoked >30 spikes $s^{-1}$ were classified as activators, and those that reduced baseline firing rate by >5 spikes $s^{-1}$ were classified as inhibitors. This process was run independently for each of 3 training sets (aromatic/cyclic ligands, straight-chain ligands, and a combined set), resulting in 3 unique descriptor subsets. These three activity-optimized descriptor subsets were combined into a single descriptor set with 64 descriptors representing molecular features that predict $CO_2$ receptor activity. Optimized descriptor values were used to cluster active ligands and as features for principle component analysis (PCA). Computational analysis was performed in R.

Ligand Prediction:

Each activity-optimized descriptor set was applied to rank a library of >440,000 compounds based on the Euclidean distance of each chemical from a previously known ligand. The compound library comprised 3,197 volatile compounds from known origins including plants[51], insects[52], humans[20-23,53-55], a fragrance collection[56] including fruit and floral volatiles, and additional compounds from the eMolecules catalogue selected for having similar physical properties to known odorants (<350 MW and atoms C, O, N, H, I, Cl, S, F).

Ligand Prediction Using SVM:

A new receptor-optimized descriptor set (Table 4) was calculated based on ligand activity data for *A. aegypti* alone (this study). This descriptor set was utilized to train a Support Vector Machine (SVM) using regression and a radial basis function kernel available in the R package e1071, which integrates libsvm. Optimal gamma and cost values were determined using the Tune.SVM function. The resulting trained SVM was then applied to predict activity for compounds from the >440,000 compounds.

Computational Validation:

Twenty independent 5-fold cross-validations of the computational approach was performed. For each validation, the dataset of known ligands was randomly divided into 5 equal sized partitions and 4 of the partitions were applied to train the SVM and the remaining partition, which was not used for training, was used to test predictive ability. This process was repeated 5 times for each independent run with each partition excluded and used to test predictive ability exactly once. The overall predictive ability was calculated as a single receiver operating characteristic (ROC) curve for all 20 independent validations.

Selection of Compounds for Screening:

Predicted ligands were screened for organoleptic odor profile using a flavor and fragrance database. Compounds that did not have foul smells and were categorized as flavor, fragrance or cosmetic agents were considered for purchase. A few additional compounds were also selected after cross-checking MSDSs and other literature to leave out carcinogens, neurotoxins, etc.

Results

Figure 5A:
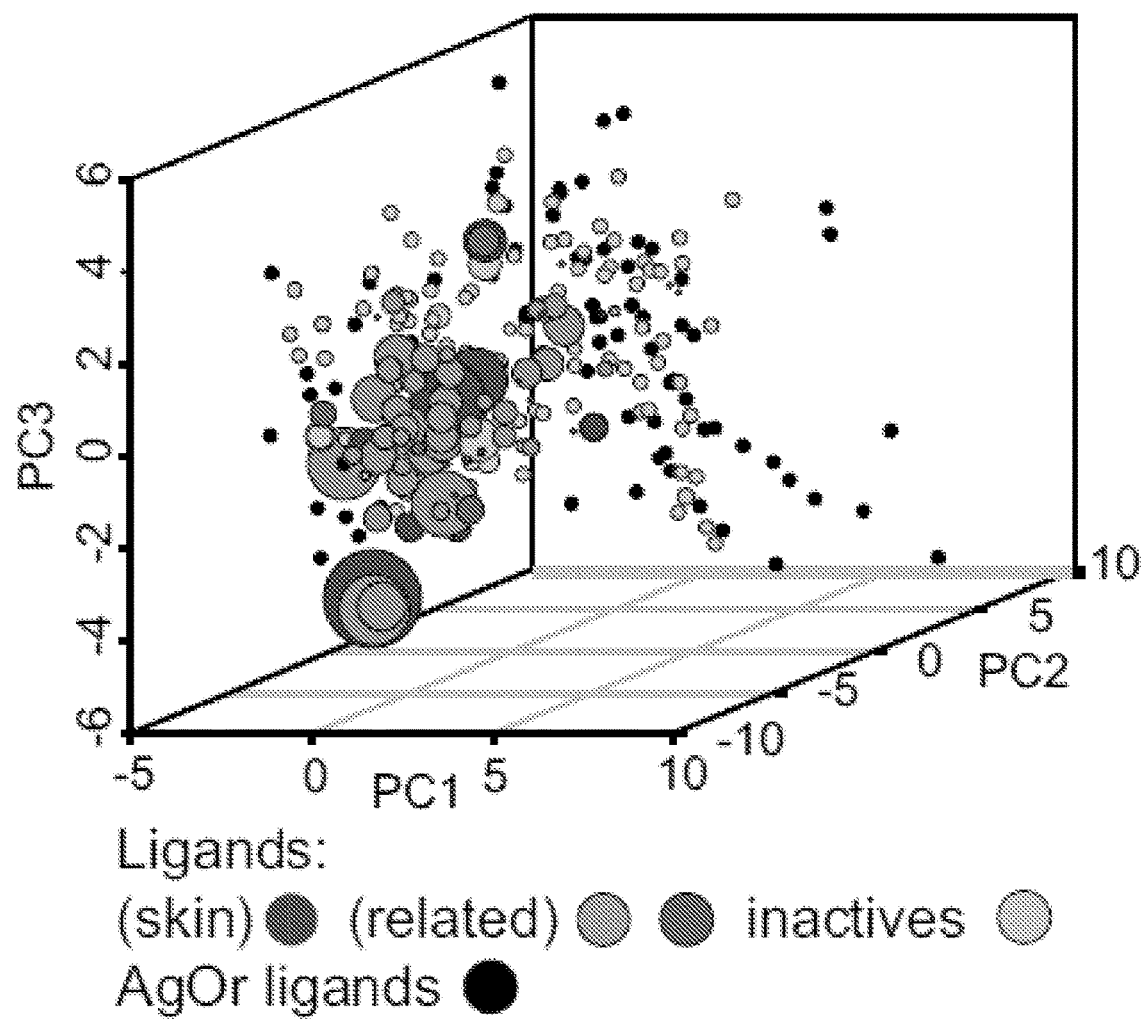
FIG. 5a is a graph illustrating the principle component analysis (PCA) of odorants calculated from 64 optimized molecular descriptor values, in which circle size corresponds to cpA activity evoked by each odorant, and dark green=human skin odorants, light green=predicted activator, red=predicted inhibitor, grey=predicted odorants that are inactive, black=odorants that activate A. gambiae olfactory receptors (AgOrs).

The action potentials evoked in the cp sensillum by $CO_2$, whole foot odor, and odorants from multiple structural classes were first analyzed to confirm that cpA's action potentials can be distinguished unambiguously in each case by their characteristically large relative spike amplitude (FIG. 8). To investigate structural similarities of cpA ligands, their relationships in chemical space were analyzed. The 3 sets of optimized descriptors used to predict cpA ligands (FIG. 3a) include a total of 64 molecular descriptors representing structural features that predict cpA activity, so were used to map the position of each tested skin odorant in 64-dimensional space. Principle component analysis (PCA) makes it possible to visualize the optimized descriptor-based relationships between each of the tested skin odorants in a 3-dimensional chemical space (dark green dots, FIG. 5a). Most active skin odorants were observed to be present in a relatively small region of this chemical space. Ligands that were predicted in silico and confirmed as activators by electrophysiology (light green dots, FIG. 5a) populate regions that overlap with the active skin odorants. Inhibitory odorants also overlap the same regions, suggesting that their effect may be mediated via similar binding sites on the $CO_2$ receptor (red dots, FIG. 5a). Odorants that did not show activity are mostly found in a non-overlapping region (grey dots, FIG. 5a).

Figure 5B:
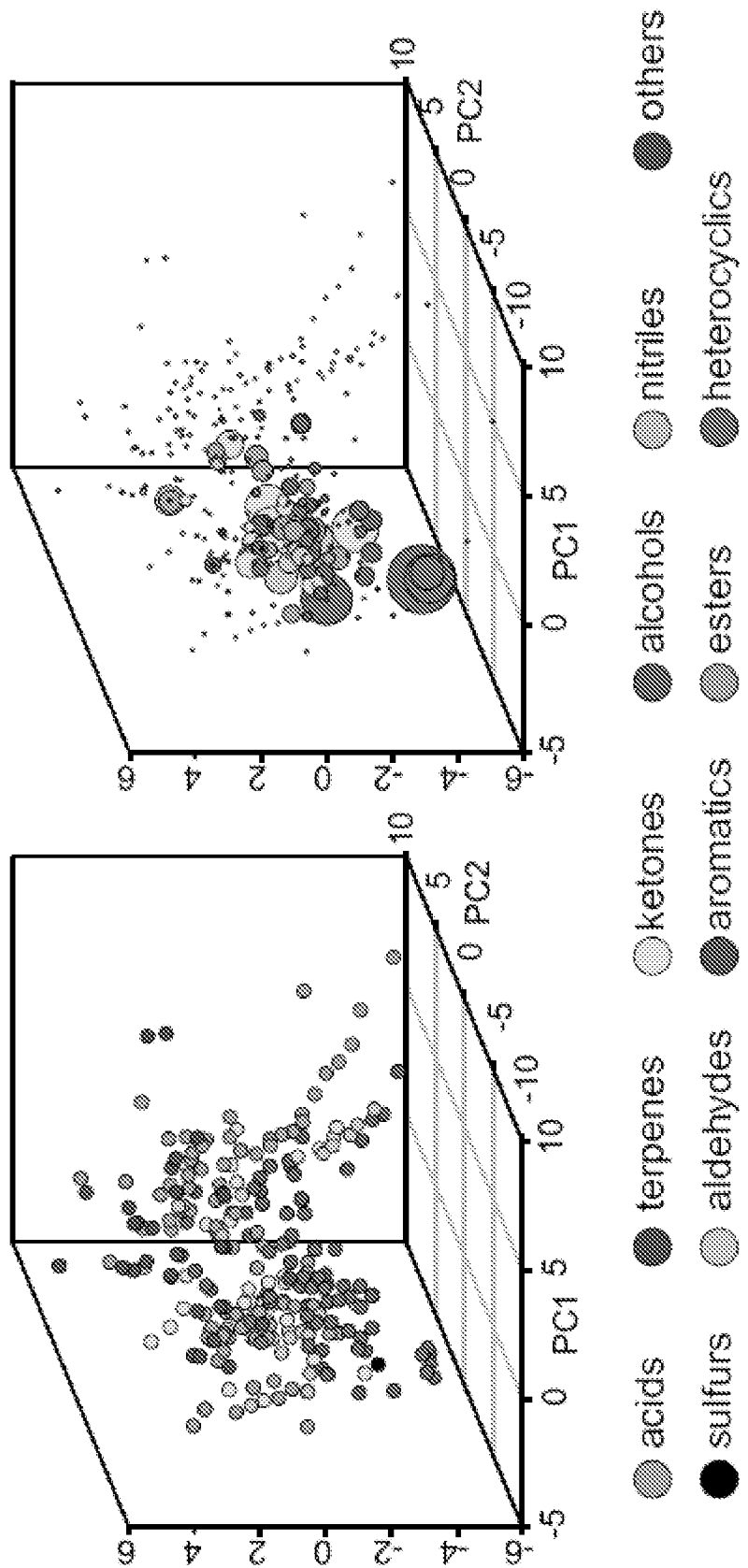
FIG. 5b illustrates the PCA analysis of FIG. 5a relabeled by chemical functional groups, with circle size representing their cpA activity (right).
Figure 5C:
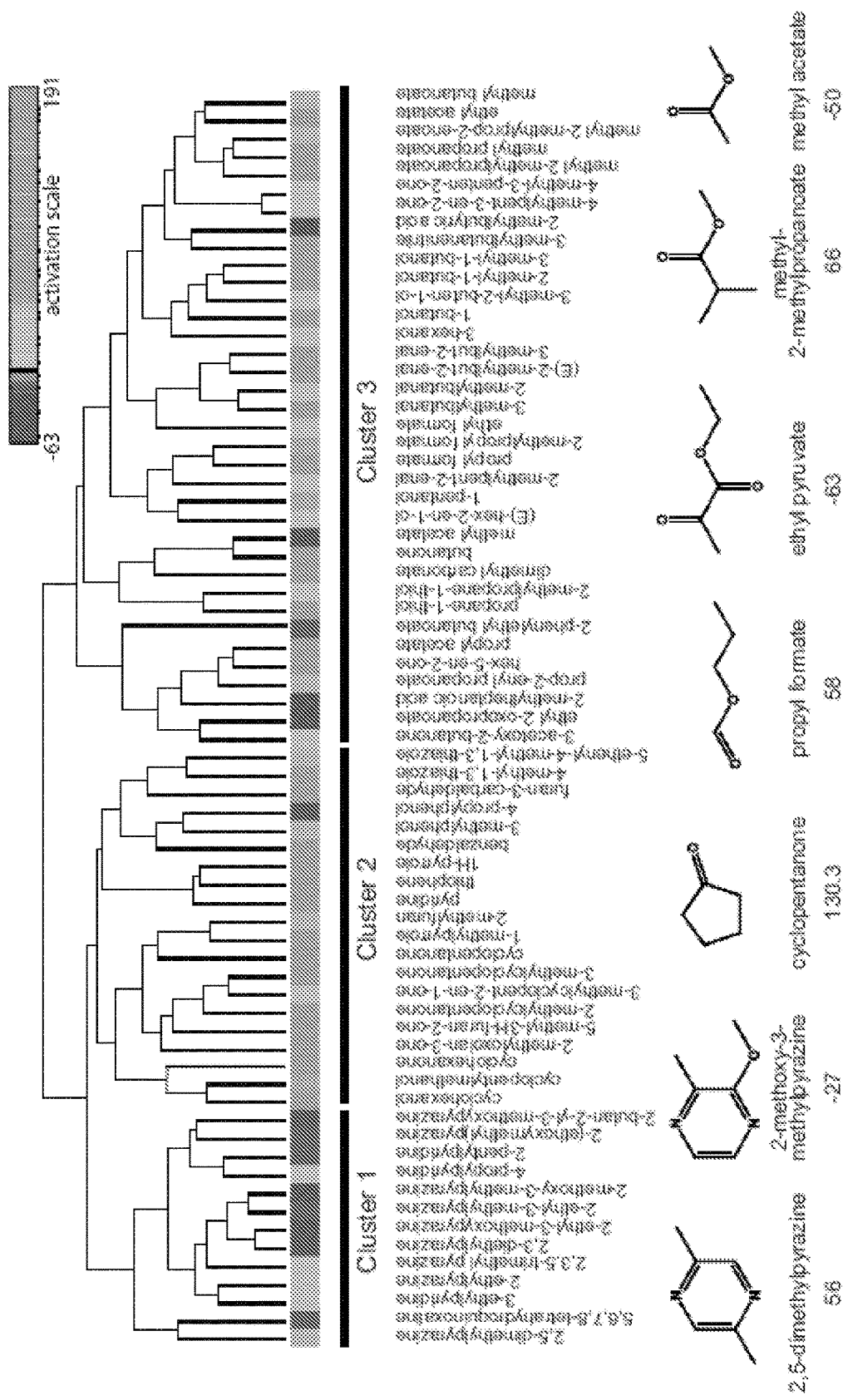
FIG. 5c is a hierarchical clustering of odorants that interact with cpA with inter-chemical distances generated from activity-optimized descriptors, and sample structures and associated activity are provided.

Next, this Example seeks to determine whether an additional set of 110 compounds that had previously been tested on an *A. gambiae* odor receptor (Or) repertoire, including many skin odorants, occupied a similar region of chemical space. Although these diverse compounds are broadly dispersed, they show limited overlap with the cpA ligand space (black dots, FIG. 5a). The functional groups were observed to distributed widely in optimized-descriptor defined chemical space (FIG. 5b). By superimposing activity of the cpA ligands using bubble plots as before, it becomes apparent that stronger ligands include chemicals from diverse functional classes (FIG. 5c). Presumably relevant parts of 3D chemical structure are more important in bringing these ligands together in chemical space than characteristics like functional group.

Hierarchical clustering was used to group ligands of the $CO_2$ receptor by structural similarity, measured by Euclidean distance in 64D optimized descriptor space (FIG. 5c). The resulting tree had roughly three branches, each populated by structurally distinct odor classes: substituted pyrazines and pyridines, other cyclic compounds, and short aliphatic chemicals. These three broad ligand classes and $CO_2$ appear structurally different, and it will be interesting to test whether they bind to different regions of the heteromeric $CO_2$ receptor (Gr1, Gr2, and Gr3).

Additionally, predictionary accuracy was increased through machine learning. The activities of the newly tested odorants (FIGS. 1c, 3b, and 3c) allowed for further improved ligand predictions for the $CO_2$ receptor. The activities of all tested odorants were used to identify a single optimized descriptor set as before (Table 4 below).

TABLE 4

Optimized descriptor set

| symbol | brief description | class | dimensionality |
|---|---|---|---|
| IAC | total information index of atomic composition | information indices | |
| TPSA(NO) | topological polar surface area using N, O polar contributions | molecular properties | 3 |
| EEig09d | Eigenvalue 09 from edge adj. matrix weighted by dipole moments | edge adjacency indices | 2 |
| R3e+ | R maximal autocorrelation of lag 3/ weighted by atomic Sanderson electronegativities | GETAWAY descriptors | 3 |
| ICR | radial centric information index | topological descriptors | 2 |
| nRCOOH | number of carboxylic acids (aliphatic) | functional group counts | 1 |
| nRNHR | number of secondary amines (aliphatic) | functional group counts | 1 |
| EEig10r | Eigenalue 10 from edge adj. matrix weighted by resonance integrals | edge adjacency indices | 2 |
| HATS5v | leverage-weighted autocorrelation of lag 5/weighted by atomic van der Waals volumes | GETAWAY descriptors | 3 |
| H3m | H autocorrelation of lag 3/weighted by atomic masses | GETAWAY descriptors | 3 |
| Mor27e | 3D-MorSE - signal 27/weighted by atomic Sanderson electronegativities | 3D-MoRSE descriptors | 3 |
| Mor11m | 3D-MorSE - signal 11/weighted by atomic masses | 3D-MoRSE descriptors | 3 |
| B02[N—O] | presence/absence of N—O at topological distance 02 | 2D binary fingerprints | 2 |
| R8e+ | R maximal autocorrelation of lag 8/ weighted by atomic Sanderson electronegativities | GETAWAY descriptors | 3 |
| O-057 | phenol/enol/carboxyl OH | atom-centred fragments | 1 |
| R4m | R autocorrelation of lag 4/weighted by atomic masses | GETAWAY descriptors | 3 |
| E2v | 2nd component accessibility directional WHIM index/weighted by atomic van der Waals volumes | WHIM descriptors | 3 |
| Mor30u | 3D-MorSE - signal 30/unweighted | 3D-MoRSE descriptors | 3 |

TABLE 4-continued

Optimized descriptor set

| symbol | brief description | class | dimensionality |
|---|---|---|---|
| R2v | R autocorrelation of lag 2/weighted by atomic van der Waals volumes | GETAWAY descriptors | 3 |
| F03[O-O] | frequency of O-O at topological distance 03 | 2D frequency fingerprints | 2 |
| C.016 | "=CHR" | atom-centred fragments | 1 |
| R4u+ | R maximal autocorrelation of lag 4/unweighted | GETAWAY descriptors | 3 |
| T(N...O) | sum of topological distances between N...O | topological descriptors | 2 |
| BELv2 | lowest eigenvalue n.2 of Burden matrix/weighted by atomic van der Waals volumes | Burden eigenvalues | 2 |
| Lop | Lopping centric index | topological descriptors | 2 |
| EEig08x | Eigenvalue 08 from edge adj. matrix weighted by edge degrees | edge adjacency indices | 2 |
| JGI1 | mean topological charge index of order1 | topological charge indices | 2 |
| HATS5p | leverage-weighted autocorrelation of lag 5/weighted by atomic polarizabilities | GETAWAY descriptors | 3 |
| EEig07x | Eigenvalue 07 from edge adj. matrix weighted by edge degrees | edge adjacency indices | 2 |

Figure 5E:
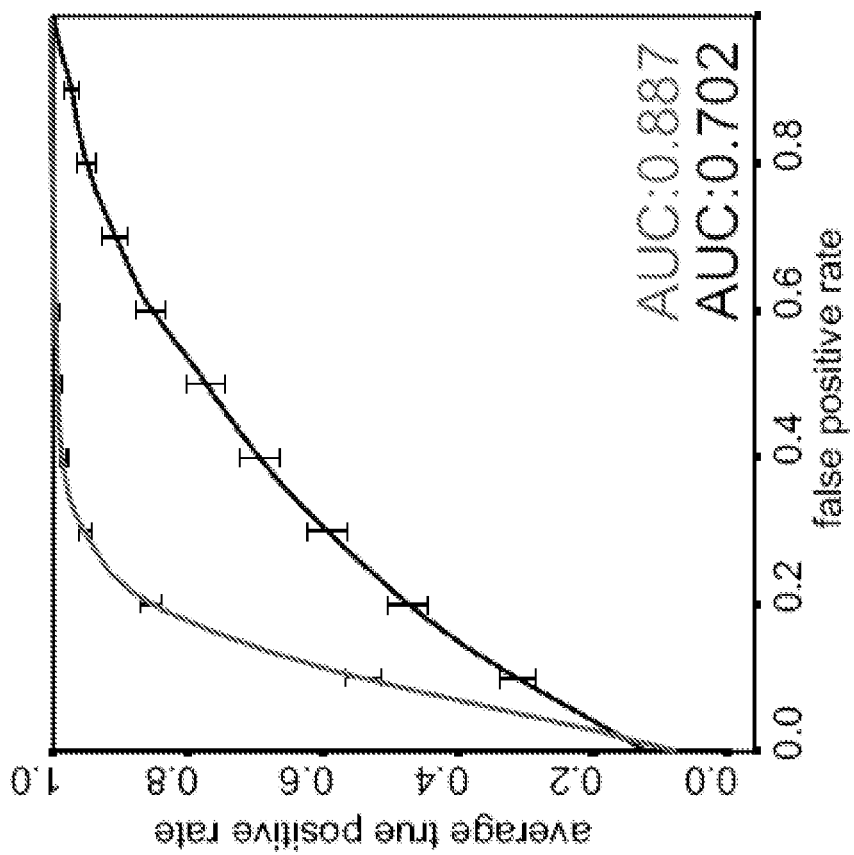
FIG. 5e is a graph illustrating the receiver-operating-characteristic curve (ROC) showing increased predictive accuracy of SVM method (red line) to our previous non-SVM method (black line) using a 5-fold cross-validation.
Figure 5D:
FIG. 5d provides an overview of the support vector machine (SVM) integrated pipeline to improve computational prediction of novel CpA ligands.
Figure 5D:
Figure 5F:
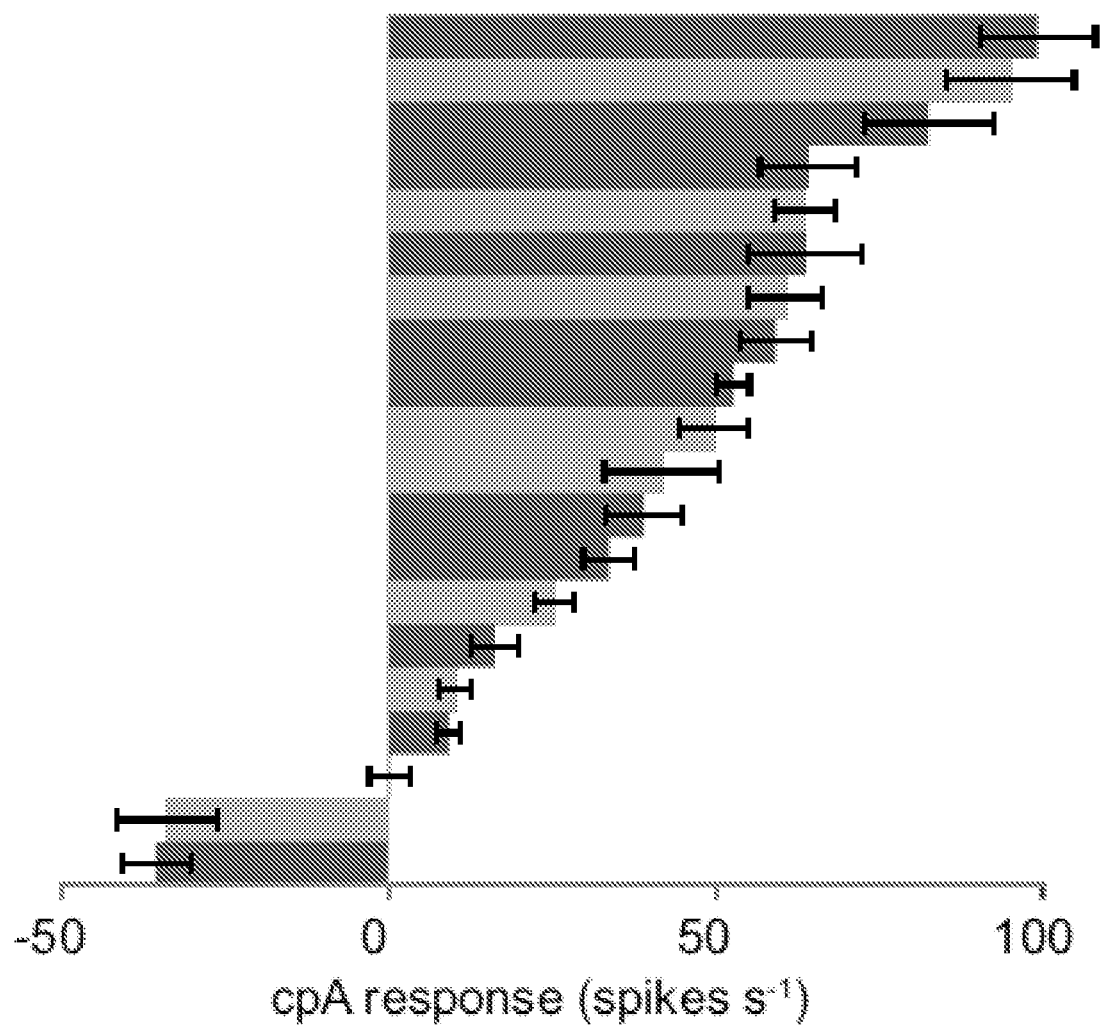
FIG. 5f is a bar graph illustrating the mean responses of the A. aegypti cpA neuron to 0.5-s pulses of 22 newly predicted compounds screened as in FIG. 3b, where salmon bars correspond to odorants found in human odor, odorants were diluted to $10^{-2}$ in paraffin oil or water, and responses to solvent have been subtracted, and n=2-5.

A machine learning approach called Support Vector Machine (SVM) was incorporated to select $CO_2$ receptor ligands. A widely applied computational validation called 5-fold cross validation indicated that the SVM based approach had a substantially higher Area-under-curve (AUC) value indicating improved ligand prediction (FIG. 5e). From the top 200 ligand predictions made using this method, 20 compounds were obtained and tested, of which 13 activated the cpA neuron >30 spikes$^{-1}$, and 2 inhibited the neuron, yielding a remarkably improved success rate of 75% (FIG. 5f, Table 5 below).

TABLE 5

| IUPAC | Activation (spikes s−1) | s.d. | s.e.m. | N |
|---|---|---|---|---|
| methylsulfanylmethane | 99.3 | 17.5 | 8.8 | 4 |
| 2-methylpropan-1-ol | 95.0 | 19.6 | 9.8 | 4 |
| 2-methyloxolane | 82.5 | 19.7 | 9.9 | 4 |
| 3-methylbut-3-en-1-ol | 64.3 | 14.8 | 7.4 | 4 |
| butan-2-ol | 63.8 | 9.2 | 4.6 | 4 |
| propan-2-yl formate | 63.8 | 17.3 | 8.6 | 4 |
| propan-1-ol | 60.8 | 11.3 | 5.6 | 4 |
| methyl formate | 59.3 | 11.2 | 5.6 | 4 |
| 3-methylsulfanylprop-1-ene | 52.8 | 5.0 | 2.5 | 4 |
| cyclopentanol | 49.8 | 10.8 | 5.4 | 4 |
| cyclopentane | 41.8 | 17.6 | 8.8 | 4 |
| 2,4-dimethyl-1,3-thiazole | 39.0 | 11.5 | 5.7 | 4 |
| 3-methylthiophene | 33.8 | 7.9 | 4.0 | 4 |
| propan-2-ol | 25.3 | 6.1 | 3.0 | 4 |
| methylcyclopentane | 16.3 | 7.0 | 3.5 | 4 |
| 1-pentene | 10.3 | 4.6 | 2.3 | 4 |
| 2-ethylthiophene | 9.3 | 3.6 | 1.8 | 4 |
| 2,5-dimethylthiophene | 0.3 | 6.2 | 3.1 | 4 |
| propanal | −33.8 | 15.1 | 7.6 | 4 |
| thiophene-2-thiol | −35.5 | 10.5 | 5.3 | 4 |

Example 8

Amines for Use as Repellents

This example demonstrates that certain polyamine compounds may exhibit repellent activity. The amines listed in Table 6 below were tested using an assay to determine inhibition of $CO_2$ receptor neuron activity.

TABLE 6

| Compound Name | % Inhibition | sem | N |
|---|---|---|---|
| 1-methylpyrrolidine | 100 | 0 | 4 |
| N-methylmethanamine | 100 | 0 | 4 |
| pentan-1-amine | 100 | 0 | 4 |
| N-N'-bis(3-aminopropyl)-1,4-butanediamine | 94.81 | 2.44 | 4 |
| N-(3-aminopropyl)-1,4-butanediamine | 92.25 | 6.07 | 6 |
| hexan-1-amine | 86.61 | 0.01 | 4 |

Dose response values for spermidine and spermine were also determined, as summarized in Table 7 below. The polyamines were diluted 0.001 to 10% in paraffin oil (PO). Also shown in Table 7 are the activity values of the $CO_2$ receptor neuron during the spermidine and spermine stimulus windows (error bars=s.e.m.).

TABLE 7

| Dose Response Series | Ave. Activity | s.d. | s.e.m. | Average % Inhibition | s.d. | s.e.m. |
|---|---|---|---|---|---|---|
| Paraffin Oil (n = 6) | 61.3 | 8.2 | 3.3 | 0.0 | 0.0 | 0.0 |
| Spermidine 0.001% (n = 6) | 62.3 | 12.1 | 4.9 | −1.0 | 9.3 | 3.8 |
| Spermidine 0.01% (n = 6) | 55.3 | 11.5 | 4.7 | 10.6 | 8.3 | 3.4 |

TABLE 7-continued

| Dose Response Series | Ave. Activity | s.d. | s.e.m. | Average % Inhibition | s.d. | s.e.m. |
|---|---|---|---|---|---|---|
| Spermidine 0.1% (n = 6) | 10.0 | 13.9 | 5.7 | 85.1 | 19.9 | 8.1 |
| Spermidine 1% (n = 6) | 5.3 | 10.4 | 4.2 | 92.2 | 14.9 | 6.1 |
| Spermidine 10% (n = 6) | 6.0 | 11.2 | 4.6 | 91.3 | 16.1 | 6.6 |
| Paraffin Oil (n = 10) | 51.8 | 11.0 | 3.5 | 0.0 | 0.0 | 0.0 |
| Spermine 0.001% (n = 6) | 52.0 | 10.9 | 4.4 | −5.6 | 6.2 | 2.5 |
| Spermine 0.01% (n = 6) | 52.3 | 9.0 | 3.7 | −3.2 | 10.9 | 4.4 |
| Spermine 0.1% (n = 10) | 14.0 | 14.1 | 4.5 | 76.5 | 22.1 | 7.0 |
| Spermine 1% (n = 6) | 2.7 | 2.7 | 1.1 | 94.8 | 6.0 | 2.4 |
| Spermine 10% (n = 6) | 2.3 | 3.7 | 1.5 | 95.1 | 8.3 | 3.4 |

What is claimed is:

1. A method of repelling an arthropod, comprising exposing the arthropod to a composition comprising methyl pyruvate, ethyl pyruvate, 3-methylbut-2-enal, or (E)-2-methylbut-2-enal, or any combinations thereof.

* * * * *